United States Patent
Lam et al.

(10) Patent No.: US 11,219,692 B2
(45) Date of Patent: Jan. 11, 2022

(54) PORPHYRIN MODIFIED TELODENDRIMERS

(71) Applicant: THE REGENTS OF THE UNIVERSITY OF CALIFORNIA, Oakland, CA (US)

(72) Inventors: Kit S. Lam, Oakland, CA (US); Yuanpei Li, Elk Grove, CA (US); Chong-Xian Pan, Davis, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 28 days.

(21) Appl. No.: 16/355,123

(22) Filed: Mar. 15, 2019

(65) Prior Publication Data

US 2020/0046841 A1 Feb. 13, 2020

Related U.S. Application Data

(60) Division of application No. 14/651,860, filed as application No. PCT/US2013/074762 on Dec. 12, (Continued)

(51) Int. Cl.
*A61K 9/00* (2006.01)
*A61K 47/60* (2017.01)
(Continued)

(52) U.S. Cl.
CPC ............ *A61K 47/60* (2017.08); *A61K 31/704* (2013.01); *A61K 41/0033* (2013.01);
(Continued)

(58) Field of Classification Search
CPC .................................................... A61K 47/60
See application file for complete search history.

(56) References Cited

U.S. PATENT DOCUMENTS

| | | | |
|---|---|---|---|
| 5,459,159 A * | 10/1995 | Pandey | A61P 35/00 514/410 |
| 6,365,191 B1 | 4/2002 | Burman et al. | |
| 6,630,128 B1 | 10/2003 | Love et al. | |
| 7,824,709 B2 | 11/2010 | Ryan et al. | |
| 8,895,055 B2 | 11/2014 | Lam et al. | |

(Continued)

FOREIGN PATENT DOCUMENTS

| | | |
|---|---|---|
| EP | 1230934 A | 8/2002 |
| EP | 1724295 A1 | 11/2006 |

(Continued)

OTHER PUBLICATIONS

Chen, et al., "Fluorescence Study of Inclusion Complexes between Star-Shaped Cholic Acid Derivatives and Polycyclic Aromatic Fluorescent Probes and the Size Effects of Host and Guest Molecules," Journal of Physical Chemistry, vol. 112, No. 11, pp. 3402-3409 (2008).

(Continued)

*Primary Examiner* — Paul W Dickinson
(74) *Attorney, Agent, or Firm* — Mintz, Levin, Cohn, Ferris, Glovsky and Popeo, P.C.

(57) ABSTRACT

The present invention provides amphiphilic telodendrimers that aggregate to form nanocarriers characterized by a hydrophobic core and a hydrophilic exterior. The nanocarrier core may include amphiphilic functionality such as cholic acid or cholic acid derivatives, and the exterior may include branched or linear poly(ethylene glycol) segments. Nanocarrier cargo such as hydrophobic drugs and other materials may be sequester in the core via non-covalent means or may be covalently bound to the telodendrimer building blocks. Telodendrimer structure may be tailored to alter loading properties, interactions with materials such as biological membranes, and other characteristics.

21 Claims, 32 Drawing Sheets

Related U.S. Application Data 2013, now Pat. No. 10,238,750, which is a continuation-in-part of application No. 13/803,878, filed on Mar. 14, 2013, now Pat. No. 9,642,916.

(60) Provisional application No. 61/736,067, filed on Dec. 12, 2012.

(51) Int. Cl.

| | |
|---|---|
| A61K 41/00 | (2020.01) |
| A61K 49/00 | (2006.01) |
| A61K 49/04 | (2006.01) |
| B82Y 5/00 | (2011.01) |
| A61K 49/18 | (2006.01) |
| A61K 51/12 | (2006.01) |
| A61K 47/62 | (2017.01) |
| A61K 47/69 | (2017.01) |
| A61K 31/704 | (2006.01) |
| A61N 5/06 | (2006.01) |

(52) U.S. Cl.
CPC ...... *A61K 41/0052* (2013.01); *A61K 41/0071* (2013.01); *A61K 41/0076* (2013.01); *A61K 47/62* (2017.08); *A61K 47/6907* (2017.08); *A61K 47/6911* (2017.08); *A61K 49/0002* (2013.01); *A61K 49/0036* (2013.01); *A61K 49/0082* (2013.01); *A61K 49/0423* (2013.01); *A61K 49/1809* (2013.01); *A61K 51/1227* (2013.01); *B82Y 5/00* (2013.01); *A61N 5/062* (2013.01)

(56) References Cited

U.S. PATENT DOCUMENTS

| | | |
|---|---|---|
| 9,579,400 B2 | 2/2017 | Lam et al. |
| 9,642,916 B2 | 5/2017 | Lam et al. |
| 10,106,650 B2 | 10/2018 | Lam et al. |
| 10,238,750 B2 | 3/2019 | Lam et al. |
| 10,406,233 B2 | 9/2019 | Luo et al. |
| 10,556,021 B2 | 2/2020 | Lam et al. |
| 2002/0041898 A1 | 4/2002 | Unger et al. |
| 2003/0027863 A1 | 2/2003 | Cruz et al. |
| 2003/0073679 A1 | 4/2003 | Mody et al. |
| 2005/0281777 A1 | 12/2005 | Albrecht et al. |
| 2006/0013885 A1 | 1/2006 | Nah et al. |
| 2006/0127310 A1 | 6/2006 | Russell-Jones et al. |
| 2008/0188399 A1 | 8/2008 | Sinko et al. |
| 2009/0203706 A1 | 8/2009 | Zhao et al. |
| 2010/0158994 A1 | 6/2010 | Watkin |
| 2011/0286915 A1 | 11/2011 | Lam et al. |
| 2012/0253191 A1 | 10/2012 | Zheng et al. |
| 2014/0363371 A1 | 12/2014 | Luo et al. |
| 2015/0045419 A1 | 2/2015 | Lam et al. |
| 2015/0056139 A1 | 2/2015 | Luo et al. |
| 2016/0038605 A1 | 2/2016 | Lam et al. |
| 2018/0036417 A1 | 2/2018 | Lam et al. |

FOREIGN PATENT DOCUMENTS

| | | |
|---|---|---|
| EP | 19167212 A | 9/2008 |
| EP | 2087912 A1 | 8/2009 |
| EP | 2793953 B1 | 10/2014 |
| EP | 2931290 B1 | 10/2015 |
| JP | 2001146556 A | 5/2001 |
| JP | 2005255810 A | 9/2005 |
| JP | 2012503603 A | 2/2012 |
| WO | 9959550 A1 | 11/1999 |
| WO | 0008467 A2 | 2/2000 |
| WO | 2008/091246 A1 | 7/2007 |
| WO | 2007084126 A1 | 7/2007 |
| WO | 2008062909 A1 | 5/2008 |
| WO | 2008/091246 A1 | 7/2008 |
| WO | 2008091247 A1 | 7/2008 |
| WO | 2009123934 A2 | 10/2009 |
| WO | 2009155335 A2 | 12/2009 |
| WO | 2010039496 A2 | 4/2010 |
| WO | 2010148346 A2 | 12/2010 |
| WO | 2012126115 A1 | 9/2012 |
| WO | 2012158622 A2 | 11/2012 |
| WO | WO-2012158622 A2 * | 11/2012 ............. A61P 35/00 |
| WO | 2013096388 A1 | 6/2013 |
| WO | 2014093675 A1 | 6/2014 |
| WO | 2016172635 A1 | 10/2016 |
| WO | 2018136778 A1 | 7/2018 |
| WO | 2019051121 A1 | 3/2019 |

OTHER PUBLICATIONS

Duncan, "Dawning Era of Polymer Therapeutics," Nature Rev. Drug. Discov., vol. 2, No. 5, pp. 347-360 (2003).
European Application No. 12860828.8, Extended European Search Report, dated Mar. 10, 2016, 16 pages.
European Search Report for European Application No. EP 12 78 6464 dated Oct. 29, 2014, 7 pages.
Giuntini et al., "Synthetic approaches for the conjugation of porphyrins and related macrocycles to peptides and proteins", Photchem. Photobiol. Sci., Apr. 1, 2011; pp. 759-791; vol. 10; the Royal Society of Chemistry and Owner Societies.
Gref, et al., "Biodegradable Long-Circulating Polymeric Nanospheres," Science American Association for the Advancement of Science, vol. 263, No. 5153, pp. 1600-1603 (1994).
Xiao, et al., PEG-oligocholic acid telodendrimer micelles for the targeted delivery of doxorubicin to B-cell lymphoma, JCR, 155, pp. 272-281 (2011).
Heffernan et al., "Disulfide-Cross linked Polyion Micelles for Delivery of Protein Therapeutics," Annals of Biomedical Engineering. vol. 37, No. 10, Oct. 2009, pp. 1993-2002.
Huh et al., "Hydrotropic polymer micelle system for delivery of paclitaxel," Journal of Controlled Release 101 (2005) 59-68.
International Preliminary Report on Patentability dated Apr. 7, 2011, issued in related International Patent Application No. PCT/US2009/057852, 9 pages.
International Search Report dated May 6, 2010, issued in related International Patent Application No. PCT/US2009/057852, 19 pages.
International Search Report and Written Opinion for PCT/US2012/037794, dated Jan. 28, 2013, 10 pages.
International Search Report and Written Opinion for PCT/US12/70508, 11 pages, dated Feb. 27, 2013.
Japanese Application No. 2011-528068, Office Action dated Dec. 25, 2013, 2 pages.
Japanese Application No. 2014-510540, Office Action dated Jan. 5, 2016, 7 pages.
Kaminskas et al., "PEGylation of polylysine dendrimers improves absorption and lymphatic targeting following SC administration in rats," Journal of Controlled Release, 140, 2009, pp. 108-116.
Kaminskas et al., "The Impact of Molecular Weight and PEG Chain length on the Systemic Pharmacokinetics of PEGylated Poly L-lysine Dendrimers," Molecular Pharmaceutics, 2008, vol. 5, No. 3, pp. 449-463.
Li et al., "Antimicrobial Activities of Amine- and Guanidine-Functionalized Cholic Acid Derivatives", Antimicrobial Agents and Chemotherapy, vol. 43(6), pp. 147-1349 (Jun. 1999).
Li, et al., "Well-defined, reversible disulfide cross-linked micelles for on-demand paclitaxel delivery", Biomaterials, vol. 32, Issue 27, pp. 6633-6645 (Sep. 30, 2011).
Li, et al., "Well-Defined, Reversible Boronate Crosslinked Nanocarriers for Targeted Drug Delivery in Response to Acidic pH Values and cis-Diols", Angewandte Chemie, vol. 124, Issue 12, pp. 2918-2923 (Mar. 19, 2012).
Luo, et al., "Asymmetric Poly(ethylene glycol) Star Polymers with a Cholic Acid Core and Their Aggregation Properties," Biomacromolecules, vol. 10, No. 4, pp. 900-906 (2009).
Vijayalakshmi, et al., "A Simple Construction of a Bile Acid Based Dendritic Light Harvesting System," Organic Letters, vol. 7, No. 13, pp. 2727-2730 (2005).
Xiao, et al., "A self-assembling nanoparticle for paclitaxel delivery in ovarian cancer," Biomaterials, vol. 30, No. 30, pp. 6006-6016 (2009).

(56) References Cited

OTHER PUBLICATIONS

Extended European Search Report dated Jul. 26, 2016 in EP 13863207.0, 7 pages.
International Search Report for International Application No. PCT/US2012/074762, dated Apr. 21, 2014, 3 pages.
Chapman et al., "Hydraamphiphiles: Novel Linear Dendritic Block Copolymer Surfactants", J. Am. Chem. Soc., 1994, vol. 116, pp. 11195-11196.
Choi et al., "Poly(ethylene glycol)-block-poly(L-lysine) Dendrimer: Novel Linear Polymer/Dendrimer Block Copolymer Forming a Spherical Water-Soluble Polyionic Complex with DNA", Bioconjugate Chem., 1999, pp. 62-65.
Li et al., "Dendrimer Generation Effects on Photodynamic Efficacy of Dendrimer Porphyrins and Dendrimer-Loaded Supramolecular Nanocarriers", Chemistry of Materials, Nov. 2007, 19(23):5557-5562.
Notice of Reasons for Rejection for JP application No. 2015-547561, dated Oct. 24, 2017; (with English Translation).
Notice of Allowance dated Oct. 14, 2016 in U.S. Appl. No. 13/803,878, 19 pages.
Gu et al. (Dec. 21, 2007) "pH-Triggered Reversible "Stealth" Polycationic Micelles", Biomacromolecules, 9 (1):255-262.
Li et al. (Jun. 15, 2010) "A Novel Size-tunable Nanocarrier System for Targeted Anticancer Drug Delivery", Author Manuscript, Published in final edited form as: Journal of Controlled Release, 144(3):23 Pages.
Luo et al. (Jul. 21, 2010) "Well-defined, Size-tunable, Multifunctional Micelles for Efficient Paclitaxel Delivery for Cancer Treatment", Author Manuscript, Published in final edited form as: Bioconjugate Chemistry, 21(7):1216-1224.
Xiao et al. (Oct. 2013) "Telodendrimer-based Nanocarriers for the Treatment of Ovarian Cancer", Author Manuscript, Published in final edited form as: Therapeutic Delivery, 4(10):1279-1292.

* cited by examiner

FIG. 4A
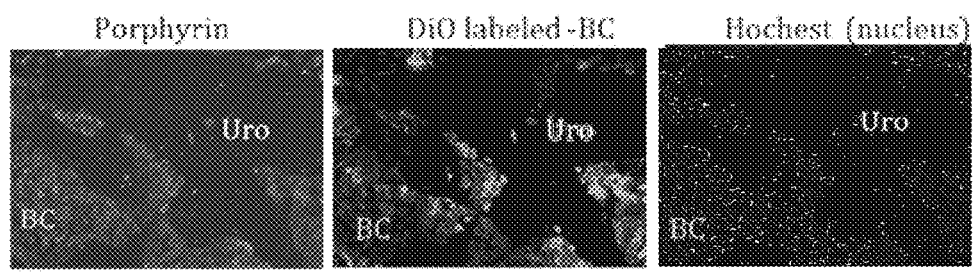
FIG. 4B
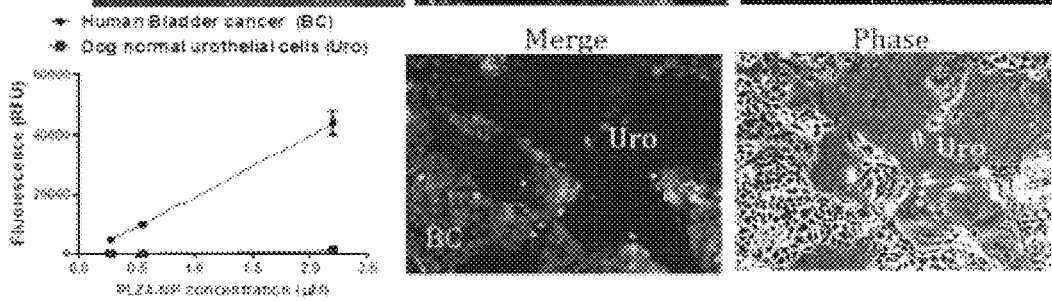
FIG. 5
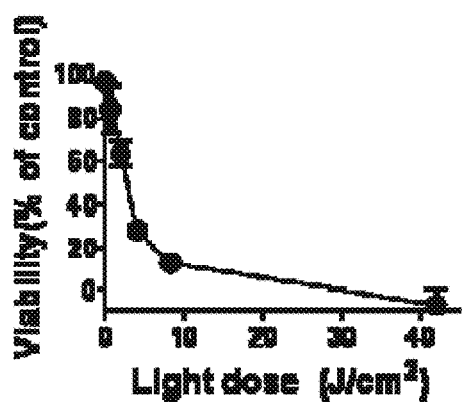
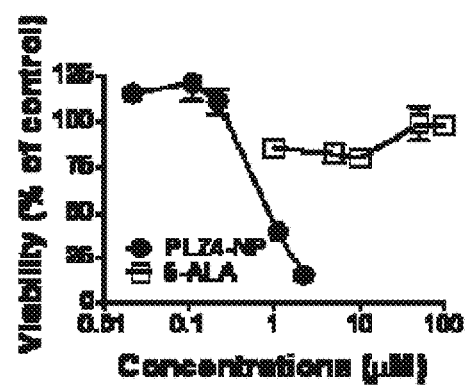

FIG. 6A
FIG. 6B
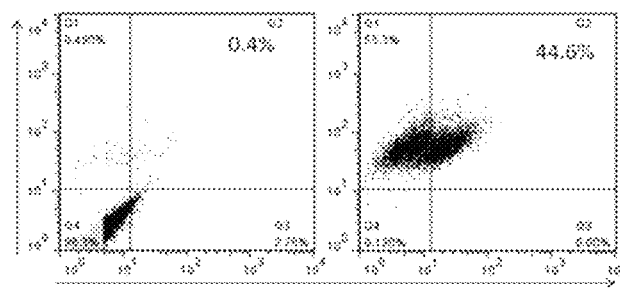
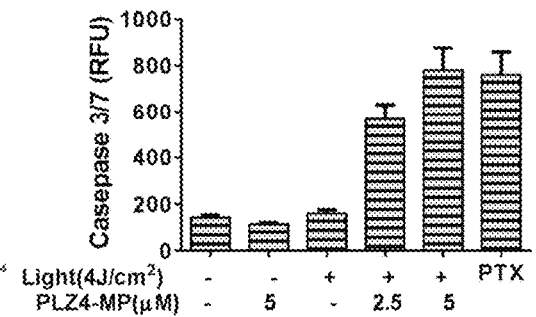
FIG. 7
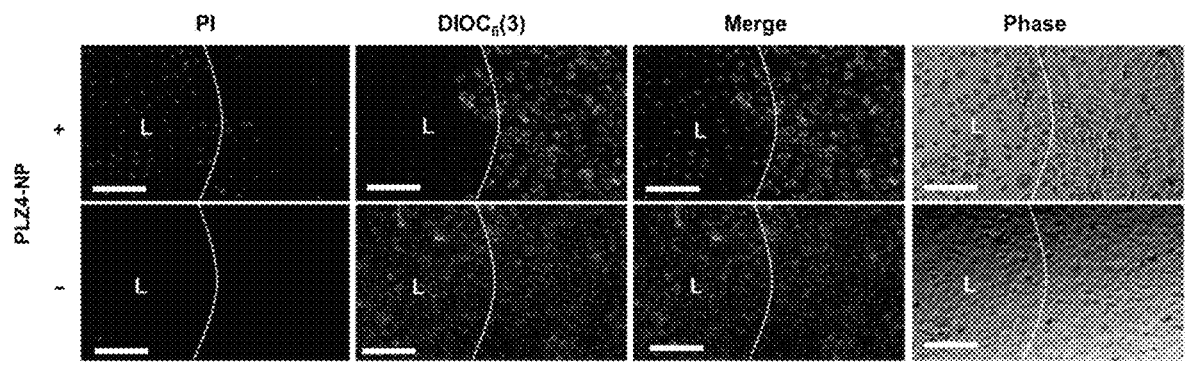

NPs in PBS

NPs in SDS

NM-POR in PBS

NM-POR in SDS

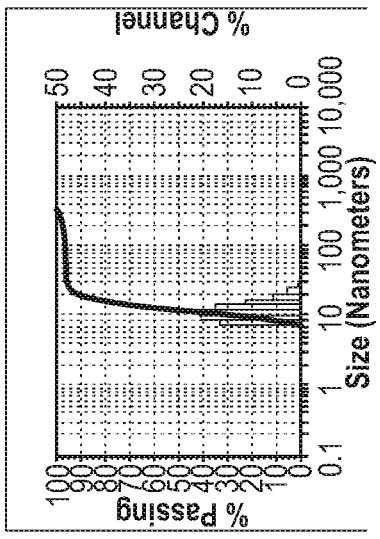
FIG. 25A NP-doxorubicin
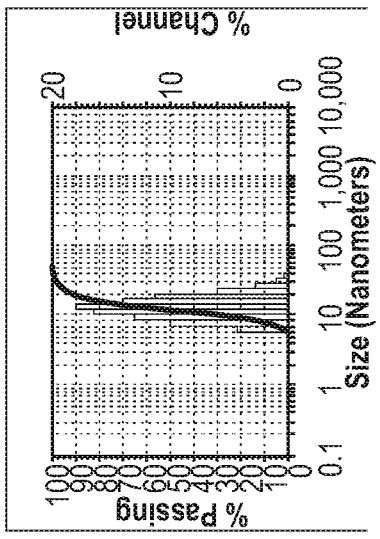
FIG. 25B NP-paclitaxel
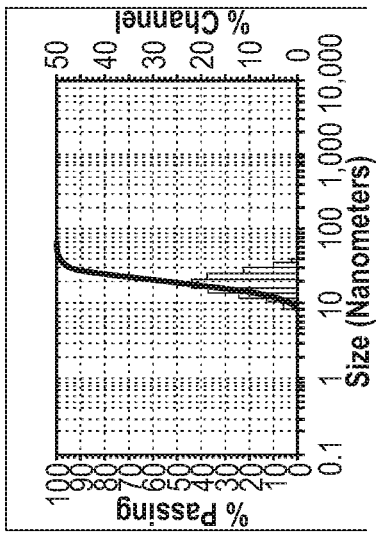# 
FIG. 25C NP-vincristine
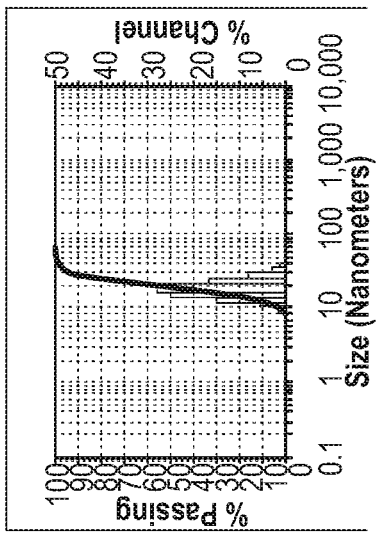
FIG. 25D NP-bortezomib
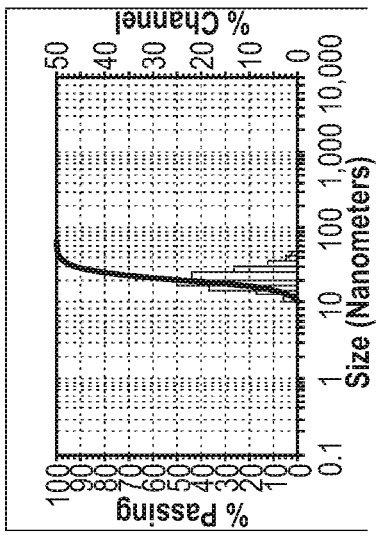
FIG. 25E NP-sorafenib
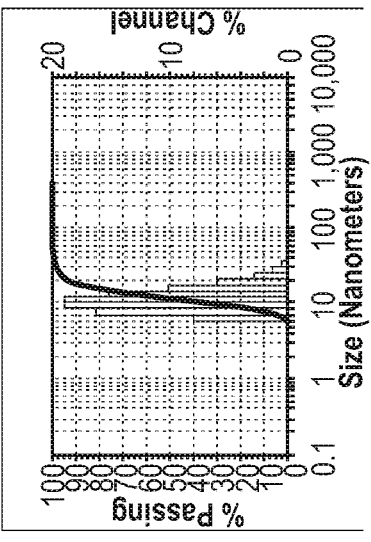
FIG. 25F NP-17AAG

PORPHYRIN MODIFIED TELODENDRIMERS

CROSS-REFERENCES TO RELATED APPLICATIONS

This application is a divisional of U.S. application Ser. No. 14/651,860, filed Jun. 12, 2015, now U.S. Pat. No. 10,238,750, which is the U.S. National Stage Entry under § 371 of International Application No. PCT/US2013/074762, filed Dec. 12, 2013, which is a continuation-in-part of U.S. application Ser. No. 13/803,878, filed Mar. 14, 2013, now U.S. Pat. No. 9,642,916, which claims priority to U.S. Provisional Application No. 61/736,067, filed Dec. 12, 2012, each of which is incorporated in its entirety herein for all purposes.

STATEMENT AS TO RIGHTS TO INVENTIONS MADE UNDER FEDERALLY SPONSORED RESEARCH AND DEVELOPMENT

This invention was made with Government support under Grant No. 2R01CA115483-06, awarded by the National Institutes of Health and the National Cancer Institute, and a VA Career Development Award-2. The Government has certain rights in this invention.

BACKGROUND OF THE INVENTION

Several effective chemotherapeutic agents for treatment of various cancer types are very insoluble in water, requiring formulations that induce unwanted side effects. Recently, nanotherapeutic formulations such as Abraxane® (paclitaxel-loaded albumin nanoparticles), Doxil® (doxorubicin-loaded liposomes), and others have been shown to improve the clinical toxicity profiles of the drugs, but their anti-tumor effects are only marginally better than the original drug formulations. This has been attributed in part to the relatively large size of the nanotherapeutic formulations (generally >100 nm), which limits the extent to which the drugs can penetrate into tumor mass. In some cases, this large size also causes nanotherapeutics to be trapped in the liver and reticuloendothelial system (RES). Accordingly, there is a need to develop smaller (20-80 nm) stealth and biocompatible nanocarriers for effective delivery anticancer drugs in vivo.

We have recently developed several novel nanocarriers for paclitaxel (PTX) or other hydrophobic drugs. These novel nanocarriers, comprising poly(ethylene glycol) (PEG) and oligo-cholic acids, can self-assemble under aqueous conditions to form core-shell (cholane-PEG) structures that can carry PTX in the hydrophobic interior. These amphiphilic drug-loaded nanoparticles are therapeutic by themselves with improved clinical toxicity profiles. More importantly, when decorated with cancer cell surface targeting ligands and/or tumor blood vessel ligands, these nanocarriers will be able to deliver toxic therapeutic agents to the tumor sites. The final size of the nanocarriers (10 to 100 nm) is tunable by using various, or a combination of, different cholane-PEG preparations. The nanocarrier components, PEG and cholic acid, are all biocompatible and largely non-toxic. Indeed, the PTX nanotherapeutics exhibited safe profile in in vivo administration for anticancer treatment in mouse models and companion dogs. However, the nanocarriers have demonstrated some hemolytic activity both in vitro and in vivo, as well as reduced loading capacity for certain drugs. Therefore, there is a need to develop nanocarriers with improved biocompatibility and versatility.

The present invention is based on the surprising discovery that certain changes to the hydrophilic and hydrophobic segments of the constituent building blocks improve the therapeutic properties without disrupting nanocarrier assembly, addressing the needs described above.

BRIEF SUMMARY OF THE INVENTION

In some embodiments, the present invention provides a compound of formula I:

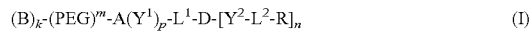

$$(B)_k\text{-}(PEG)^m\text{-}A(Y^1)_p\text{-}L^1\text{-}D\text{-}[Y^2\text{-}L^2\text{-}R]_n \quad (I)$$

wherein B can be a binding ligand; each PEG can be a polyethyleneglycol (PEG) polymer having a molecular weight of 1-100 kDa; A includes at least one branched monomer unit X and can be linked to at least one PEG group; D can be a dendritic polymer having a single focal point group, a plurality of branched monomer units X and a plurality of end groups; each $Y^1$ and $Y^2$ can be absent or a crosslinkable group that can be boronic acid, dihydroxybenzene or a thiol; each $L^1$ and $L^2$ can independently be a bond or a linker, wherein $L^1$ can be linked to the focal point group of the dendritic polymer; each R can independently be the end group of the dendritic polymer, a porphyrin, a hydrophobic group, a hydrophilic group, an amphiphilic compound or a drug, wherein at least one R group can be a porphyrin; subscript k can be 0 or 1; subscript m can be an integer from 0 to 20; subscript n can be an integer from 2 to 20, wherein subscript n can be equal to the number of end groups on the dendritic polymer; and subscript p can be from 0 to 8.

In some embodiments, the invention provides a nanocarrier having an interior and an exterior, the nanocarrier comprising a plurality of the dendrimer conjugates of the invention, wherein each compound self-assembles in an aqueous solvent to form the nanocarrier such that a hydrophobic pocket is formed in the interior of the nanocarrier, and wherein the PEG of each compound self-assembles on the exterior of the nanocarrier.

In some embodiments, the present invention provides a method of treating a disease via photodynamic or photothermal therapy, including administering to a subject in need thereof, a therapeutically effective amount of a nanocarrier of the present invention, and exposing the subject to radiation, thereby treating the disease via photodynamic or photothermal therapy.

BRIEF DESCRIPTION OF THE FIGURES

FIG. 3C Human bladder cancer cell line 5637 was incubated with 2.2 μM of PLZ4-NP for 20 min in a glass bottom dish. After adding DAPI containing medium for nucleus staining, live cell imaging was acquired using high resolution topography imaging system (Delta vision). Arrows indicated the membrane distribution. FIG. 3D 5637 was treated with 2.2 µM of PLZ4-NP for 2 hr. After washed, cells were than cultured for another 0, 24, 48, and 72 hr in fresh complete medium. Cells were than trypsinzed and fixed in 10% formal before test and cells were analyzed by flow cytometry.

FIG. 4A-4B shows PLZ4-NP specifically uptake by bladder cancer cells but not normal urothelial cells. FIG. 4A Co culture of normal canine urothelial cells (Uro) with pre DiO labeled human bladder cancer cell line 5637(BC) was treated with PLz4-NP for 2 hours. (pophryin: red; DiO: green; Hochest: blue) (100×)

FIG. 5 shows cytotoxicity of 5637 bladder cancer cells after 2 hrs exposure to 2.2 µM PLZ4-NP followed by illumination with various level of light (red light, 650 nm wave length), and incubation with PLZ4-NP or 5-ALA for 2 hrs followed by exposure to 4.2 J/cm2 of red light.

FIG. 6A-6B shows ROS mediated cell death after PZL4-NP and PDT treatment of 5637 human bladder cancer cells FIG. 6A cells were treated with or without 2.2 µM PZL4-NP for 2 hr and loaded with aminophenyl fluorescein (APF; an ROS indicator) for 30 min. After that, cells were treated with PDT at 4.2 J/cm$^2$ and analyzed with flow cytometry; FIG. 6B cells were treated with different concentrations of PZL4-NP for 2 hr followed by PDT. 24 hr later, caspase3/7 activity was measured by SensoLyte® Kit (Anaspec, Fremont, Calif.). (PTX is paclitaxel treatment as a positive control for apoptosis)

FIG. 7 shows 5637 cells were incubated with 2.2 µM PZL4-NP for 2 hr in 96-well black-wall plate, stained with 40 nM of DiOC$_6$(3) (Green, $\Delta\Psi m^{high}$) for 20 min in the end of incubation to evaluate mitochondria membrane potential ($\Delta\Psi m$), and followed by illumination of a portion of each well to elicit PDT effect. 24 hr later, the cells were stained with propridium iodide for cell death.

FIG. 9A Human patient derived xenograft (PDX) BL269f was established in NSG mice. Mouse orthotopic model of BL269f was generated by directly injected suspension BL269f cells into bladder wall. After 4 weeks, the growth of solid tumor was noted with decreased bladder lumen capacity. We injected 30 µl of PLZ4-NP into bladder for 2 hr under general anesthesia. Bladder was washed with PBS and isolated outside of body for in vivo imaging. Afterwards, mice were immediately sacrificed and major organs were dissected for ex vivo imaging. Similar experiments were done in normal NSG mice without bladder tumor transplantation. FIG. 9B Bladders with or without BL269f xenograft were fixed in O.C.T and 10 microns thick of cryosections were obtained. Nucleus was counter stained by DAPI (blue), and intracellular PLZ4-NP fluoresce red. After fluorescent imaging study, the tissue was re-stained with Hema3®. (yellow arrow: exposed bladder cancer tissue, red arrow: intact normal urothelial cells.) (40×)

FIG. 11A 5637 cells were treated with PLZ4-NP, PLZ4-NP-Dox or PLZ4-NM-Dox at the concentration of 1 µg/ml Doxorubicine and/or 2.2 µM porphyrin for 2 hours. After wash, cells were exposed without or with light at 2.1 and 4.2 J/cm2. Cell viability was measured after 48 hours. *p<0.05 FIG. 11B 5637 cells were treated with PLZ4-NP, PLZ4-NP-Dox, free Dox, Doxil, PLZ4-NM-Dox, and a combination of PLZ4-NP and PLZ4-NM-Dox for 5 minutes and 2 hours. Intracellular doxorubicin concentration was evaluated with flow cytometry. This results present at mean+/−SD from 3 different independent experiments. *p<0.05; **p<0.01 FIG. 11C 5637 cells were treated with PLZ4-NP (PNP), PLZ4-NM-DOX(PN-DOX), a combination of PNP and PN-DOX, and PLZ4-NP-DOX(PNP-DOX) for 2 hours. Porphrin (red) and doxorubicine (green) were detected by fluoresces microscope. (100×) FIG. 11D Sub-cellular distribution of PLZ4-NP-DOX (PNP-DOX) was detected by confocal microscope. (600× oil) at 5 minutes, 1 and 3 hours. Cells were washed but not fixed. PNP (porphyrin: red), Doxorubicin (green)

FIG. 12A a schematic illustration of a multifunctional, self-assembled porphyrin-telodendrimer, PEG$^{5k}$-Por$_4$-CA$_4$, having 4 pyropheophorbide-a molecules and 4 cholic acids attached to the terminal end of a linear PEG chain; FIG. 12B a schematic illustration of nanoporphyrins as a smart "eight-in-one" nanomedicine platform for cancer treatment; FIG. 12C a TEM image of nanoporphyrins (stained with phosphotungstic acid, PTA); FIG. 12D the absorbance spectra of empty nanoporphyrins and nanoporphyrins after chelating different metal ions; nanoporphyrins loaded with Cu(II) FIG. 12E) and Gd(III) FIG. 12F viewed with TEM (stained with PTA); FIG. 12G fluorescence emission spectra of nanoporphyrins in the presence of PBS and SDS, with excitation at 405 nm; FIG. 12H near-infrared fluorescence imaging of a nanoporphyrin solution (10 µL) in the absence and in the presence of SDS with an excitation bandpass filter at 625/20 nm and an emission filter at 700/35 nm; FIG. 12I single oxygen generation of nanopophyrins (0.125 mg/mL) in PBS and SDS measured by using 2',7'-dichlorofluorescein diacetate (DCF) as a ROS indicator; concentration-dependent photo-thermal transduction of nanoporphyrins, including FIG. 12J thermal images and FIG. 12K quantitative temperature change curves (n=2), wherein the temperature of nanoporphyrin solution (10 µL) in the absence and in the presence of SDS was monitored by a thermal camera after irradiation with a NIR laser (690 nm) at 1.25 w/cm$^2$ for 20 seconds; and FIG. 12L a representative thermal image of a nanoporphyrin solution with high temperature achieved by irradiating the solution (4.0 mg/mL) with a NIR laser at 1.25 w/cm$^2$ for 120 seconds.

FIG. 16A a schematic illustration of a representative crosslinkable porphyrin-telodendrimer ($PEG^{5k}$-$Cys_4$-$Por_4$-$CA_4$), having 4 cysteines, 4 pyropheophorbide-a molecules and 4 cholic acids attached to the terminal end of a linear PEG chain, with Ebes used as a spacer; FIG. 16B a TEM image of the disulfide crosslinked nanoporphyrins (stained with PTA); FIG. 16C the fluorescence emission spectra of the crosslinked nanoporphyrins in the presence of PBS and SDS in the comparison with the non-crosslinked nanoporphyrins, wherein glutathione (GSH) was used as a reducing agent to break the disulfide crosslinking (excitation at 405 nm); FIG. 16D doxorubicin loading and size change of disulfide crosslinked NPs versus the level of drug added at initial loading, wherein the volume of the final NP solution was kept at 1 mL and the final concentration of the telodendrimer was 20 mg/mL; FIG. 16E a schematic illustration of a FRET-based approach for study of the real-time release of doxorubicin from nanoporphyrins in human plasma; FRET signal FIG. 16F and changes in FRET ratio FIG. 16G of doxorubicin-loaded crosslinked nanoporphyrins (CNP-DOX) in human plasma with irradiation (1.25 w/cm$^2$ for 5 min) at 24 hrs and 28 hrs; and FIG. 16H changes in FRET ratio of NP-DOX in human plasma treated with GSH (10 mM) at 24 hrs.

FIG. 25A-25F shows the particle size of non-crosslinked nanoporphyrins (20 mg/mL) after loading of FIG. 25A doxorubicin (2.5 mg/mL), FIG. 25B paclitaxel (1.0 mg/mL), FIG. 25C vincristine (1.5 mg/mL), FIG. 25D bortezomib (2.0 mg/mL), FIG. 25E sorafenib (2.0 mg/mL), and FIG. 25F 17-allylamino-17-demethoxygeldanamycin (17AAG) (1.0 mg/mL). The particle size was measured by dynamic light scattering (DLS).

FIG. 26 shows continuous particle size measurements of DOX-loaded crosslinked NPs (NP-DOX) in the presence of 50% percent (v/v) of human plasma.

DETAILED DESCRIPTION OF THE INVENTION

I. Definitions

Figure 1:
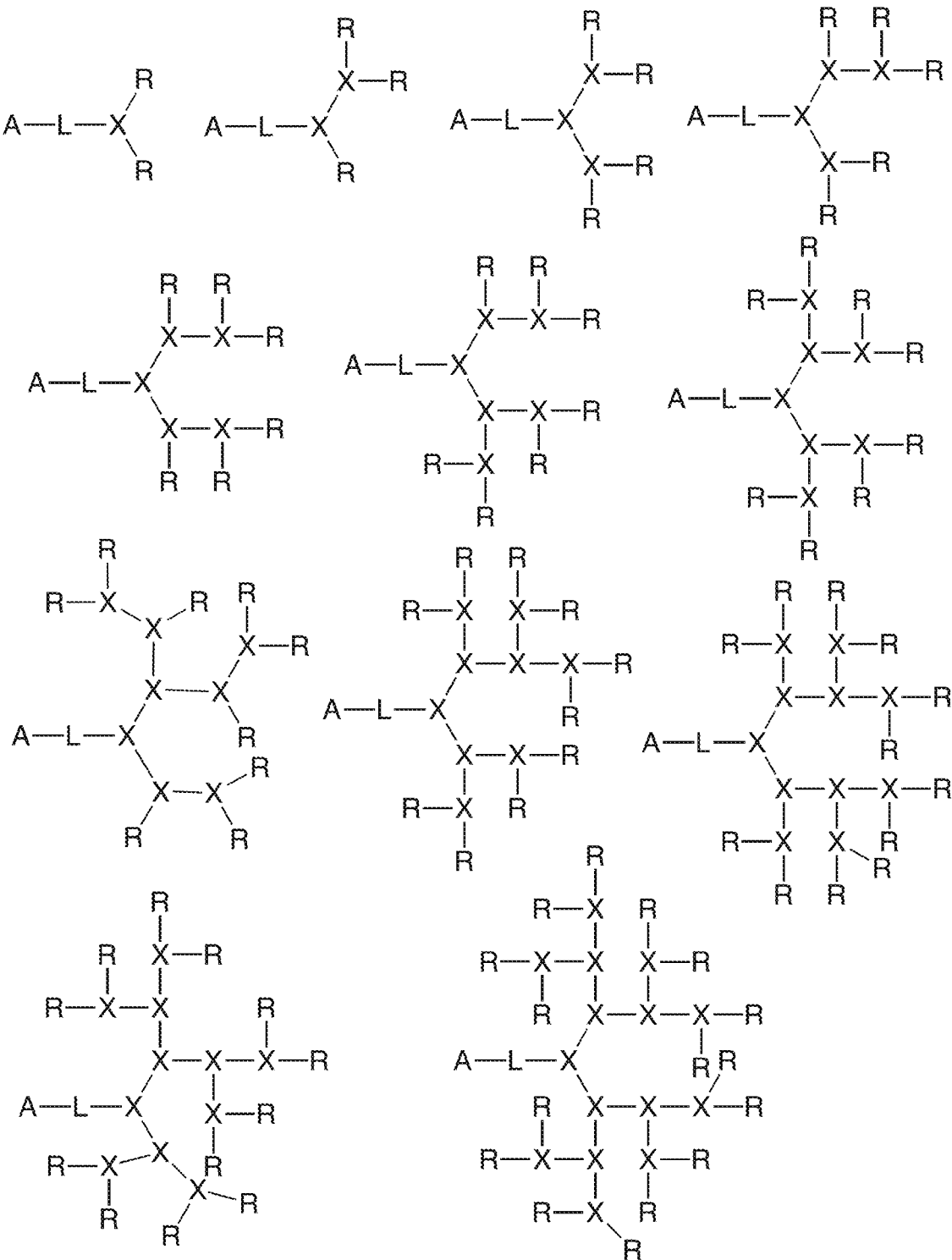
FIG. 1 shows several embodiments of the branched nature of the telodendrimers of the present invention.
Figure 2A:
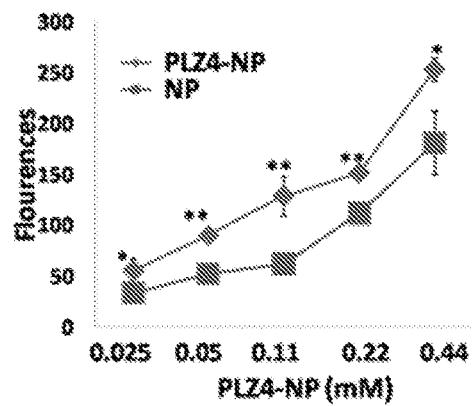
FIG. 2 shows cellular uptake of non-targeting NP vs PLZ4-NP into 5637 human bladder cancer cells after 4 hr incubation. (b) K9TCC-Pu-In cells were preincubated with free PLZ4 peptide for one hr and followed by incubation with 2.2 μM of PLZ4-NP for another hr. Cells without free PLZ4 treatment were served as 100% control. Cells were fixed in formalin and analyzed by flow cytometry.
Figure 2B:
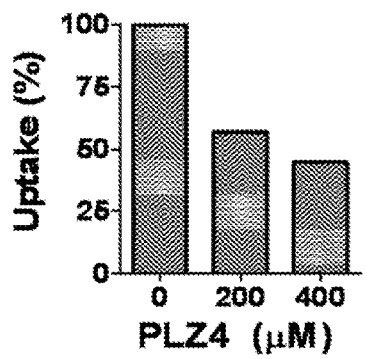
Figure 3A:
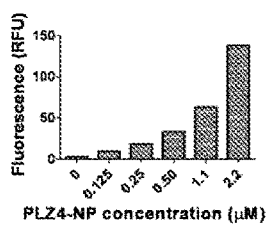
FIG. 3A-3D shows cellular uptake of PLZ4-NP by K9TCC-Pu-In bladder cancer cells as a function of FIG. 3A PLZ4-NP concentration (4 hr incubation), and FIG. 3B time (2.2 μM PLZ4-NP).
Figure 3B:
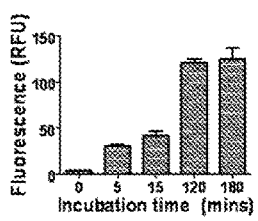
Figure 3C:
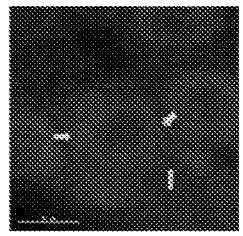
Figure 3D:
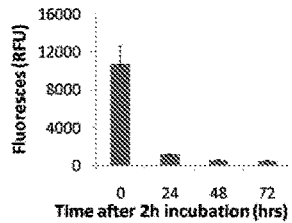
Figure 8:
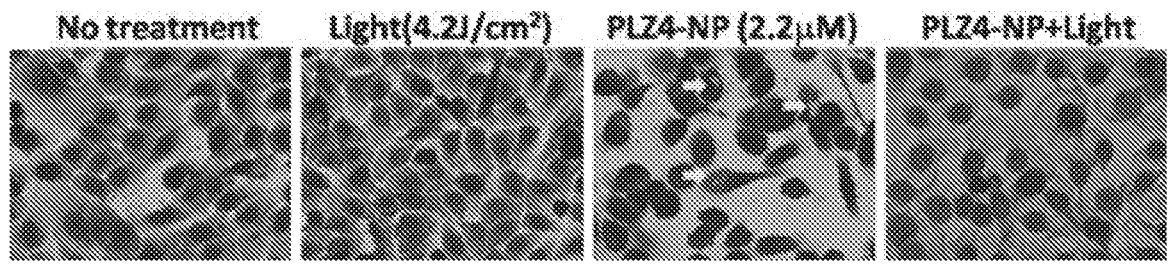
FIG. 8 shows cell morphology after PDT. 5637 cells were cultured on the 8-well chamber slides and treated for 2 hr with none, light alone (4.2 J/cm$^2$), PLZ4-NP alone or combination of PLZ4-NP and light (PDT), or T-PN for two hr followed by PDT. Cells were then fixed and stained with Hema3®.
Figure 9A:
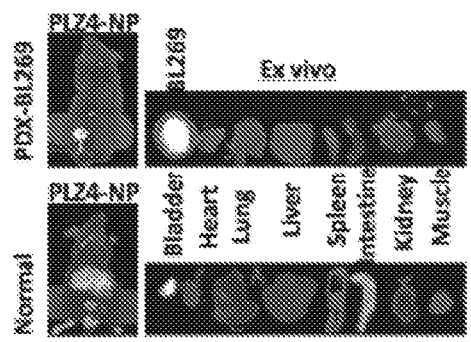
FIG. 9A-9C shows selective uptake of PLZ4-NP into an orthotopic human bladder cancer xenograft model after intravesical administration into nude mouse.
Figure 9C:
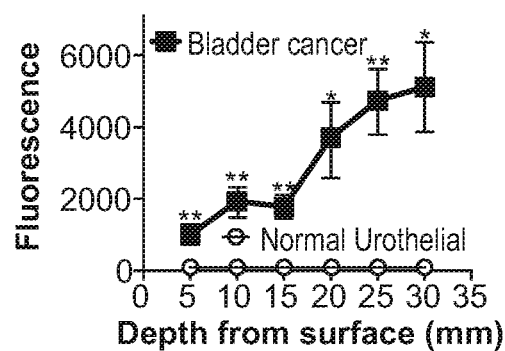
Figure 9B:
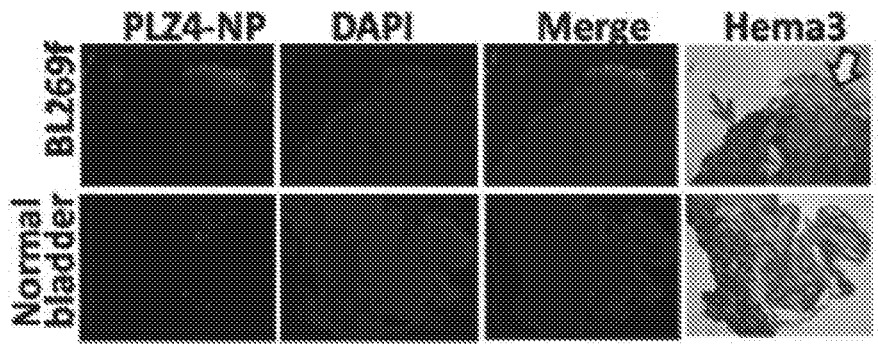
Figure 10:
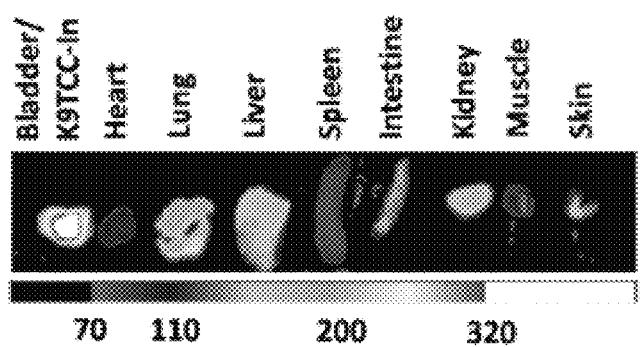
FIG. 10 shows ex vivo near infra-red imaging of tumor/bladder and organs 24 hr after iv administration of non-crosslinked PLZ4-NP.
Figure 11A:
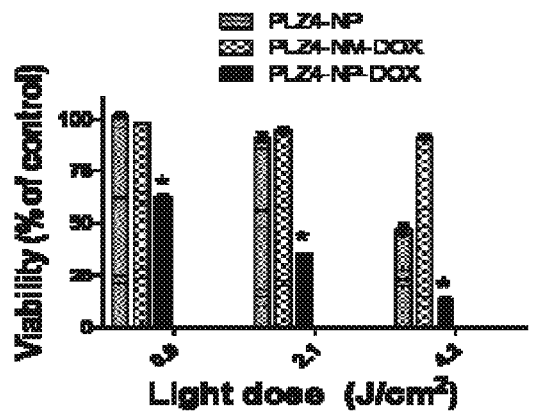
FIG. 11A-11D shows cytotoxicity effect in combination of doxorubicin with PLZ4-NP mediated PDT.
Figure 11B:
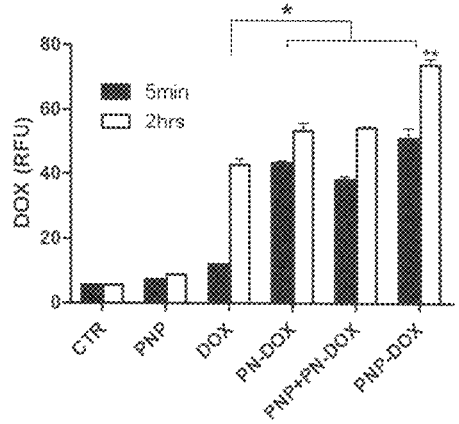
Figure 11C:
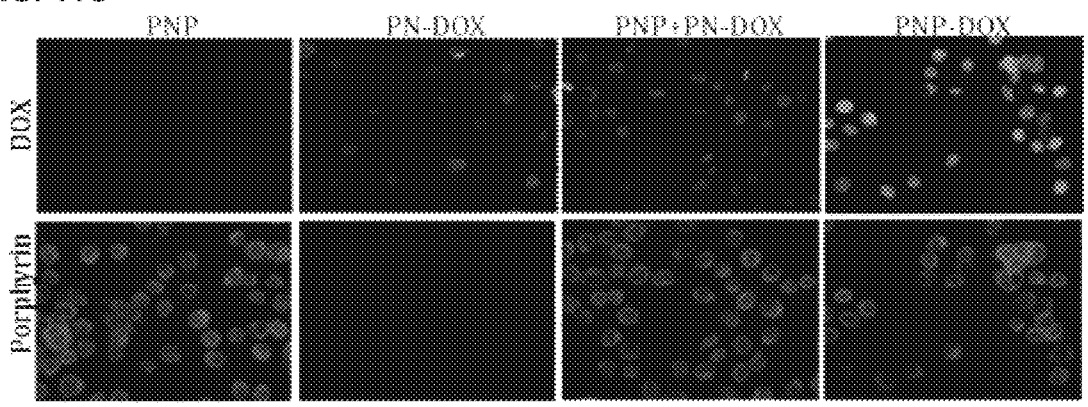
Figure 11D:
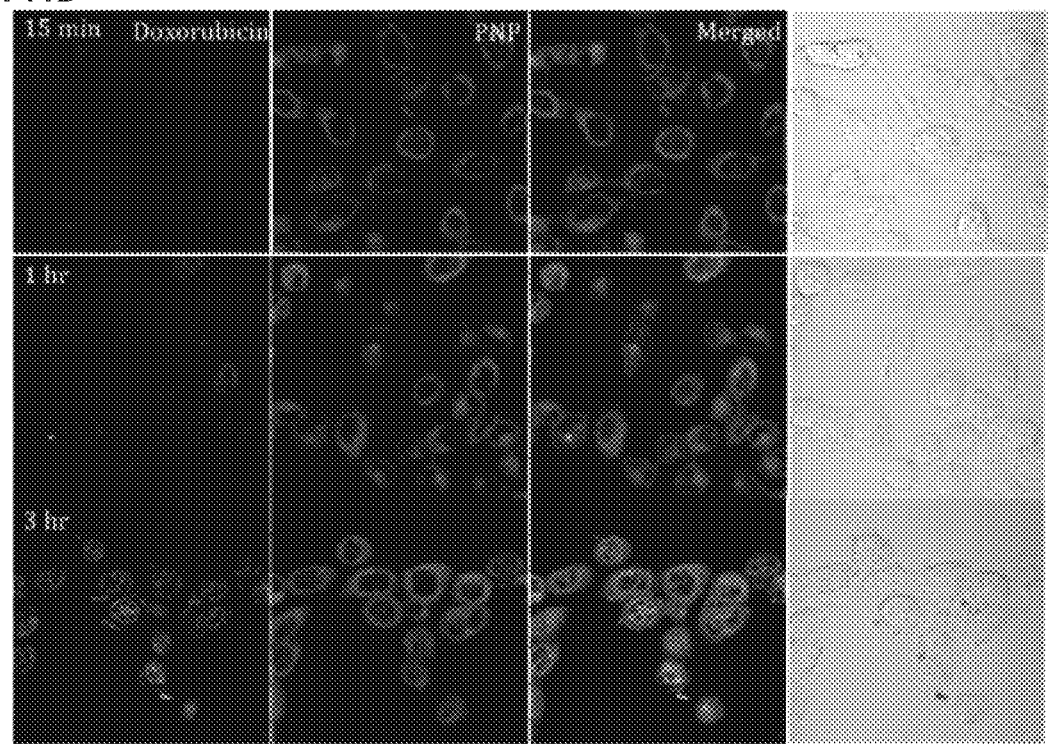

As used herein, the terms "dendrimer" and "dendritic polymer" refer to branched polymers containing a focal point, a plurality of branched monomer units, and a plurality of end groups. The monomers are linked together to form arms (or "dendrons") extending from the focal point and terminating at the end groups. The focal point of the dendrimer can be attached to other segments of the compounds of the invention, and the end groups may be further functionalized with additional chemical moieties.

As used herein, the term "telodendrimer" refers to a dendrimer containing a hydrophilic PEG segment and one or more chemical moieties covalently bonded to one or more end groups of the dendrimer. These moieties can include, but are not limited to, hydrophobic groups, hydrophilic groups, amphiphilic compounds, and drugs. Different moieties may be selectively installed at a desired end groups using orthogonal protecting group strategies.

As used herein, the term "nanocarrier" refers to a micelle resulting from aggregation of the dendrimer conjugates of the invention. The nanocarrier has a hydrophobic core and a hydrophilic exterior.

As used herein, the terms "monomer" and "monomer unit" refer to a diamino carboxylic acid, a dihydroxy carboxylic acid and a hydroxyl amino carboxylic acid. Examples of diamino carboxylic acid groups of the present invention include, but are not limited to, 2,3-diamino propanoic acid, 2,4-diaminobutanoic acid, 2,5-diaminopentanoic acid (ornithine), 2,6-diaminohexanoic acid (lysine), (2-Aminoethyl)-cysteine, 3-amino-2-aminomethyl propanoic acid, 3-amino-2-aminomethyl-2-methyl propanoic acid, 4-amino-2-(2-aminoethyl) butyric acid and 5-amino-2-(3-aminopropyl) pentanoic acid. Examples of dihydroxy carboxylic acid groups of the present invention include, but are not limited to, glyceric acid, 2,4-dihydroxybutyric acid, glyceric acid, 2,4-dihydroxybutyric acid, 2,2-Bis(hydroxymethyl)propionic acid and 2,2-Bis(hydroxymethyl) butyric acid. Examples of hydroxyl amino carboxylic acids include, but are not limited to, serine and homoserine. One of skill in the art will appreciate that other monomer units are useful in the present invention.

As used herein, the term "amino acid" refers to a carboxylic acid bearing an amine functional groups. Amino acids include the diamino carboxylic acids described above. Amino acids include naturally occurring α-amino acids, wherein the amine is bound to the carbon adjacent to the carbonyl carbon of the carboxylic acid. Examples of naturally occurring α-amino acids include, but are not limited to, L-aspartic acid, L-glutamic acid, L-histidine, L-lysine, and L-arginine. Amino acids may also include the D-enantiomers of naturally occurring α-amino acids, as well as β-amino acids and other non-naturally occurring amino acids.

As used herein, the term "linker" refers to a chemical moiety that links one segment of a dendrimer conjugate to another. The types of bonds used to link the linker to the segments of the dendrimers include, but are not limited to, amides, amines, esters, carbamates, ureas, thioethers, thiocarbamates, thiocarbonate and thioureas. One of skill in the art will appreciate that other types of bonds are useful in the present invention.

As used herein, the term "oligomer" refers to five or fewer monomers, as described above, covalently linked together. The monomers may be linked together in a linear or branched fashion. The oligomer may function as a focal point for a branched segment of a telodendrimer.

As used herein, the term "hydrophobic group" refers to a chemical moiety that is water-insoluble or repelled by water. Examples of hydrophobic groups include, but are not limited to, long-chain alkanes and fatty acids, fluorocarbons, silicones, certain steroids such as cholesterol, and many polymers including, for example, polystyrene and polyisoprene.

As used herein, the term "hydrophilic group" refers to a chemical moiety that is water-soluble or attracted to water. Examples of hydrophilic groups include, but are not limited to, alcohols, short-chain carboxylic acids, quaternary amines, sulfonates, phosphates, sugars, and certain polymers such as PEG.

As used herein, the term "amphiphilic compound" refers to a compound having both hydrophobic portions and hydrophilic portions. For example, the amphiphilic compounds of the present invention can have one hydrophilic face of the compound and one hydrophobic face of the compound. Amphiphilic compounds useful in the present invention include, but are not limited to, cholic acid and cholic acid analogs and derivatives.

As used herein, the term "cholic acid" refers to (R)-4-((3R, 5S, 7R, 8R, 9S, 10S, 12S, 13R, 14S, 17R)-3,7,12-trihydroxy-10,13-dimethylhexadecahydro-1H-cyclopenta[a]phenanthren-17-yl)pentanoic acid. Cholic acid is also know as 3α,7α,12α-trihydroxy-5β-cholanoic acid; 3-α,7-α,12-α-Trihydroxy-5-β-cholan-24-oic acid; 17-β-(1-methyl-3-carboxypropyl)etiocholane-3α,7α,12α-triol; cholalic acid; and cholalin. Cholic acid derivatives and analogs, such as allocholic acid, pythocholic acid, avicholic acid, deoxycholic acid, chenodeoxycholic acid, are also useful in the present invention. Cholic acid derivatives can be designed to modulate the properties of the nanocarriers resulting from telodendrimer assembly, such as micelle stability and membrane activity. For example, the cholic acid derivatives can have hydrophilic faces that are modified with one or more glycerol groups, aminopropanediol groups, or other groups.

As used herein, the terms "drug" or "therapeutic agent" refers to an agent capable of treating and/or ameliorating a condition or disease. A drug may be a hydrophobic drug, which is any drug that repels water. Hydrophobic drugs useful in the present invention include, but are not limited to, paclitaxel, doxorubicin, etoposide, irinotecan, SN-38, cyclosporin A, podophyllotoxin, Carmustine, Amphotericin, Ixabepilone, Patupilone (epothelone class), rapamycin and platinum drugs. The drugs of the present invention also include prodrug forms. One of skill in the art will appreciate that other drugs are useful in the present invention.

As used herein, the term "crosslinkable group" or "crosslinking group" refers to a functional group capable of binding to a similar or complementary group on another molecule, for example, a first crosslinkable group on a first dendritic polymer linking to a second crosslinkable group on a second dendritic polymer. Groups suitable as crosslinkable and crosslinking groups in the present invention include thiols such as cysteine, boronic acids and 1,2-diols including 1,2-dihydroxybenzenes such as catechol. When the crosslinkable and crosslinking groups combine, they form crosslinked bonds such as disulfides and boronic esters. Other crosslinkable and crosslinking groups are suitable in the present invention.

As used herein, the term "bond cleavage component" refers to an agent capable of cleaving the cross-linked bonds formed using the crosslinkable and crosslinking groups of the present invention. The bond cleavage component can be a reducing agent, such as glutathione, when the cross-linked bond is a disulfide, or mannitol when the cross-linked bond is formed from a boronic acid and 1,2-diol.

As used herein, the term "imaging agent" refers to chemicals that allow body organs, tissue or systems to be imaged. Exemplary imaging agents include paramagnetic agents, optical probes, and radionuclides.

As used herein, the terms "treat", "treating" and "treatment" refers to any indicia of success in the treatment or amelioration of an injury, pathology, condition, or symptom (e.g., pain), including any objective or subjective parameter such as abatement; remission; diminishing of symptoms or making the symptom, injury, pathology or condition more tolerable to the patient; decreasing the frequency or duration of the symptom or condition; or, in some situations, preventing the onset of the symptom or condition. The treatment or amelioration of symptoms can be based on any objective or subjective parameter; including, e.g., the result of a physical examination.

As used herein, the term "subject" refers to animals such as mammals, including, but not limited to, primates (e.g., humans), cows, sheep, goats, horses, dogs, cats, rabbits, rats, mice and the like. In certain embodiments, the subject is a human.

As used herein, the terms "therapeutically effective amount or dose" or "therapeutically sufficient amount or dose" or "effective or sufficient amount or dose" refer to a dose that produces therapeutic effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins). In sensitized cells, the therapeutically effective dose can often be lower than the conventional therapeutically effective dose for non-sensitized cells.

As used herein, the term "photodynamic therapy" refers to use of nontoxic, light-sensitive compounds that become toxic to malignant or disease cells upon exposure to light. Photodynamic therapy involves a photosensitizer, a light source, and oxygen. Upon exposure to the light, the photosensitizer generates reactive oxygen species (singlet oxygen, an oxygen free radical) that react with and destroy the malignant tissue. A variety of photosensitizers can be used, including porphyrins, chlorophylls and dyes.

As used herein, the term "photothermal therapy" refers to use of nontoxic, light-sensitive compounds that generate heat upon exposure to light. Like photodynamic therapy, photothermal therapy involves a photosensitizer and a source of light, typically infrared. But photothermal therapy does not require oxygen. A variety of photosensitizers can be used, including porphyrins, chlorophylls and dyes.

II. Telodendrimers

The invention provides amphiphilic telodendrimer conjugates having a hydrophilic poly(ethylene glycol) (PEG) segment and a hydrophobic segment, and at least one porphyrin. The PEG segment can have a branched or linear architecture including one or more PEG chains. The hydrophobic segment of the telodendrimer can be provided by cholic acid, which has a hydrophobic face and a hydrophilic face. The porphyrin, cholic acid and the PEG are connected by oligomers and/or polymers that can contain a variety of acid repeats units. Typically, the oligomers and polymers comprise a diamino carboxylic acid, lysine. The telodendrimers can aggregate in solution to form micelles with a hydrophobic interior and a hydrophilic exterior. The micelles can be used as nanocarriers to deliver drugs or other agents having low water solubility.

In some embodiments, the present invention provides conjugates having a polyethylene glycol (PEG) polymer; at least two amphiphilic compounds having both a hydrophilic face and a hydrophobic face; at least one porphyrin; optionally at least two crosslinking groups; and a dendritic polymer covalently attached to the PEG, the amphiphilic compounds, the porphyrin and the crosslinking groups, wherein each conjugate self-assembles in an aqueous solvent to form the nanocarrier such that a hydrophobic pocket is formed in the interior of the nanocarrier by the orientation of the hydrophobic face of each amphiphilic compound towards each other, wherein the PEG of each conjugate self-assembles on the exterior of the nanocarrier.

In some embodiments, the present invention provides a compound of formula I:

$$(B)_k\text{-}(PEG)_m\text{-}A(Y^1)_p\text{-}L^1\text{-}D\text{-}[Y^2\text{-}L^2\text{-}R]_n \quad (I)$$

wherein B can be a binding ligand; each PEG can be a polyethyleneglycol (PEG) polymer having a molecular weight of 1-100 kDa; A includes at least one branched monomer unit X and can be linked to at least one PEG group; D can be a dendritic polymer having a single focal point group, a plurality of branched monomer units X and a plurality of end groups; each $Y^1$ and $Y^2$ can be absent or a crosslinkable group that can be boronic acid, dihydroxybenzene or a thiol; each $L^1$ and $L^2$ can independently be a bond or a linker, wherein $L^1$ can be linked to the focal point group of the dendritic polymer; each R can independently be the end group of the dendritic polymer, a porphyrin, a hydrophobic group, a hydrophilic group, an amphiphilic compound or a drug, wherein at least one R group can be a porphyrin; subscript k can be 0 or 1; subscript m can be an integer from 0 to 20; subscript n can be an integer from 2 to 20, wherein subscript n can be equal to the number of end groups on the dendritic polymer; and subscript p can be from 0 to 8.

Any suitable binding ligand can be used in the compounds of the present invention. For example, the binding ligand can target a particular organ, healthy tissue or disease tissue. Exemplary binding ligands include the PLZ4 ligand, having the amino acid sequence QDGRMGF. See U.S. application Ser. No. 13/497,041, filed Sep. 23, 2010, now U.S. Publication No. 2012/0230994.

The linkers $L^1$ and $L^2$ can include any suitable linker. In general, the linkers are bifunctional linkers, having two functional groups for reaction with each of two telodendrimer segments. In some embodiments, the linkers $L^1$ and $L^2$ can be a heterobifunctional linker. In some embodiments, the linkers $L^1$ and $L^2$ can be a homobifunctional linker. In some embodiments, the linkers $L^1$ and $L^2$ can independently be polyethylene glycol, polyserine, polyglycine, poly(serine-glycine), aliphatic amino acids, 6-amino hexanoic acid, 5-amino pentanoic acid, 4-amino butanoic acid or beta-alanine. One of skill in the art will recognize that the size and chemical nature of the linker can be varied based on the structures of the telodendrimer segments to be linked.

In some embodiments, linkers $L^1$ and $L^2$ can have the formula:

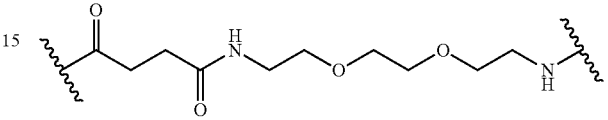

Polyethylene glycol (PEG) polymers of any size and architecture are useful in the nanocarriers of the present invention. In some embodiments, the PEG is from 1-100 kDa. In other embodiments, the PEG is from 1-10 kDa. In some other embodiments, the PEG is about 3 kDa. In still other embodiments, additional PEG polymers are linked to the amphiphilic compounds. For example, when the amphiphilic compound is cholic acid, up to 3 PEG polymers are linked to each cholic acid. The PEG polymers linked to the amphiphilic compounds are from 200-10,000 Da in size. In yet other embodiments, the PEG polymers linked to the amphiphilic compounds are from 1-5 kDa in size. One of skill in the art will appreciate that other PEG polymers and other hydrophilic polymers are useful in the present invention. PEG can be any suitable length.

The dendritic polymer can be any suitable dendritic polymer. The dendritic polymer can be made of branched monomer units including amino acids or other bifunctional AB2-type monomers, where A and B are two different functional groups capable of reacting together such that the resulting polymer chain has a branch point where an A-B bond is formed. In some embodiments, each branched monomer unit X can be a diamino carboxylic acid, a dihydroxy carboxylic acid and a hydroxyl amino carboxylic acid. In some embodiments, each diamino carboxylic acid can be 2,3-diamino propanoic acid, 2,4-diaminobutanoic acid, 2,5-diaminopentanoic acid (ornithine), 2,6-diaminohexanoic acid (lysine), (2-Aminoethyl)-cysteine, 3-amino-2-aminomethyl propanoic acid, 3-amino-2-aminomethyl-2-methyl propanoic acid, 4-amino-2-(2-aminoethyl) butyric acid or 5-amino-2-(3-aminopropyl) pentanoic acid. In some embodiments, each dihydroxy carboxylic acid can be glyceric acid, 2,4-dihydroxybutyric acid, 2,2-Bis(hydroxymethyl)propionic acid, 2,2-Bis(hydroxymethyl)butyric acid, serine or threonine. In some embodiments, each hydroxyl amino carboxylic acid can be serine or homoserine. In some embodiments, the diamino carboxylic acid is an amino acid. In some embodiments, each branched monomer unit X is lysine.

The dendritic polymer of the telodendrimer can be any suitable generation of dendrimer, including generation 1, 2, 3, 4, 5, or more, where each "generation" of dendrimer refers to the number of branch points encountered between the focal point and the end group following one branch of the dendrimer. The dendritic polymer of the telodendrimer can also include partial-generations such as 1.5, 2.5, 3.5, 4.5, 5.5, etc., where a branch point of the dendrimer has only a single branch. See, for example, the structures in FIG. 1. The various architectures of the dendritic polymer can provide any suitable number of end groups, including, but not limited to, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 or 32 end groups.

The focal point of a telodendrimer or a telodendrimer segment can be any suitable functional group. In some embodiments, the focal point includes a functional group that allows for attachment of the telodendrimer or telodendrimer segment to another segment. The focal point functional group can be a nucleophilic group including, but not limited to, an alcohol, an amine, a thiol, or a hydrazine. The focal point functional group may also be an electrophile such as an aldehyde, a carboxylic acid, or a carboxylic acid derivative including an acid chloride or an N-hydroxysuccinimidyl ester.

The R groups installed at the telodendrimer periphery can be any suitable chemical moiety, including porphyrins, hydrophilic groups, hydrophobic groups, or amphiphilic compounds, wherein at least one R group can be a porphyrin. Any suitable porphyrin can be used in the telodendrimers of the present invention. Representative porphyrins suitable in the present invention include, but are not limited to, pyropheophorbide-a, pheophorbide, chlorin e6, purpurin or purpurinimide. In some embodiments, the porphyrin can be pyropheophorbide-a. Representative structures are shown below:

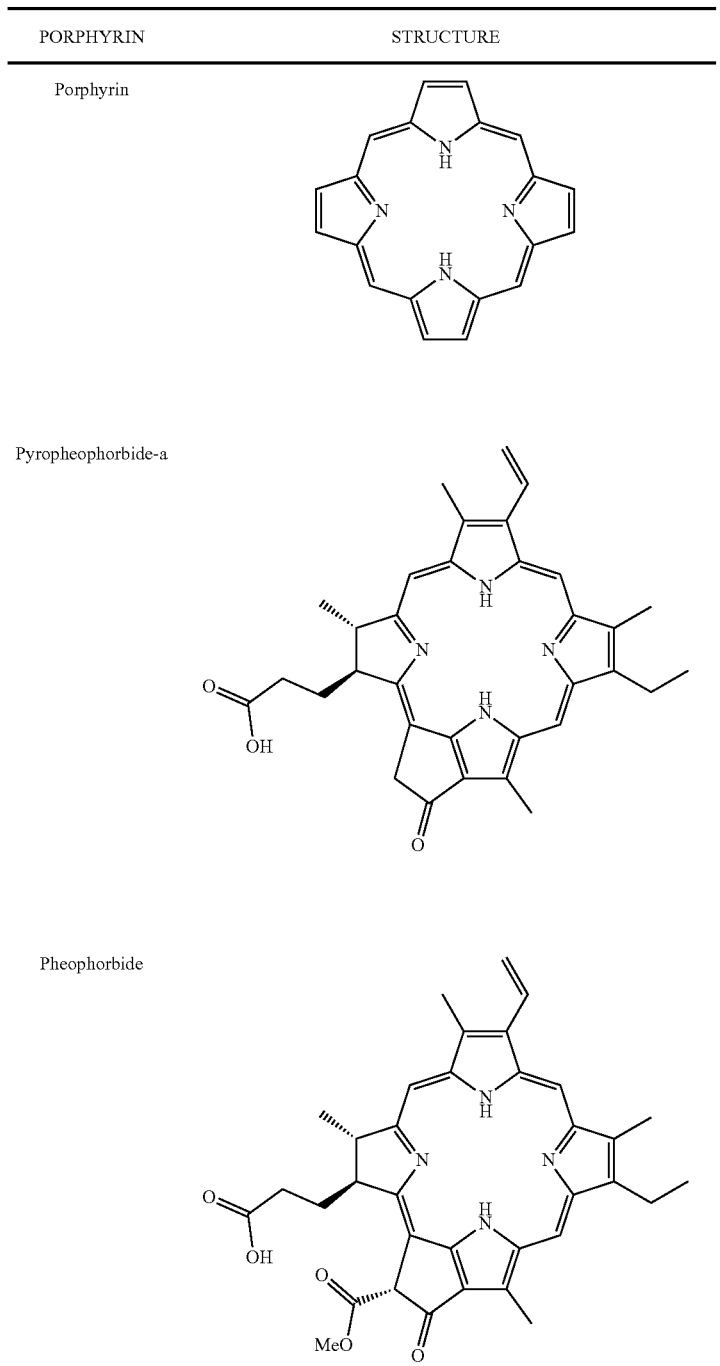

| PORPHYRIN | STRUCTURE |
|---|---|
| Chlorin e6 | 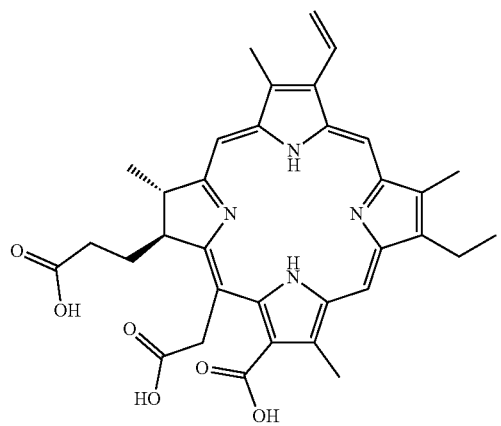 [SMILES: C=Cc1c(C)c2cc3nc(c(CC(=O)O)c4[nH]c(cc5nc(cc1[nH]2)C(C)=C5CC)c(C)c4C(=O)O)[C@@H](CCC(=O)O)[C@@H]3C] |
| Purpurin | 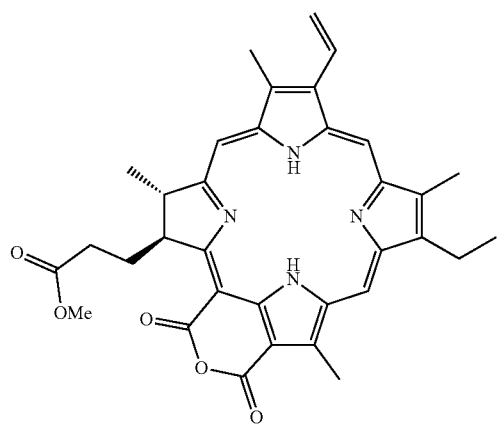 [SMILES: C=Cc1c(C)c2cc3nc(c4c5[nH]c(cc6nc(cc1[nH]2)C(C)=C6CC)c(C)c5C(=O)OC4=O)[C@@H](CCC(=O)OC)[C@@H]3C] |
| Purpurinimide | 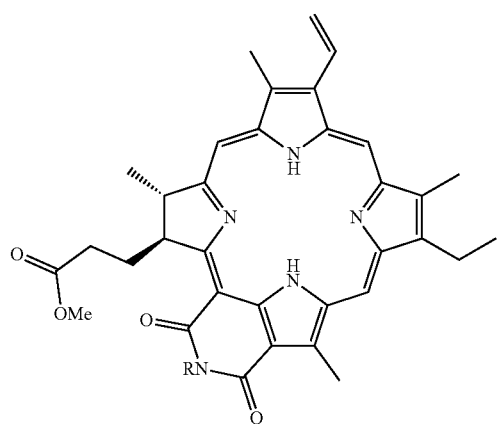 |

Examples of hydrophobic groups include, but are not limited to, long-chain alkanes and fatty acids, fluorocarbons, silicones, certain steroids such as cholesterol, and many polymers including, for example, polystyrene and polyisoprene. Examples of hydrophilic groups include, but are not limited to, alcohols, short-chain carboxylic acids, amines, sulfonates, phosphates, sugars, and certain polymers such as PEG. Examples of amphiphilic compounds include, but are not limited to, molecules that have one hydrophilic face and one hydrophobic face.

Amphiphilic compounds useful in the present invention include, but are not limited to, cholic acid and cholic acid analogs and derivatives. "Cholic acid" refers to (R)-4-((3R, 5S, 7R, 8R, 9S, 10S, 12S, 13R, 14S, 17R)-3,7,12-trihydroxy-10,13-dimethylhexadecahydro-1H-cyclopenta[a]
phenanthren-17-yl)pentanoic acid, having the structure:

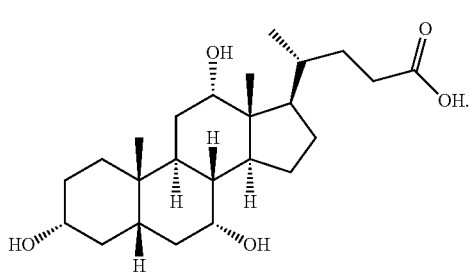

Cholic acid derivatives and analogs include, but are not limited to, allocholic acid, pythocholic acid, avicholic acid, deoxycholic acid, and chenodeoxycholic acid. Cholic acid derivatives can be designed to modulate the properties of the nanocarriers resulting from telodendrimer assembly, such as micelle stability and membrane activity. For example, the cholic acid derivatives can have hydrophilic faces that are modified with one or more glycerol groups, aminopropane-diol groups, or other groups.

Telodendrimer end groups may also include drugs such as paclitaxel, doxorubicin, etoposide, irinotecan, SN-38, cyclosporin A, podophyllotoxin, carmustine, amphotericin, ixabepilone, patupilone (epothelone class), rapamycin and platinum drugs. One of skill in the art will appreciate that other drugs are useful in the present invention.

In some embodiments, each remaining R can be cholic acid, (3α, 5β, 7α, 12α)-7,12-dihydroxy-3-(2,3-dihydroxy-1-propoxy)-cholic acid, (3α, 5β, 7α, 12α)-7-hydroxy-3,12-di(2,3-dihydroxy-1-propoxy)-cholic acid, (3α, 5β, 7α, 12α)-7,12-dihydroxy-3-(3-amino-2-hydroxy-1-propoxy)-cholic acid, cholesterol formate, doxorubicin, or rhein. In other embodiments, each remaining R can be cholic acid.

The telodendrimer backbone can vary, depending on the number of branches and the number and chemical nature of the end groups and R groups, which will modulate solution conformation, rheological properties, and other characteristics. The telodendrimers can have any suitable number n of end groups and any suitable number of R groups. In some embodiments, n can be 2-70, or 2-50, or 2-30, or 2-10. In some embodiment, n is 2-20.

The telodendrimer can have a single type of R group on the periphery, or any combination of R groups in any suitable ratio. In general, at least half the number n of R groups are other than an end group. For example, at least half the number n of R groups can be a hydrophobic group, a hydrophilic group, an amphiphilic compound, a drug, or any combination thereof. In some embodiments, half the number n of R groups are amphiphilic compounds.

In some embodiments, the compound has the structure:

wherein each R can independently be a porphyrin, an amphiphilic compound or a drug, wherein at least one R group is a porphyrin.

In some embodiments, the compound has the structure:

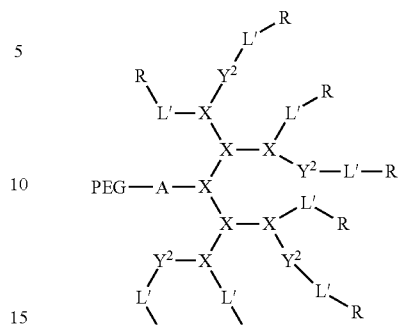

wherein PEG can be PEG5k, each branched monomer unit X can be lysine, A can be lysine, each $L^2$ can be a bond or linker Ebes, each $Y^2$ can be absent or can be cysteine; and each R can be a cholic acid or a porphyrin.

In some embodiments, the compound has the structure:

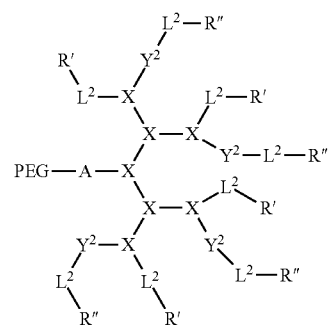

wherein each R' can be cholic acid (CA), (3α, 5β, 7α, 12α)-7,12-dihydroxy-3-(2,3-dihydroxy-1-propoxy)-cholic acid (CA-4OH), (3α, 5β, 7α, 12α)-7-hydroxy-3,12-di(2,3-dihydroxy-1-propoxy)-cholic acid (CA-5OH) or (3α, 5β, 7α, 12α)-7,12-dihydroxy-3-(3-amino-2-hydroxy-1-propoxy)-cholic acid (CA-3OH—NH$_2$); and each R" can be a porphyrin selected from the group consisting of pyropheophorbide-a, pheophorbide, chlorin e6, purpurin and purpurinimide. In other embodiments, the porphyrin can be pyropheophorbide-a. In some other embodiments, subscript k is 1. In some other embodiments, the compound can be:
(1) each $L^2$ is a bond, each $Y^2$ is absent, each R' is cholic acid, each R" is pyropheophorbide-a, and subscript k is 0;
(2) each $L^2$ is the linker Ebes, each $Y^2$ is absent, each R' is cholic acid, each R" is pyropheophorbide-a, and subscript k is 0;
(3) each $L^2$ is a bond, each $Y^2$ is cysteine, each R' is cholic acid, each R" is pyropheophorbide-a, and subscript k is 0;
(4) each $L^2$ is the linker Ebes, each $Y^2$ is cysteine, each R' is cholic acid, each R" is pyropheophorbide-a, and subscript k is 0;
(5) each $L^2$ is a bond, each $Y^2$ is absent, each R' is cholic acid, each R" is pyropheophorbide-a, and subscript k is 1;
(6) each $L^2$ is the linker Ebes, each $Y^2$ is absent, each R' is cholic acid, each R" is pyropheophorbide-a, and subscript k is 1;

(7) each L² is a bond, each Y² is cysteine, each R' is cholic acid, each R" is pyropheophorbide-a, and subscript k is 1; or (8) each L² is the linker Ebes, each Y² is cysteine, each R' is cholic acid, each R" is pyropheophorbide-a, and subscript k is 1.

In some embodiments, the compound has the structure:

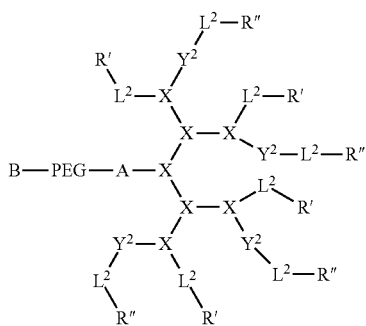

wherein each R' can be cholic acid (CA), (3α, 5β, 7α, 12α)-7,12-dihydroxy-3-(2,3-dihydroxy-1-propoxy)-cholic acid (CA-4OH), (3α, 5β, 7α, 12α)-7-hydroxy-3,12-di(2,3-dihydroxy-1-propoxy)-cholic acid (CA-5OH) or (3α, 5β, 7α, 12α)-7,12-dihydroxy-3-(3-amino-2-hydroxy-1-propoxy)-cholic acid (CA-3OH—NH₂); and each R" can be a porphyrin selected from the group consisting of pyropheophorbide-a, pheophorbide, chlorin e6, purpurin and pur-purinimide. In other embodiments, the porphyrin can be pyropheophorbide-a. In some other embodiments, subscript k is 1. In some other embodiments, the compound can be:

points. Generally, the telodendrimers include any telodendrimer as described above or as described previously (WO 2010/039496) and branched PEG segment containing two or more PEG chains bound to an oligomer focal point.

The dendritic polymer of the telodendrimer can be any suitable generation of dendrimer, including generation 1, 2, 3, 4, 5, or more, where each "generation" of dendrimer refers to the number of branch points encountered between the focal point and the end group following one branch of the dendrimer. The dendritic polymer of the telodendrimer can also include partial-generations such as 1.5, 2.5, 3.5, 4.5, 5.5, etc., where a branch point of the dendrimer has only a single branch. See, for example, the structures in FIG. 1. The various architectures of the dendritic polymer can provide any suitable number of end groups, including, but not limited to, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 or 32 end groups.

In some embodiments, the compound can be:

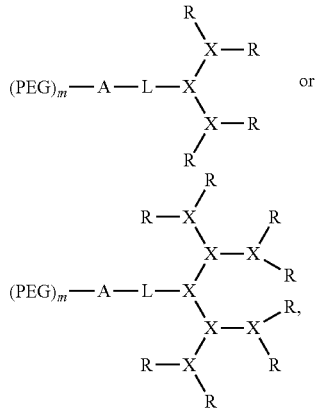

wherein each branched monomer unit X is lysine.

| Compound | B | PEG (mw) | A | X | L² | Y² | R' | R" |
|---|---|---|---|---|---|---|---|---|
| 1 | absent | 5 k | lysine | lysine | bond | absent | cholic acid | pyropheophorbide-a |
| 2 | absent | 5 k | lysine | lysine | Ebes | absent | cholic acid | pyropheophorbide-a |
| 3 | absent | 5 k | lysine | lysine | bond | cysteine | cholic acid | pyropheophorbide-a |
| 4 | absent | 5 k | lysine | lysine | Ebes | cysteine | cholic acid | pyropheophorbide-a |
| 5 | PLZ4 | 5 k | lysine | lysine | bond | absent | cholic acid | pyropheophorbide-a |
| 6 | PLZ4 | 5 k | lysine | lysine | Ebes | absent | cholic acid | pyropheophorbide-a |
| 7 | PLZ4 | 5 k | lysine | lysine | bond | cysteine | cholic acid | pyropheophorbide-a |
| 8 | PLZ4 | 5 k | lysine | lysine | Ebes | cysteine | cholic acid | pyropheophorbide-a |

The compounds of the present invention can also include a metal cation chelated to the porphyrin. Any suitable metal can be chelated by the porphyrin. Metals useful in the present invention include the alkali metals, alkali earth metals, transition metals and post-transition metals. Alkali metals include Li, Na, K, Rb and Cs. Alkaline earth metals include Be, Mg, Ca, Sr and Ba. Transition metals include Sc, Ti, V, Cr, Mn, Fe, Co, Ni, Cu, Zn, Y, Zr, Nb, Mo, Tc, Ru, Rh, Pd, Ag, Cd, La, Hf, Ta, W, Re, Os, Ir, Pt, Au, Hg and Ac. Post-transition metals include Al, Ga, In, Tl, Ge, Sn, Pb, Sb, Bi, and Po. Radionuclides of any of these metals can also be chelated by the porphyrins. In some embodiments, the a metal cation can be chelated to the porphyrin. In other embodiments, the metal cation can be a radio-metal cation. In some other embodiments, the radio-metal cation chelated to the porphyrin can be $^{64}$Cu, $^{67}$Cu, $^{177}$Lu, $^{67}$Ga, $^{111}$In, and $^{90}$Yt.

III. Telodendrimers with Branched PEG Moieties

The telodendrimers of the present invention contain two branched segments that are linked together at their focal In some embodiments, the compound can be:

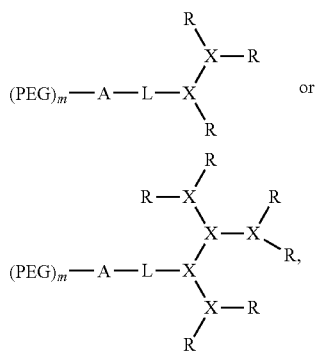

wherein each branched monomer unit X is lysine.

The PEG-oligomer unit in the telodendrimers may contain any suitable number of PEG moieties. PEG moieties may be installed site-selectively at various positions on the oligomer using orthogonal protecting groups. In some embodiments, the $(PEG)_m$-A portion of the compound can be:

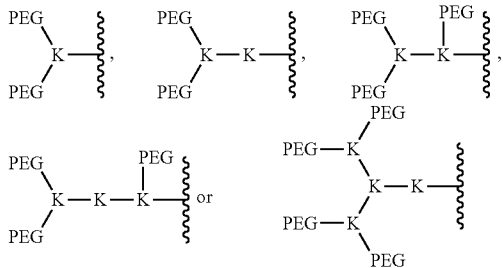

wherein each K is lysine.

In some embodiments, the telodendrimer can be:

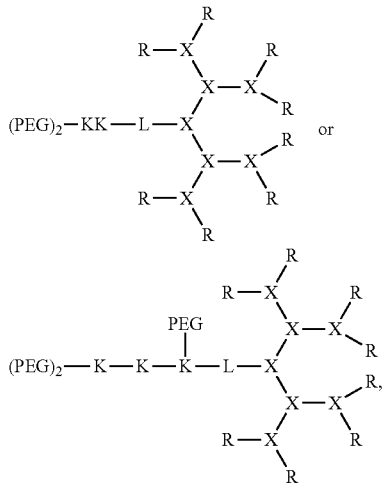

wherein each K is lysine; each PEG is PEG2k; each branched monomer unit X is lysine; each R is cholic acid; and linker L has the formula:

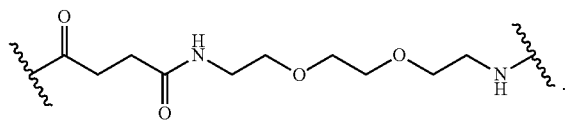

IV. Nanocarriers

The telodendrimers of the present invention aggregate to form nanocarriers with a hydrophobic core and a hydrophilic exterior. In some embodiments, the invention provides a nanocarrier having an interior and an exterior, the nanocarrier comprising a plurality of the dendrimer conjugates of the invention, wherein each compound self-assembles in an aqueous solvent to form the nanocarrier such that a hydrophobic pocket is formed in the interior of the nanocarrier, and wherein the PEG of each compound self-assembles on the exterior of the nanocarrier.

In some embodiments, each conjugate of the nanocarrier have a polyethylene glycol (PEG) polymer; at least two amphiphilic compounds having both a hydrophilic face and a hydrophobic face; at least one porphyrin; optionally at least two crosslinking groups; and a dendritic polymer covalently attached to the PEG, the amphiphilic compounds, the porphyrin and the crosslinking groups, wherein each conjugate self-assembles in an aqueous solvent to form the nanocarrier such that a hydrophobic pocket is formed in the interior of the nanocarrier by the orientation of the hydrophobic face of each amphiphilic compound towards each other, wherein the PEG of each conjugate self-assembles on the exterior of the nanocarrier. In other embodiments, each conjugate is a compound of formula I.

In some embodiments, the nanocarrier includes a hydrophobic drug or an imaging agent, such that the hydrophobic drug or imaging agent is sequestered in the hydrophobic pocket of the nanocarrier. Hydrophobic drugs useful in the nanocarrier of the present invention includes any drug having low water solubility. In some embodiments, the hydrophobic drug in the nanocarrier can be bortezomib, paclitaxel, SN38, camptothecin, etoposide and doxorubicin, docetaxel, daunorubicin, VP16, prednisone, dexamethasone, vincristine, vinblastine, temsirolimus and carmusine.

In some embodiments, the nanocarrier includes at least one monomer unit that is optionally linked to an optical probe, a radionuclide, a paramagnetic agent, a metal chelate or a drug. The drug can be a variety of hydrophilic or hydrophobic drugs, and is not limited to the hydrophobic drugs that are sequestered in the interior of the nanocarriers of the present invention.

Drugs that can be sequestered in the nanocarriers or linked to the conjugates of the present invention include, but are not limited to, cytostatic agents, cytotoxic agents (such as for example, but not limited to, DNA interactive agents (such as cisplatin or doxorubicin)); taxanes (e.g. taxotere, taxol); topoisomerase II inhibitors (such as etoposide); topoisomerase I inhibitors (such as irinotecan (or CPT-11), camptostar, or topotecan); tubulin interacting agents (such as paclitaxel, docetaxel or the epothilones); hormonal agents (such as tamoxifen); thymidilate synthase inhibitors (such as 5-fluorouracil); anti-metabolites (such as methotrexate); alkylating agents (such as temozolomide (TEMODAR™ from Schering-Plough Corporation, Kenilworth, N.J.), cyclophosphamide); aromatase combinations; ara-C, adriamycin, cytoxan, and gemcitabine. Other drugs useful in the nanocarrier of the present invention include but are not limited to Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, oxaliplatin (ELOXATIN™ from Sanofi-Synthelabo Pharmaceuticals, France), Pentostatine, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17.alpha.-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, or Hexamethylmelamine. Prodrug forms are also useful in the present invention.

Other drugs useful in the present invention also include radionuclides, such as $^{67}Cu$, $^{90}Y$, $^{123}I$, $^{125}I$, $^{131}I$, $^{177}Lu$, $^{188}Re$, $^{186}Re$ and $^{211}At$. In some embodiments, a radionuclide can act therapeutically as a drug and as an imaging agent.

Imaging agents include paramagnetic agents, optical probes and radionuclides.

Paramagnetic agents include iron particles, such as iron nanoparticles that are sequestered in the hydrophobic pocket of the nanocarrier.

In some embodiments, the conjugates can be crosslinked via the crosslinking groups. The crosslinking groups can be any suitable crosslinking group, as described above. In some embodiments, the crosslinking groups can be thiol, boronic acid or dihydroxybenzene. In some embodiments, the crosslinking groups can be thiol. In some embodiments, a first set of conjugates includes boronic acid crosslinking groups, and a second set of conjugates includes dihydroxybenzene crosslinking groups. In some embodiments, each conjugate of the nanocarrier includes at least two cholic acids, at least two pryopheophorbide-a groups, and at least two crosslinking groups, wherein the conjugates of the nanocarrier are crosslinked via the crosslinking groups.

The nanocarriers can include any suitable porphrying, as described above. In some embodiments, the porphyrin can be pyrpheophorbide-a. In some embodiments, the porphyrin groups can be chelated to a metal, as described above. Any suitable metal can be chelated to the porphyrins, including radioactive and non-radioactive metals, as described above. In some embodiments, the nanocarriers include a metal chelated to at least one of the pyropheophorbide-a groups.

Some embodiments of the invention provide nanocarriers wherein each amphiphilic compound R is independently cholic acid, allocholic acid, pythocholic acid, avicholic acid, deoxycholic acid, or chenodeoxycholic acid.

The nanocarriers of the present invention can also include a binding ligand for binding to a target moiety. The binding ligand can be linked to one of the conjugates of the nanocarrier, or can be separate. Any suitable binding ligand can be used in the compounds of the present invention, as described above. For example, the binding ligand can target a particular organ, healthy tissue or disease tissue. Exemplary binding ligands include the PLZ4 ligand, having the amino acid sequence cQDGRMGFc. In some embodiments, the nanocarrier including at least one binding conjugate including a polyethylene glycol (PEG) polymer, a binding ligand linked to the PEG polymer, at least two amphiphilic compounds having both a hydrophilic face and a hydrophobic face, a dendritic polymer covalently attached to the PEG and the amphiphilic compounds, wherein each binding conjugate self-assembles with the first conjugates in an aqueous solvent to form the nanocarrier such that a hydrophobic pocket is formed in the interior of the nanocarrier by the orientation of the hydrophobic face of each amphiphilic compound towards each other, wherein the PEG of each conjugate self-assembles on the exterior of the nanocarrier.

V. Method of Treating

The nanocarriers of the present invention can be used to treat any disease requiring the administration of a drug, such as by sequestering a hydrophobic drug in the interior of the nanocarrier, or by covalent attachment of a drug to a conjugate of the nanocarrier. The nanocarriers can also be used for imaging, by sequestering an imaging agent in the interior of the nanocarrier, or by attaching the imaging agent to a conjugate of the nanocarrier.

In some embodiments, the present invention provides a method of treating a disease, including administering to a subject in need of such treatment, a therapeutically effective amount of a nanocarrier of the present invention, wherein the nanocarrier includes a drug. The drug can be a covalently attached to a conjugate of the nanocarrier. In some embodiments, the drug is a hydrophobic drug sequestered in the interior of the nanocarrier. In some embodiments, the nanocarrier also includes an imaging agent. The imaging agent can be a covalently attached to a conjugate of the nanocarrier, or the imaging agent can be sequestered in the interior of the nanocarrier. In some other embodiments, both a hydrophobic drug and an imaging agent are sequestered in the interior of the nanocarrier. In still other embodiments, both a drug and an imaging agent are covalently linked to a conjugate or conjugates of the nanocarrier. In yet other embodiments, the nanocarrier can also include a radionuclide.

The methods of treating using the nanocarriers of the present invention also includes treating a disease by photodynamic therapy or photothermal therapy. The methods generally involve administering a nanocarrier of the present invention to a subject, and then exposing the subject to radiation of a specific wavelength to induce the photodynamic or photothermal therapy depending on the wavelength of light. Upon exposure to the radiation or light, the porphyrins used in the nanocarriers of the present invention, either complexed to a metal or not, generate either the reactive singlet oxygen suitable for photodynamic therapy, or generate heat sufficient of photothermal therapy. In some embodiments, the present invention provides a method of treating a disease via photodynamic or photothermal therapy, including administering to a subject in need thereof, a therapeutically effective amount of a nanocarrier of the present invention, and exposing the subject to radiation, thereby treating the disease via photodynamic or photothermal therapy. In some embodiments, the method is a method of treating a disease via photodynamic therapy. In other embodiments, the method is a method of treating a disease via photothermal therapy.

In other embodiments, the present invention provides a method of treating a disease via sonodynamic therapy, including administering to a subject in need thereof, a therapeutically effective amount of a nanocarrier of the present invention, and exposing the subject to a sonic wave, thereby treating the disease via sonodynamic therapy.

The nanocarriers of the present invention can be administered to a subject for treatment, e.g., of hyperproliferative disorders including cancer such as, but not limited to: carcinomas, gliomas, mesotheliomas, melanomas, lymphomas, leukemias, adenocarcinomas, breast cancer, ovarian cancer, cervical cancer, glioblastoma, leukemia, lymphoma, prostate cancer, and Burkitt's lymphoma, head and neck cancer, colon cancer, colorectal cancer, non-small cell lung cancer, small cell lung cancer, cancer of the esophagus, stomach cancer, pancreatic cancer, hepatobiliary cancer, cancer of the gallbladder, cancer of the small intestine, rectal cancer, kidney cancer, bladder cancer, prostate cancer, penile cancer, urethral cancer, testicular cancer, cervical cancer, vaginal cancer, uterine cancer, ovarian cancer, thyroid cancer, parathyroid cancer, adrenal cancer, pancreatic endocrine cancer, carcinoid cancer, bone cancer, skin cancer, retinoblastomas, multiple myelomas, Hodgkin's lymphoma, and non-Hodgkin's lymphoma (see, CANCER: PRINCIPLES AND PRACTICE (DeVita, V. T. et al. eds 2008) for additional cancers).

Other diseases that can be treated by the nanocarriers of the present invention include: (I) inflammatory or allergic diseases such as systemic anaphylaxis or hypersensitivity responses, drug allergies, insect sting allergies; inflammatory bowel diseases, such as Crohn's disease, ulcerative colitis, ileitis and enteritis; vaginitis; psoriasis and inflammatory dermatoses such as dermatitis, eczema, atopic dermatitis, allergic contact dermatitis, urticaria; vasculitis; spondyloarthropathies; scleroderma; respiratory allergic diseases such as asthma, allergic rhinitis, hypersensitivity lung diseases, and the like, (2) autoimmune diseases, such as arthritis (rheumatoid and psoriatic), osteoarthritis, multiple sclerosis, systemic lupus erythematosus, diabetes mellitus, glomerulonephritis, and the like, (3) graft rejection (including allograft rejection and graft-v-host disease), and (4) other diseases in which undesired inflammatory responses are to be inhibited (e.g., atherosclerosis, myositis, neurological conditions such as stroke and closed-head injuries, neurodegenerative diseases, Alzheimer's disease, encephalitis, meningitis, osteoporosis, gout, hepatitis, nephritis, sepsis, sarcoidosis, conjunctivitis, otitis, chronic obstructive pulmonary disease, sinusitis and Behcet's syndrome). In some embodiments, the disease can be cancer. In other embodiments, the disease can be bladder cancer or ovarian cancer.

In addition, the nanocarriers of the present invention are useful for the treatment of infection by pathogens such as viruses, bacteria, fungi, and parasites. Other diseases can be treated using the nanocarriers of the present invention.

Any suitable conjugate or nanocarrier can be used in the methods of the present invention. In some embodiments, each conjugate of the nanocarrier includes at least two cholic acids, at least two pryopheophorbide-a groups, at least two crosslinking groups, and a metal chelated to at least one of the pyropheophorbide-a groups, wherein the conjugates of the nanocarrier are crosslinked via the crosslinking groups.

A. Formulations

The nanocarriers of the present invention can be formulated in a variety of different manners known to one of skill in the art. Pharmaceutically acceptable carriers are determined in part by the particular composition being administered, as well as by the particular method used to administer the composition. Accordingly, there are a wide variety of suitable formulations of pharmaceutical compositions of the present invention (see, e.g., *Remington's Pharmaceutical Sciences*, 20$^{th}$ ed., 2003, supra). Effective formulations include oral and nasal formulations, formulations for parenteral administration, and compositions formulated for with extended release.

Formulations suitable for oral administration can consist of (a) liquid solutions, such as an effective amount of a compound of the present invention suspended in diluents, such as water, saline or PEG 400; (b) capsules, sachets, depots or tablets, each containing a predetermined amount of the active ingredient, as liquids, solids, granules or gelatin; (c) suspensions in an appropriate liquid; (d) suitable emulsions; and (e) patches. The liquid solutions described above can be sterile solutions. The pharmaceutical forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents. Preferred pharmaceutical preparations can deliver the compounds of the invention in a sustained release formulation.

Pharmaceutical preparations useful in the present invention also include extended-release formulations. In some embodiments, extended-release formulations useful in the present invention are described in U.S. Pat. No. 6,699,508, which can be prepared according to U.S. Pat. No. 7,125,567, both patents incorporated herein by reference.

The pharmaceutical preparations are typically delivered to a mammal, including humans and non-human mammals. Non-human mammals treated using the present methods include domesticated animals (i.e., canine, feline, murine, rodentia, and lagomorpha) and agricultural animals (bovine, equine, ovine, porcine).

In practicing the methods of the present invention, the pharmaceutical compositions can be used alone, or in combination with other therapeutic or diagnostic agents.

B. Administration

The nanocarriers of the present invention can be administered as frequently as necessary, including hourly, daily, weekly or monthly. The compounds utilized in the pharmaceutical method of the invention are administered at the initial dosage of about 0.0001 mg/kg to about 1000 mg/kg daily. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied depending upon the requirements of the patient, the severity of the condition being treated, and the compound being employed. For example, dosages can be empirically determined considering the type and stage of disease diagnosed in a particular patient. The dose administered to a patient, in the context of the present invention should be sufficient to effect a beneficial therapeutic response in the patient over time. The size of the dose also will be determined by the existence, nature, and extent of any adverse side-effects that accompany the administration of a particular compound in a particular patient. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. For convenience, the total daily dosage may be divided and administered in portions during the day, if desired. Doses can be given daily, or on alternate days, as determined by the treating physician. Doses can also be given on a regular or continuous basis over longer periods of time (weeks, months or years), such as through the use of a subdermal capsule, sachet or depot, or via a patch or pump.

The pharmaceutical compositions can be administered to the patient in a variety of ways, including topically, parenterally, intravenously, intradermally, subcutaneously, intramuscularly, colonically, rectally or intraperitoneally. Preferably, the pharmaceutical compositions are administered parenterally, topically, intravenously, intramuscularly, subcutaneously, orally, or nasally, such as via inhalation.

In practicing the methods of the present invention, the pharmaceutical compositions can be used alone, or in combination with other therapeutic or diagnostic agents. The additional drugs used in the combination protocols of the present invention can be administered separately or one or more of the drugs used in the combination protocols can be administered together, such as in an admixture. Where one or more drugs are administered separately, the timing and schedule of administration of each drug can vary. The other therapeutic or diagnostic agents can be administered at the same time as the compounds of the present invention, separately or at different times.

VI. Method of Imaging

In some embodiments, the present invention provides a method of imaging, including administering to a subject to be imaged, an effective amount of a nanocarrier of the present invention, wherein the nanocarrier includes an imaging agent. In other embodiments, the method of treating and the method of imaging are accomplished simultaneously using a nanocarrier having both a drug and an imaging agent.

Exemplary imaging agents include paramagnetic agents, optical probes, and radionuclides. Paramagnetic agents imaging agents that are magnetic under an externally applied field. Examples of paramagnetic agents include, but are not limited to, iron particles including nanoparticles. Optical probes are fluorescent compounds that can be detected by excitation at one wavelength of radiation and detection at a second, different, wavelength of radiation. Optical probes useful in the present invention include, but are not limited to, Cy5.5, Alexa 680, Cy5, DiD (1,1'-dioctadecyl-3,3,3',3'-tetramethylindodicarbocyanine perchlorate) and DiR (1,1'-dioctadecyl-3,3,3',3'-tetramethylindotricarbocyanine iodide). Other optical probes include quantum dots. Radionuclides are elements that undergo radioactive decay. Radionuclides useful in the present invention include, but are not limited to, $^{3}$H, $^{11}$C, $^{13}$N, $^{18}$F, $^{19}$F, $^{60}$Ce, $^{64}$Cu, $^{67}$Cu, $^{68}$Ga, $^{82}$Rb, $^{90}$Sr, $^{90}$Y, $^{99}$Tc, $^{99m}$Tc, $^{111}$In, $^{123}$I, $^{124}$I, $^{125}$I, $^{129}$I, $^{131}$I, $^{137}$Cs, $^{177}$Lu, $^{186}$Re, $^{188}$Re, $^{211}$At, Rn, Ra, Th, U, Pu and $^{241}$Am.

The nanocarriers of the present invention can also be used to detect tumors. For example, the porphyrin groups of the nanocarriers can emit light at a second wavelength after exposure to light at a first wavelength. The emitted light of the second wavelength can then be detected by methods known in the art. The nanocarriers useful for detection of tumors can include metal chelated to the porphyrins, or not include the metal. In some embodiments, the present invention provides a method of detecting a tumor in a subject, including administering to the subject, an effective amount of a nanocarrier of the present invention, exposing the subject to radiation at a first wavelength, wherein the radiation excites porphyrins present on the nanocarrier such that the porphyrins emit radiation at a second wavelength, and detecting the radiation emitted by the excited porphyrins, thereby detecting the tumor.

VII. Examples

Materials

Monomethyl-terminated poly(ethylene glycol) monoamine (MeO-PEG-NH$_2$, M$_w$: 5000 Da) and α-amino-ω-Boc-amino poly(ethylene glycol) (Boc-NH-PEG-NH$_2$, M$_w$: 5000 Da) was purchased from Rapp Polymere (Germany). Pyropheophorbide-a was obtained from Santa Cruz Biotechnology, Inc. (Santa Cruz). Doxorubicin hydrochloride (DOX.HCl) (Novaplus) was obtained from the UC Davis Cancer Center Pharmacy. (Fmoc)lys(Boc)-OH, (Fmoc)Lys (Dde)-OH, (Fmoc)Lys(Fmoc)-OH, (Fmoc)Cys(Trt)-OH and (Fmoc)Ebes-OH were obtained from AnaSpec Inc. (San Jose, Calif.). 3,3'-dihexadecyloxacarbocyanine perchlorate (DiO) and 4, 6-diamidino-2-phenylindole (DAPI, blue) were purchased from Invitrogen. Cholic acid, MTT [3-(4,5-dimethyldiazol-2-yl)-2,5 diphenyl tetrazolium bromide], Ellman's reagent [DTNB, 5,59-dithiobis(2-nitrobenzoic acid)] and all other chemicals were purchased from Sigma-Aldrich (St. Louis).

PLZ4 (amino acid sequence: cQDGRMGFc in which upper case letters represent L-amino acids and lowercase letters represent unnatural D-cysteines used to cyclize and stabilize PLZ4) were prepared via solid phase peptide synthesis on Rink resin as described previously (Bioconjug Chem 21, 1216-1224 (2010); Biomaterials 30, 6006-6016 (2009); Urol Oncol Epub ahead of print (2012)).

Statistical analysis was performed by Student's t-test for two groups, and one-way ANOVA for multiple groups. All results were expressed as the mean±standard error (SEM) unless otherwise noted. A value of $P<0.05$ was considered statistically significant.

Example 1. Synthesis of Telodendrimer

The telodendrimers were synthesized via solution-phase condensation reactions using Meo-PEG-NH$_2$, Boc-NH-PEG-NH$_2$, lysine, cholic acid and pyropheophorbide-a as building blocks as reported previously (Bioconjug Chem 21, 1216-1224 (2010); Biomaterials 30, 6006-6016 (2009)).

To synthesize PLZ4-telodendrimers, an aqueous-phase "click chemistry" catalyzed by cuprous ion was performed to couple the alkyne group on PLZ4 peptides to the azide group at the end of PEG on our previously reported telodendrimer (PEG$^{5k}$-CA$_8$) at a molar ratio of 1:2 (PLZ4: PEG). After conjugation, no PLZ4 was detected, suggesting PLZ4 had been successfully conjugated to the telodendrimer.

Synthesis of Telodendrimers.

The porphyrin/cholic acid hybrid telodendrimers were synthesized via solution-phase condensation reactions utilizing stepwise peptide chemistry. The NPs were formed by the self-assembly of these telodendrimers via a solvent-evaporation method[11]. The telodendrimers were characterized with respect to structure and molecular weight. NPs were characterized with respect of particle size, drug loading, stability, ROS production, absorbance, fluorescence and thermal properties.

Figure 13:
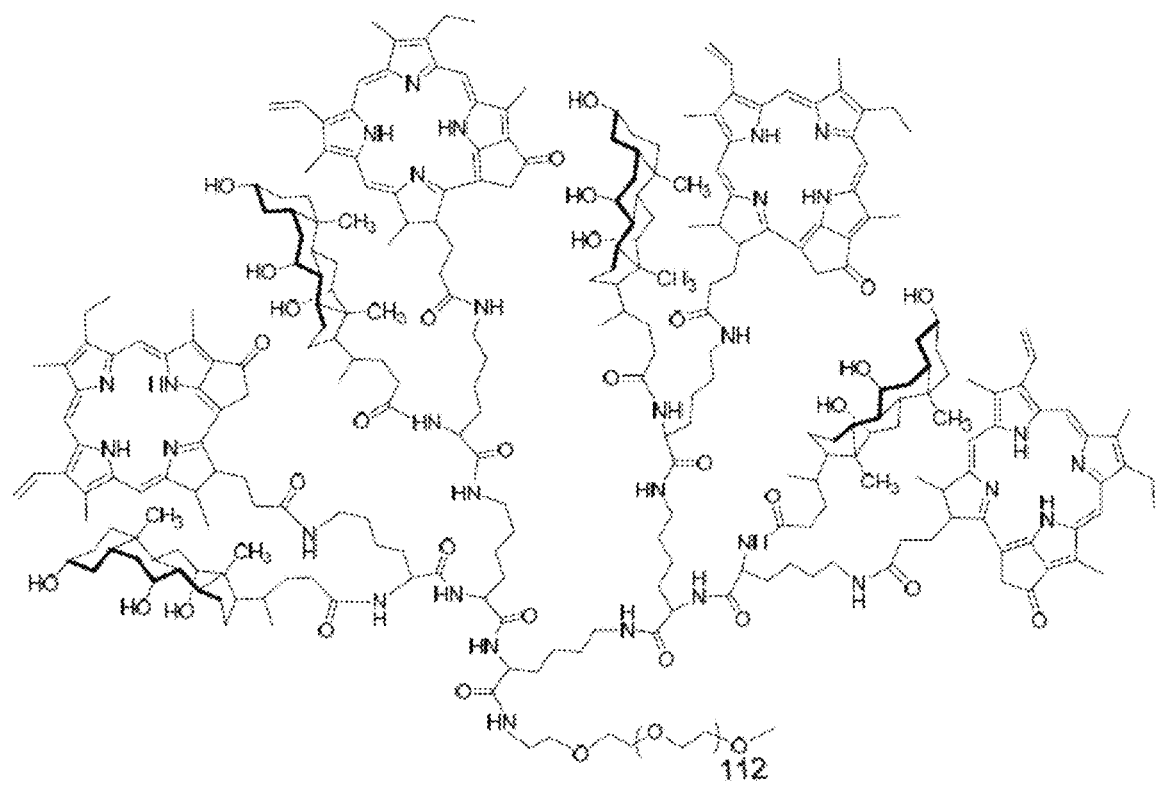
FIG. 13 shows the chemical structure of the PEG$^{5k}$-Por$_4$-CA$_4$ telodendrimer.
Figure 14:
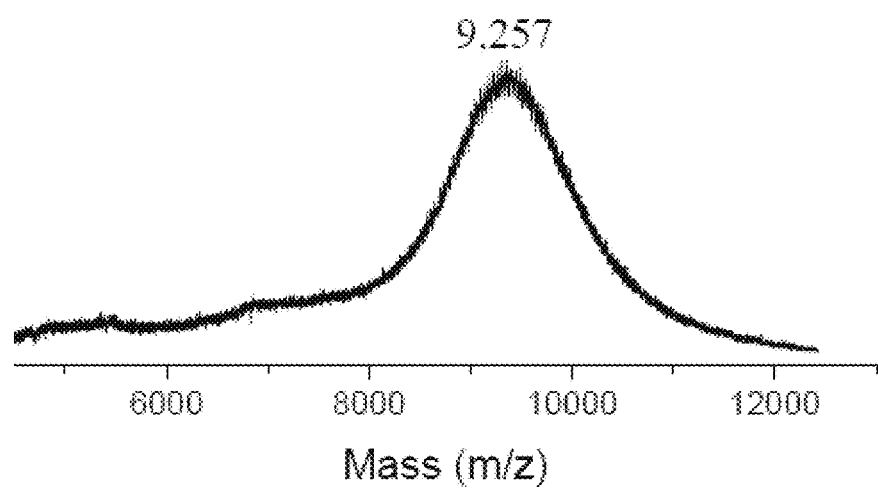
FIG. 14 shows a MALDI-TOF mass spectrum of the PEG$^{5k}$-Por$_4$-CA$_4$ telodendrimer
Figure 15:
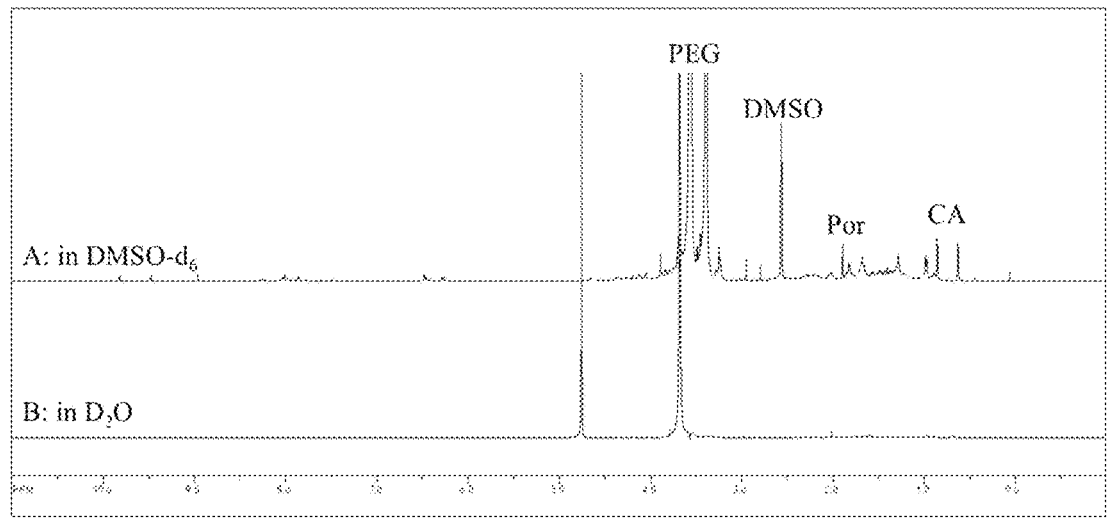
FIG. 15 shows $^1$H NMR spectra of PEG$^{5k}$-Por$_4$-CA$_4$ telodendrimer recorded in DMSO-d6 (a) and D$_2$O (b), respectively. The chemical shift of PEG chains (3.5-3.7 ppm), cholic acid (0.5-2.4 ppm) and pyropheophorbide-a (0.9-2.2 ppm) could be observed in the $^1$H NMR spectra of the telodendrimers in DMSO-d6 (a). The characteristic peaks of methyl protons 18, 19, and 21 in cholic acid were seen at 0.58, 0.80 and 0.95 ppm, respectively. The characteristic peaks of methyl protons 8 and 18 in pyropheophorbide-a were observed at 1.8 and 1.9 ppm, respectively. When the NMR spectrum was recorded in $D_2O$, the peaks of cholic acid protons and protons of pyropheophorbide-a in $PEG^{5k}$-$Por_4$-$CA_4$ were highly suppressed (b), indicating that the movements of cholanes and protons of pyropheophorbide-a were highly restricted by the formation of core-shell micellar architecture in the aqueous environment.

The representative porphyrin/cholic acid hybrid telodendrimer (PEG$^{5k}$-Por$_4$-CA$_4$, FIG. 12A, FIG. 13) was synthesized via solution-phase condensation reactions from MeO-PEG-NH$_2$ utilizing stepwise peptide chemistry. Briefly, (Fmoc)Lys(Fmoc)-OH (3 eq.) was coupled onto the N terminus of PEG using DIC and HOBt as coupling reagents until a negative Kaiser test result was obtained, thereby indicating completion of the coupling reaction. PEGylated molecules were precipitated by adding cold ether and then washed with cold ether twice. Fmoc groups were removed by the treatment with 20% (v/v) 4-methylpiperidine in dimethylformamide (DMF), and the PEGylated molecules were precipitated and washed three times by cold ether. White powder precipitate was dried under vacuum and one coupling of (Fmoc)Lys(Fmoc)-OH and one coupling of (Fmoc)lys(Boc)-OH were carried out respectively to generate a third generation of dendritic polylysine terminated with four Boc and Fmoc groups on one end of PEG. Cholic acid NHS ester and pyropheophorbide-a were coupled to the terminal end of dendritic polylysine after the removal of Fmoc with 20% (v/v) 4-methylpiperidine and the removal of Boc groups with 50% (v/v) trifluoroacetic acid (TFA) in dichloromethane (DCM), respectively. The telodendrimer solution was filtered and then dialyzed against 4 L water in a dialysis tube with MWCO of 3.5 KDa; reservoir water was refreshed completely four times in 24 h. Finally, the telodendrimer was lyophilized. The molecular weight of PEG$^{5k}$-Por$_4$-CA$_4$ was collected on ABI 4700 MALDI TOF/TOF mass spectrometer (linear mode) using R-cyano-4-hydroxycinnamic acid as a matrix. The mono-dispersed mass traces were detected for the telodendrimers, and the molecular weight of the telodendrimer from MALDI-TOF MS (FIG. 14) was almost identical to the theoretical value. $^1$H NMR spectra of the telodendrimers were recorded on an Avance 500 Nuclear Magnetic Resonance Spectrometer (Bruker) using DMSO-d6 and D2O as solvents. The concentration of the telodendrimers was kept at 5×10$^{-4}$ M for NMR measurements (FIG. 15).

Figure 16A:
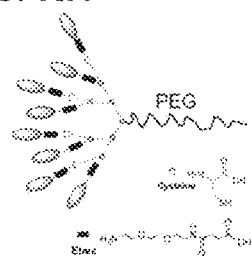
FIG. 16A-16H shows.
Figure 17A:
FIG. 17A-17B shows thermal images of NPs (10 μL) in the absence and in the presence of SDS, as monitored by a thermal camera after irradiation with NIR laser (690 nm) at 0.1 w/cm$^2$ for 120 seconds. The concentration of pyropheophorbide-a was kept at the 0.2 mg/mL for NM-POR, which was equal to the concentration of pyropheophorbide-a in 1.0 mg/mL of NPs.
Figure 17B:
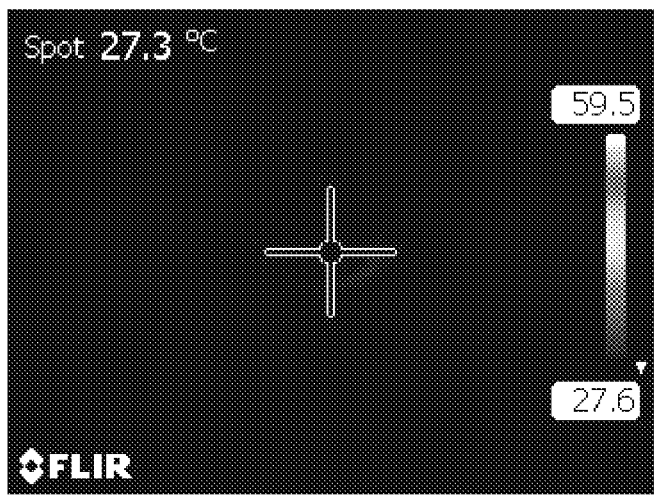

The thiolated pyropheophorbide-a telodendrimer (named as PEG$^{5k}$-Cys$_4$-Por$_4$-CA$_4$, FIG. 16A, FIG. 17) was synthesized by replacing 4 of the 8 cholic acids of our previously reported thiolated telodendrimer (PEG$^{5k}$-Cys$_4$-L$_8$-CA$_8$) using the same strategy[1,2]. The typical procedure for synthesis of PEG$^{5k}$-Cys$_4$-Por$_4$-CA$_4$ was as follows: (Fmoc)Lys (Fmoc)-OH (3 eq.) was coupled onto the N terminus of PEG using DIC and HOBt as coupling reagents until a negative Kaiser test result was obtained, thereby indicating completion of the coupling reaction. PEGylated molecules were precipitated by adding cold ether and then washed with cold ether twice. Fmoc groups were removed by the treatment with 20% (v/v) 4-methylpiperidine in dimethylformamide (DMF), and the PEGylated molecules were precipitated and washed three times by cold ether. White powder precipitate was dried under vacuum and one coupling of (Fmoc)Lys (Fmoc)-OH and one coupling of (Dde)lys(Fmoc)-OH were carried out respectively to generate a third generation of dendritic polylysine terminated with four Dde and Fmoc groups on one end of PEG. Then the Fmoc groups were removed. (Fmoc)Cys(Trt)-OH, (Fmoc)Ebes-OH and Cholic acid NHS ester (12 eq.) were coupled step by step to the terminal end of dendritic polylysine. After the removal of Dde protecting group by 2% (v/v) hydrazine in DMF, (Fmoc)Ebes-OH and pyropheophorbide-a (12 eq.) were coupled subsequently to the leftover amino groups on the terminal end of dendritic polylysine. The Trt groups on cysteines were removed by TFA/H2O/ethanedithiol (EDT)/triethylsilane (TIS) (94:2.5:2.5:1, v/v) resulting in PEG$^{5k}$-Cys$_4$-Por$_4$-CA$_4$ thiolated telodendrimer (FIG. 16A, FIG. 17). The thiolated telodendrimer was recovered from the mixture by three cycles of dissolution/reprecipitation with DMF and ether, respectively. Finally, the thiolated telodendrimer was dissolved in acetonitrile/water and lyophilized. The molecular weight of PEG$^{5k}$-Cys$_4$-Por$_4$-CA$_4$ was collected on ABI 4700 MALDI TOF/TOF mass spectrometer (linear mode) using R-cyano-4-hydroxycinnamic acid as a matrix. The mono-dispersed mass traces were detected for the starting PEG and the telodendrimers, and the molecular weights of the telodendrimers from MALDI-TOF MS (FIG. 18) were almost identical to the theoretical value.

Example 2. Generation of Metallic Telodendrimers

Preparation of Metallic Nanoporphyrins.
To generate telodendrimers with a chelated metal, excess free metal ions (e.g., 10-fold excess) were incubated with telodendrimers in methanol/chloroform for 1-5 hrs under nitrogen according to previously reported methods[6,49]. Free metal was removed by column filtration with a molecular weight cut off of 3,500. The metal porphyrin-lipid was then aliquoted, dried and stored under argon at −20° C.

Example 3. Preparation of Nano-Porphyrin Micelles

Metallic NPs were generated by dissolving the metal-telodendrimer in PBS with sonication. 20 mg thiol free porphyrin-telodendrimer was dissolved in 1 mL phosphate buffered saline (PBS) followed by sonication for 10 min to form non-crosslinked nanoporphyrins. To make targeting micelles, PLZ4-conjugated telodendrimers (PLZ4-PEG$^{5k}$-CA$_8$) were mixed with PEG$^{5k}$-Por$_4$-CA$_4$. After self-assembly, the more hydrophilic targeting PLZ4 ligands were displayed on the surface of micelles.

In order to make disulfide crosslinked micelles, 20 mg total amount of PEG$^{5k}$-Cys$_4$-Por$_4$-CA$_4$ and PEG$^{5k}$-Cys$_4$-L$_8$-CA$_8$ was dissolved in 1 mL phosphate buffered saline (PBS) to form micelles and then sonicated for 10 min. The thiol groups on the telodendrimer were oxidized to form disulfide linkages by hydrogen peroxide. The level of free thiol groups were monitored by Ellman's test over time. The micelle solution was used for further characterizations without dialysis after the level of free thiol groups remained at a constant low value.

Characterization of Metallic Nanoporphyrins.
The size and size distribution of nanoporphyrins were measured by dynamic light scattering (DLS) instruments (Microtrac). The concentrations were kept at 1.0 mg/mL for DLS measurements. All measurements were performed at 25° C., and data were analyzed by Microtrac FLEX Software 10.5.3. The morphology of nanoporphyrins was observed on a Philips CM-120 transmission electron microscope (TEM). Briefly, the aqueous nanoparticle solution (1.0 mg/mL) was deposited onto copper grids, with or without staining by phosphotungstic acid (PTA) for 2 seconds, and measured at room temperature. The absorbance and the fluorescence signal of nanoporphyrins were measured on a fluorescence spectrometry (SpectraMax M2, Molecular Devices, USA). The near infrared fluorescence of nanoporphyrin solutions (10). 10 was scanned using a Kodak multimodal imaging system IS2000MM. The thermo property of nanoporphyrin solutions (10 μL) was studies using a Flir thermal camera. The ROS production of nanoporphyrins was studied using 2',7'-Dichlorofluorescin diacetate (DCF) as an indicator and compared with PBS.

Radiolabeling.
$^{64}$CuCl$_2$ in 0.1 M HCl (Washington University, MO, USA) was buffered with 1.0 M ammonium acetate to pH 7. PEG$^{5k}$-Por$_4$-CA$_4$ telodendrimer was dissolved in methanol before adding a small volume of buffered $^{64}$CuCl$_2$. The radiolabeling solution was incubated for 30 min at room temperature. The methanol was evaporated and the film of telodendrimers was rehydrated with PBS to generate $^{64}$Cu labeled NPs. Free $^{64}$Cu was removed by centrifuged filtration using 3500 kDa cutoff Amicon centrifugal filter units (Millipore, Billerica, Mass., USA), or alternatively, Micro Bio-Spin 6 columns (Bio-Rad, Hercules, Calif., USA). Radiochemical purity and yield were assessed using instant thin-layer chromatography (ITLC). To prepare dual-labeled Gd/$^{64}$Cu NPs, pre-prepared Gd-telodendrimer was added to $^{64}$Cu-PEG$^{5k}$-Por$_4$-CA$_4$ telodendrimer radiolabeling solution in methanol, followed by drying, reconstitution in PBS, and purification.

Figure 12A:
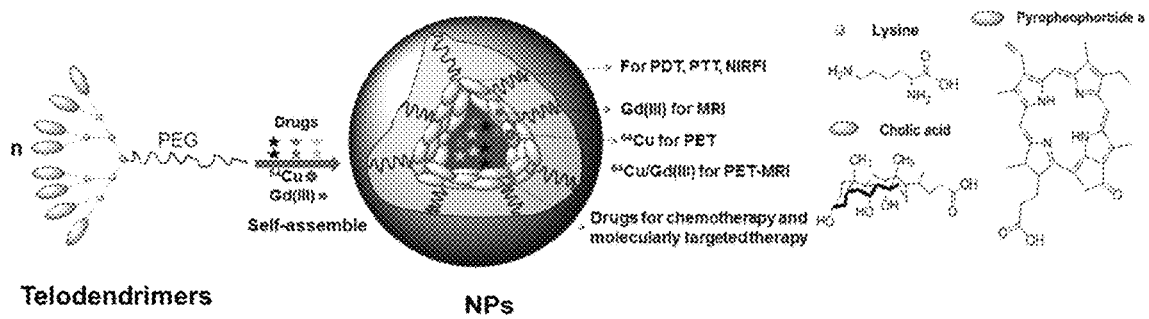
FIG. 12A-12L shows various aspects of the invention, including.
Figure 12B:
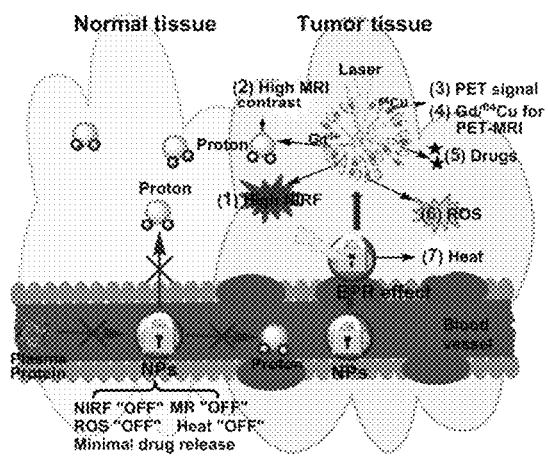
Figure 12C:
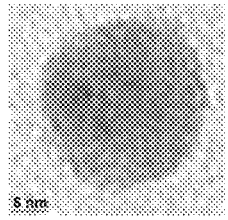
Figure 12D:
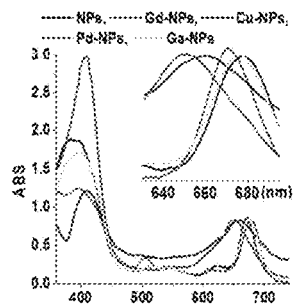
Figure 12E:
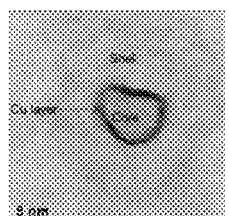
Figure 12F:
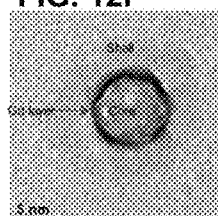
Figure 19:
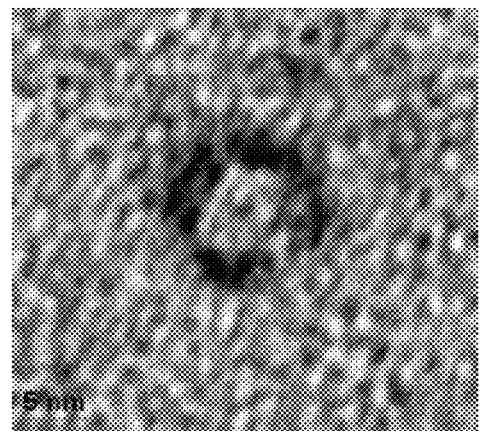
FIG. 19 shows a TEM image of Cu(II) loaded nanoporphyrins without staining.

Results
Synthesis and Characterization of NPs.
NPs were formed by the self-assembly of a novel class of hybrid amphiphilic polymers (called telodendrimer) comprised of linear polyethylene glycol (PEG) and dendritic oligomers of pyropheophorbide-a (Por, a porphyrin analogue) and cholic acid (CA) (FIG. 12A-FIG. 15). $PEG^{5k}$-$Por_4$-$CA_4$, a representative telodendrimer, is shown in FIG. 12A. Transmission electron microscopy (TEM) showed that the NPs were spherical with a size of 20 nm (FIG. 12C). NPs have two absorption peaks, one at 405 nm and one in the near-infrared (NIR) range of 680 nm (FIG. 12D). $PEG^{5k}$-$Por_4$-$CA_4$ has the intrinsic ability to chelate a variety of metal ions, such as copper (Cu(II)), palladium (Pd(II)), gadolinium (Gd(III)) and gallium (Ga(III)). Metal ion-loaded NPs, generated by the self-assembly of these metal-telodendrimers in PBS, were found to exhibit a unique shift in the absorbance peak (650-690 nm) (FIG. 12D). When metal ions are loaded into the porphyrin components of the NPs, the heavy atoms scatter electrons to a large angle that leads to more phase shift and increases the contrast in TEM. Thus the metal ion layer can be observed under TEM even without staining (FIG. 19). After staining with phosphotungstic acid and observation by TEM, the metal layer was found at the interface between the hydrophobic core and the hydrophilic corona of the NPs (FIG. 12E, FIG. 12F).

Figure 12G:
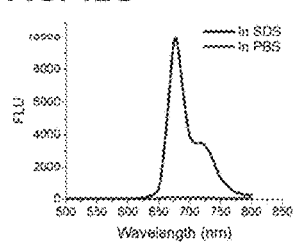
Figure 12H:
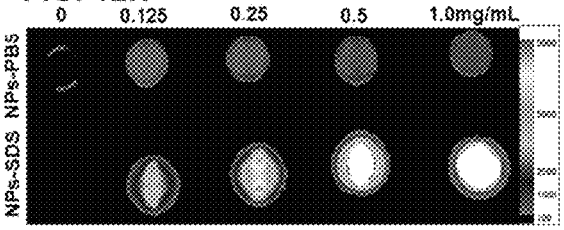
Figure 12I:
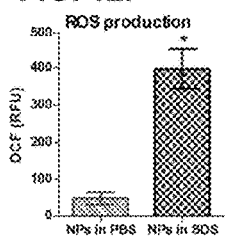
Figure 20A:
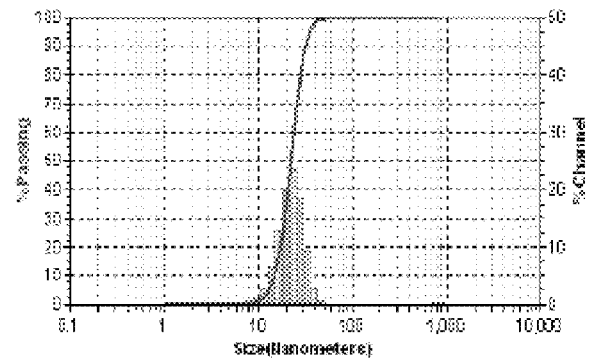
FIG. 20A-20B shows the particle size of NPs in the absence FIG. 20A and in the presence FIG. 20B of 2.5 g/L SDS. The particle size was measured by dynamic light scattering (DLS). NPs were broken down completely upon addition of SDS.
Figure 20B:
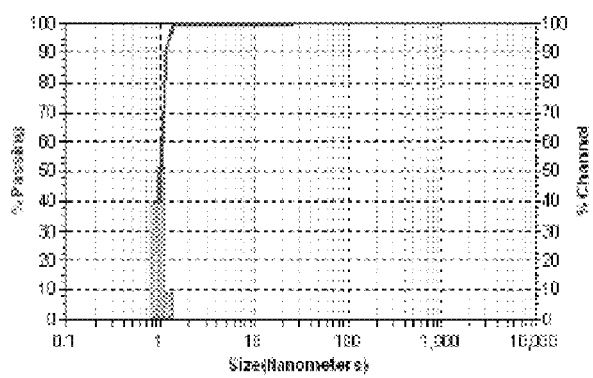
Figure 21:
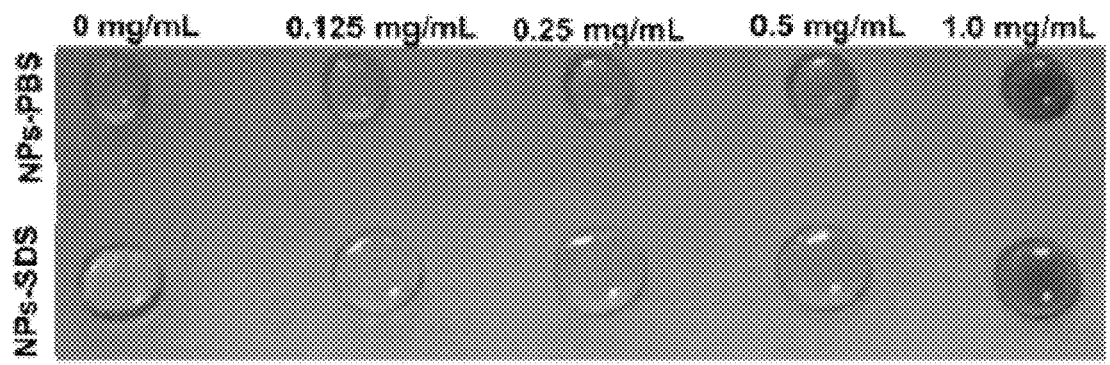
FIG. 21 shows a bright field image of the drops of nanoporphyrin solution in the absence and in the presence of SDS.
Figure 22A:
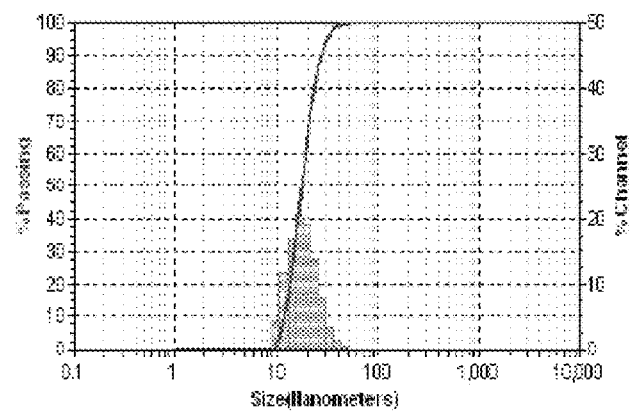
FIG. 22A-22B shows the particle size of free pyropheophorbide-a loaded standard $PEG^{5k}$-$CA_8$ micelles (NM-POR) in the absence FIG. 22A and in the presence FIG. 22B of 2.5 g/L SDS. The particle size was measured by dynamic light scattering (DLS). NM-POR was broken down completely upon addition of SDS.
Figure 22B:
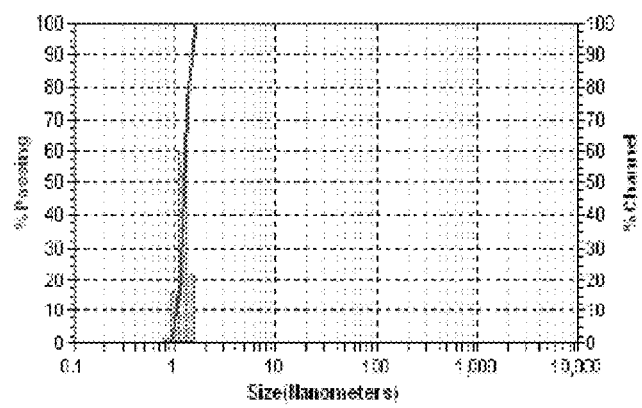

When excited at 405 nm, the NPs formulated in PBS showed a very weak red fluorescence emission with a peak value at 660 nm (FIG. 12G, red curve). This is not unexpected because of the π-π interactions and hydrophobic characteristics, Por molecules can easily form highly ordered structures in the core of the NPs, contributing to the strong self-quenching effect of the excited state in the aqueous medium[10]. In contrast, when the NPs were disrupted by sodium dodecyl sulfate (SDS)[11] (FIG. 20), strong fluorescence at 660 nm was observed when excited at 405 nm (FIG. 12G, blue curve). FIG. 12h compared the NIR fluorescence of NPs as a function of NP concentration, with or without addition of SDS (FIG. 21). It is clear that NIR fluorescence signal of the NPs is greatly amplified upon micellar dissociation, which is expected to occur at tumor sites and/or inside the tumor cells. We have used our previously reported $PEG^{5k}$-$CA_8$ micelles[11-17] as a conventional micelle-based nanocarrier to physically encapsulate Por for comparison. NPs demonstrated 10 times more self-quenching than Por loaded $PEG^{5k}$-$CA_8$ micelles (NM-POR) with the same concentration of Por (FIG. 22, FIG. 23), indicating quenching was a distinct characteristic of Por molecules that were uniquely assembled in the core of a nanoporphyrin construct. Similar to the fluorescence property, NPs also possess architecture-dependent "on/off" photodynamic transduction. The singlet oxygen generated by NPs in PBS after light irradiation was minimal but could be restored upon the addition of SDS (FIG. 12I).

Figure 12J:
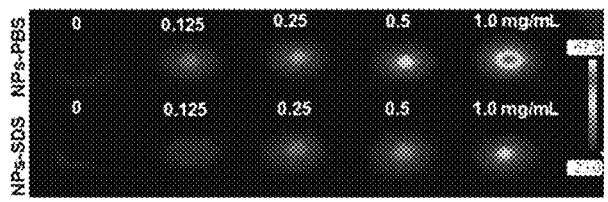
Figure 12K:
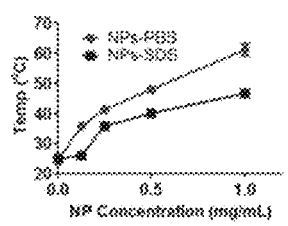
Figure 12L:
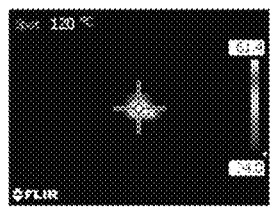
Figure 24A:
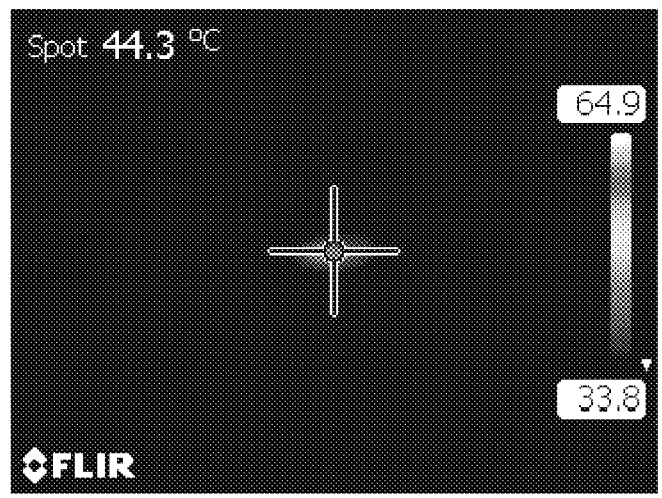
FIG. 24A-24B shows thermal images of NM-POR solution (10 μL) in the absence and in the presence of SDS, as monitored by a thermal camera after irradiation with a NIR laser (690 nm) at 1.25 w/cm$^2$ for 20 seconds. The concentration of pyropheophorbide-a was kept at the 0.2 mg/mL for NM-POR, which was equal to the concentration of pyropheophorbide-a in 1.0 mg/mL of NPs.
Figure 24B:
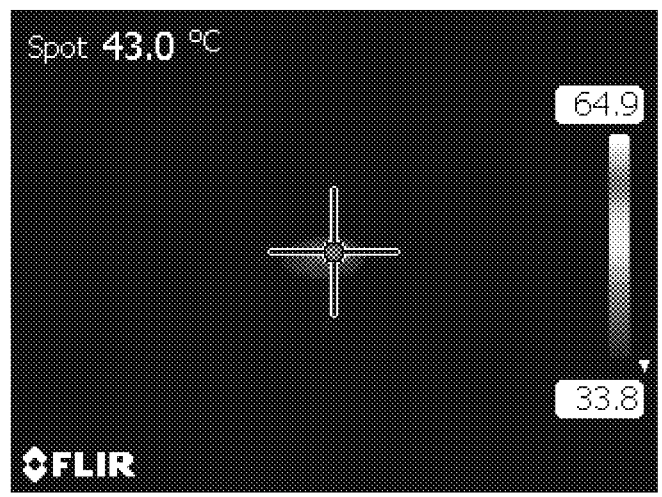

As NPs are highly self-quenched in PBS, energy is released in the form of heat instead of fluorescence and/or singlet-oxygen generation upon laser irradiation (FIG. 12J, FIG. 12K). The temperature of the NP solution increased from 24° C. to 62° C. as NP concentrations increased from 0 to 1.0 mg/mL. When NPs were dissociated in the presence of SDS and irradiated with the same dose of light, strong fluorescence but less significant increase in solution temperature was observed (FIG. 12J, FIG. 12K). To the contrary, NM-POR only showed moderate temperature increase in PBS compared to that in SDS with same level of irradiation (FIG. 24), indicating the photothermal transduction was efficient only when Por was confined in the unique architecture of NPs. We could further fine-tune the photothermal transduction of NPs by varying the light dose and NP concentrations. We demonstrated that a super high temperature (120° C.) could be achieved for the NPs at 4.0 mg/mL with irradiation at 1.25 W $cm^{-2}$ for 120 seconds (FIG. 12L), leading to melting of the substrate plastic film. While irradiation with low dose of light (0.1 W $cm^{-2}$) for 120 seconds, the temperature of NP solution only increased a few degree (FIG. 17).

Example 4. Preparation of Drug Loaded Nanoporphyrins

Preparation of Drug Loaded Micelles
Doxorubicin was loaded into the micelles by the solvent evaporation method as described previously. Before the encapsulation of DOX into the polymeric micelles, DOX.HCl was stirred with 3 molar equivalent of triethylamine in chloroform (CHCl3)/methanol (MeOH) (1:1, v/v) overnight to remove HCl from DOX.HCl. 20 mg telodendrimer along with different amount of neutralized DOX were first dissolved in CHCl3/MeOH, mixed, and evaporated on rotavapor to obtain a homogeneous dry polymer film. The film was reconstituted in 1 mL phosphate buffered solution (PBS), followed by sonication for 30 min, allowing the sample film to disperse into micelle solution. To track their in vivo fates, hydrophobic NIRF dye DiD was encapsulated into some of the micelles using similar methods. Finally, the micelle formulation was filtered with 0.22 μm filter to sterilize the sample. To determine the amount of DOX, DOX-loaded micelles were diluted with DMSO (micelle solution/DMSO: 1:9, v/v) to dissociate micelle nanoparticles and the fluorescence was measured by NanoDrop 2000 spectrophotometer (Thermo Scientific), wherein calibration curve was obtained using a series of DOX/DMSO standard solutions with different concentrations. The DOX loaded disulfide crosslinked micelles were prepared via the same method followed the oxidation of the thiols to form intramicellar disulfide bonds by hydrogen peroxide.

Hydrophobic drugs, such as doxorubicin, paclitaxel, vincristine, bortezomib, sorafenib and 17-allylamino-17-demethoxygeldanamycin were loaded into nanoporphyrins using a similar method. To determine the amount of encapsulated drugs, drug-loaded nanoporphyrins were diluted with DMSO (nanoporphyrin solution/DMSO: 1:9, v/v) to dissociate nanoparticles. The drug loading was analyzed on a HPLC system (Waters), wherein calibration curve was obtained using a series of drug/DMSO standard solutions with different concentrations. The drug loaded disulfide crosslinked nanoporphyrins were prepared via the same method followed the oxidation of the thiols to form intramicellar disulfide bonds.[2]

Figure 16B:
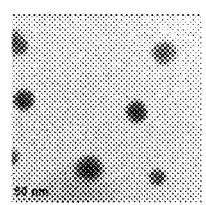
Figure 16C:
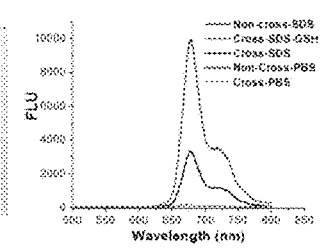

DOX release in Human Plasma.
NP-DOX solutions were prepared to determine the in vitro drug release profile in plasma. The initial DOX concentration was 1.0 mg/mL while the NP concentration was 10 mg/mL. NP alone and our reported standard micelles (with porphyrins)[11] with DOX at the same drug content were also prepared for comparison. When DOX was encapsulated in the core of NPs, the proximity between DOX and Por was within the FRET range allowing efficient energy transfer from DOX to Por molecules upon excitation of DOX at 480 nm (FIG. 16E, FIG. 16F). Upon excitation at 480 nm, the signal of NPs alone was much smaller in comparison with the corresponding FRET signal. Therefore, by monitoring the dynamic change of FRET ratio, we were able to monitor the release of DOX from NPs in real time. Aliquots of these nanoparticle solutions were diluted 9 times by human plasma and incubated in an incubator at 37° C. with a stirring speed of 100 rpm. The fluorescence spectra of these nanoparticle solutions were measured by NanoDrop spectrophotometer (Thermo Scientific) at pre-determined time points. In some experiments, the nanoparticle solutions were irradiated with light for 5 min or incubated in a water bath at fixed temperature in order to study the effect of light or temperature on the DOX loaded NPs.

The stability study was performed to monitor the change in fluorescence and particle size of nanoporphyrins and disulfide crosslinked nanoporphyrins in the presence of sodium dodecyl sulfate (SDS), which was reported to be able to efficiently break down polymeric micelles[4]. An SDS solution (7.5 mg/mL) was added to aqueous solutions of nanoporphyrins (1.5 mg/mL). The final SDS concentration was 2.5 mg/mL and the micelle concentration was kept at 1.0 mg/mL. The fluorescence signal of the solutions was measured on a fluorescence spectrometry (SpectraMax M2, Molecular Devices, USA). The size and size distribution of the nanoporphyrin solutions was monitored at predetermined time intervals by DLS. The stability of the micelles was also evaluated in the presence of glutathione (GSH, 20 mM) together with SDS. The stability of DOX-loaded NPs was further studied in 50% (v/v) plasma from healthy human volunteers. The mixture was incubated at physiological body temperature (37° C.) followed by size measurements at predetermined time intervals up to 48 hrs.

Results

We further demonstrated that NPs formed by $PEG^{5k}$-$Por_4$-$CA_4$ could efficiently carry a variety of poorly water-soluble chemotherapeutic drugs and molecularly targeted drugs. For instance, chemotherapeutic agents (doxorubicin, paclitaxel and vincristine) and molecularly targeted drugs such as proteasome inhibitor (bortezomib), tyrosine kinase inhibitor (sorafenib) and heat shock protein 90 (Hsp90) inhibitor (17-allylamino-17-demethoxygeldanamycin, 17AAG) could be readily incorporated into NPs resulting in significant increase in water solubility. The final particle sizes of the drug-loaded NPs were all around 12-20 nm, which were similar to those of empty NPs (FIG. 25).

Figure 16D:
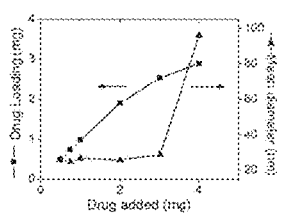
Figure 16E:
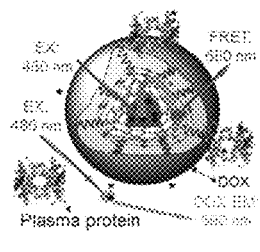
Figure 16F:
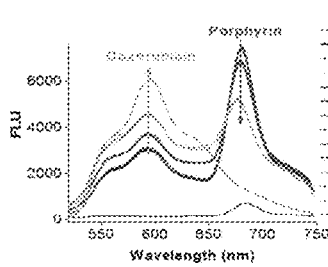
Figures 16G, 16H:
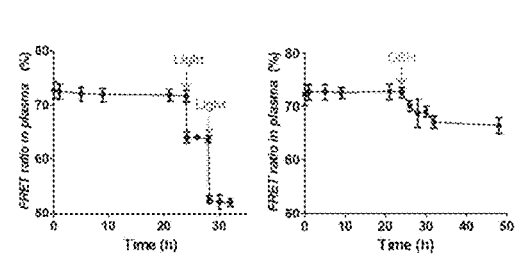

We demonstrated that DOX was able to be encapsulated inside crosslinked NPs with a loading capacity of 3.7 mg/mL (FIG. 16D). The final particle size of DOX-loaded and crosslinked NPs (CNP-DOX) was around 20 nm with DOX loading up to 2.5 mg/mL. We then investigated the interaction of CNP-DOX with human plasma to simulate the destabilizing conditions in blood for in vivo applications. The particle size of CNP-DOX was highly stable in human plasma (FIG. 26). We utilized the fluorescence resonance energy transfer (FRET) between the doxorubicin and NPs to monitor the real time drug release in human plasma (FIG. 16E). As shown in FIG. 16F-16G, the FRET signal was very stable when CNP-DOX was incubated in human plasma for 24 hrs at 37° C., indicating there was minimal doxorubicin release from crosslinked NPs. However, there was dramatic FRET signal decrease with light exposure at 24 hrs and 28 hrs, respectively (FIG. 16F-16G). The above results indicated that disulfide crosslinked NPs could be triggered to release drug via light exposure. Alternatively, the DOX release could be triggered by GSH at intra-cellular level (~10 mM) and monitored by FRET (FIG. 16H).

Figure 18:
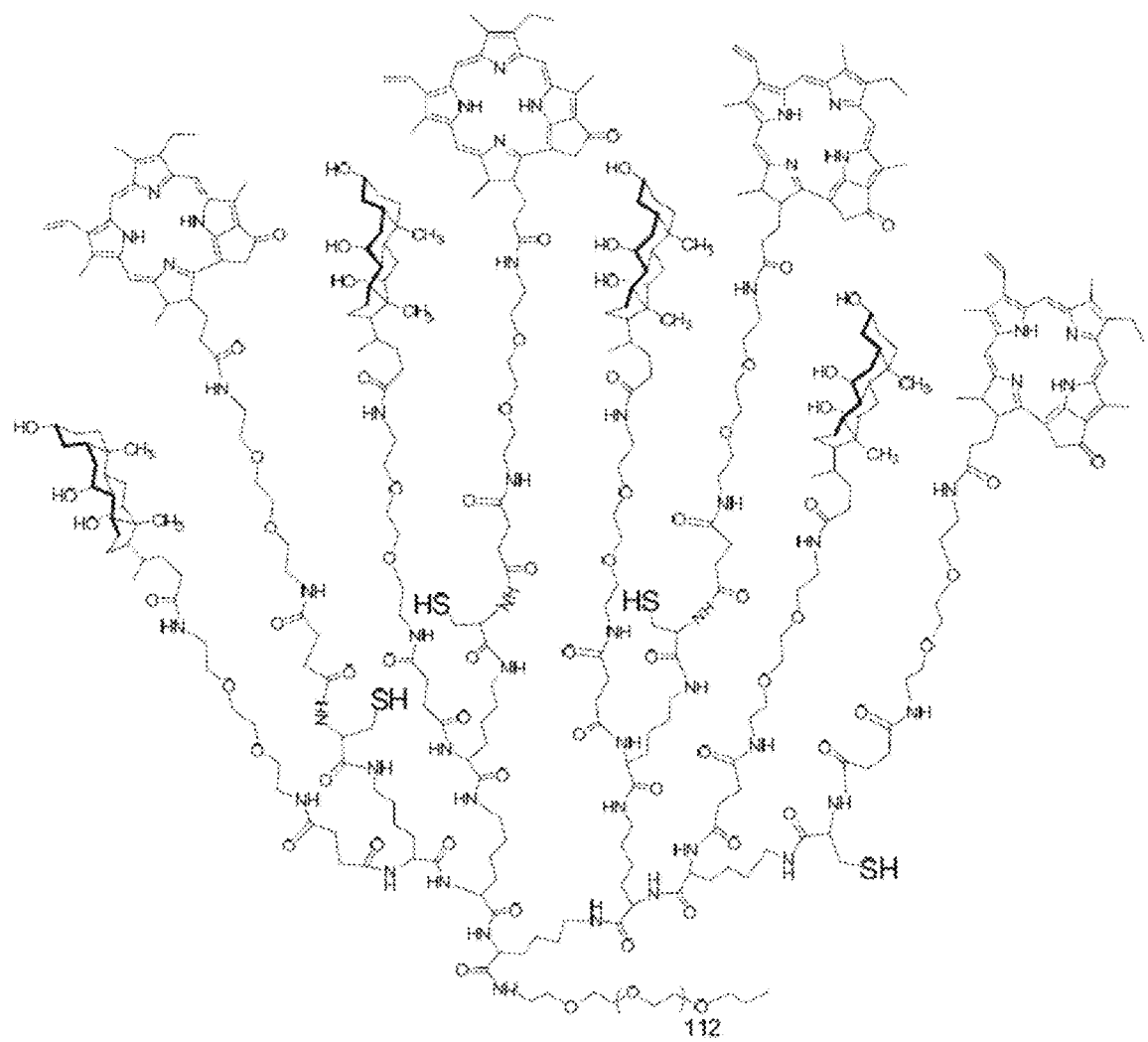
FIG. 18 shows the chemical structure of the $PEG^{5k}$-$Cys_4$-$Por_4$-$CA_4$ telodendrimer.
Figure 27:
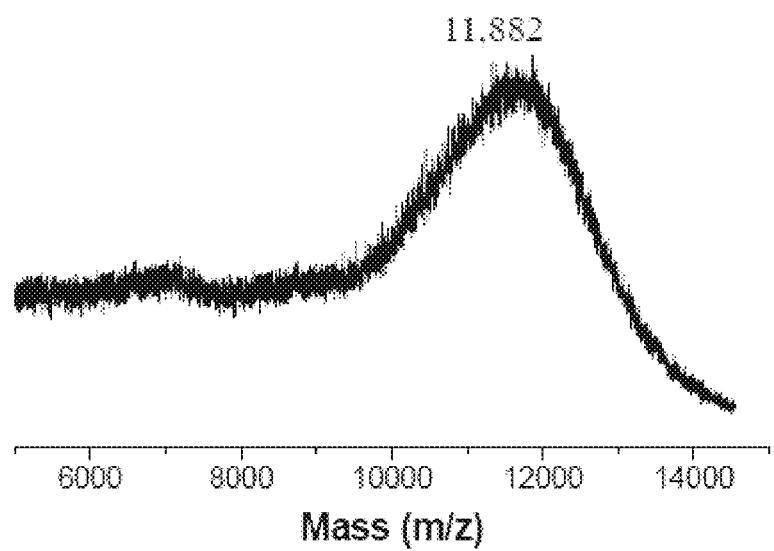
FIG. 27 shows a MALDI-TOF mass spectrum of the $PEG^{5k}$-$Cys_4$-$L_8$-$CA_8$ telodendrimer.
Figure 28A:
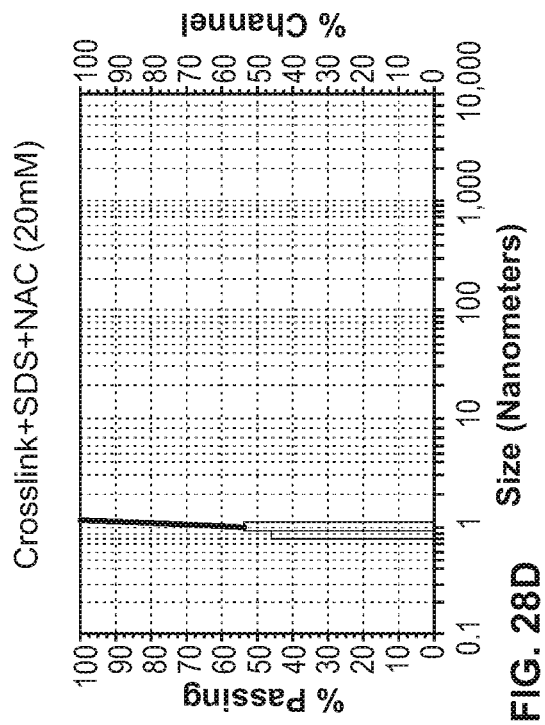
FIG. 28A-28D shows the particle size of disulfide crosslinked NPs in the absence FIG. 28A and in the presence of: 2.5 g/L SDS FIG. 28B, 2.5 g/L SDS+20 mM NAC FIG. 28C, 2.5 g/L SDS+20 mM GSH FIG. 28D. The particle size was measured by dynamic light scattering (DLS). Upon addition of SDS, non-crosslinked NPs were broken down completely. In contrast, the size of the crosslinked NPs persisted at 20-30 nm under the same conditions. The disulfide cross-linked NPs formed were dissociated in the presence of SDS at around 40 min after adding the endogenous reducing agent glutathione (GSH, 20 mM) and exogenous reducing agent N-acetylcysteine (NAC, 20 mM).
Figure 28C:
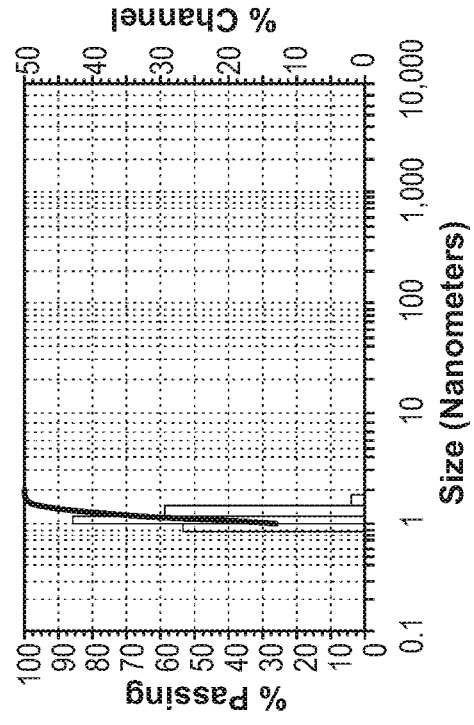
Figure 28B:
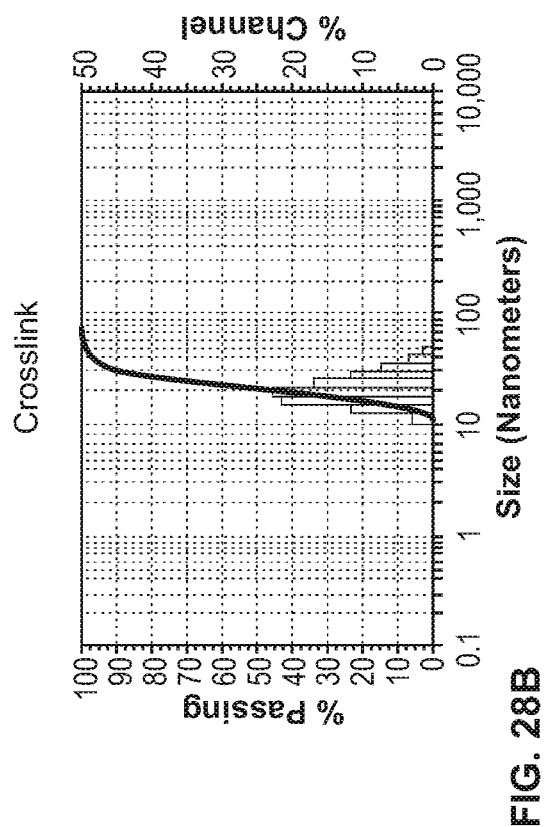
Figure 28D:
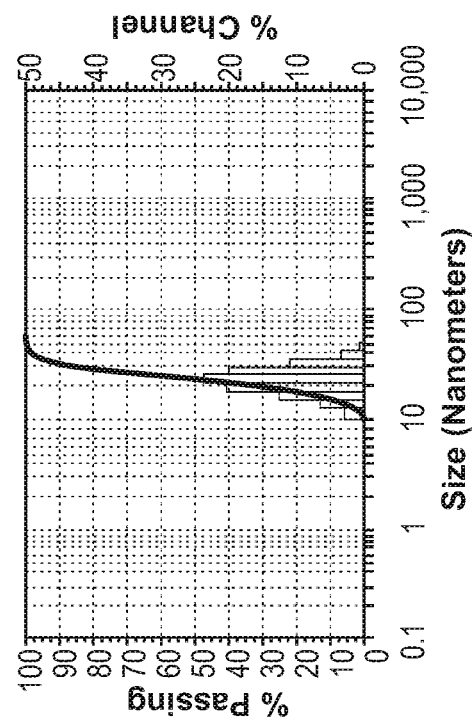

Blood is the first biological barrier for nanoparticle-based drug delivery systems via intravenous administration. Interaction with blood proteins and lipoproteins may cause the dissociation of nanoparticles and lead to premature drug release. In order to further increase the structural stability of NPs in blood circulation, we have applied reversible disulfide crosslinking strategy to the NP platform. Four cysteines were introduced to the oligolysine backbone of the telodendrimer to form $PEG^{5k}$-$Cys_4$-$Por_4$-$CA_4$ (FIG. 16A, FIG. 18, FIG. 27). The resulting NPs were then crosslinked via disulfide bond through oxidation of the thiol groups on the cysteines. TEM showed that these disulfide crosslinked NPs were spherical vesicles of 20-30 nm in diameter (FIG. 16B), which is similar to their non-crosslinked counterparts. Similar to the noncrosslinked NPs, the fluorescence of crosslinked NPs was also highly quenched in PBS.

Correspondingly, the fluorescence was restored in the presence of SDS and endogenous reducing agent such as glutathione (GSH) at intra-cellular levels[11] (FIG. 16C). As shown in FIG. 16C, disulfide crosslinked NPs also showed very weak red fluorescence emission with a peak value at 660 nm when excited at 405 nm (green curve). When the fluorescence emission spectra of the crosslinked NPs were recorded in the presence of SDS, there was increase in the peak emission at 660 nm (black curve). However, the peak value was significantly lower than that of the non-crosslinked NPs in the presence of SDS at the same porphyrin concentration. Upon addition of GSH, the disulfide crosslinked NPs were completely broken down and the peak at 660 nm in the fluorescence emission spectra increased further to a similar value as that of non-crosslinked NPs in the presence of SDS (pink curve). The crosslinked NPs could also retain their particle size in SDS but could be dissociated with the addition of reducing agents (FIG. 28).

Example 5. In Vitro Cytotoxicity

Methods

In Vitro Cytotoxicity and Mechanism.

SKOV-3 ovarian cancer cell line and PC3 prostate cancer cell line were used to evaluate the photosensitizing function of NPs. Cells were treated with NPs for 24 or 72 hrs followed by light irradiation at 24 hrs after treatment. Cell viability was determined using WST-8 kit. The heat and ROS production was investigated at the time of irradiation.

SKOV-3 ovarian cancer cell lines were used to evaluate the photosensitizing function of NPs. We first treated the cancer cells with various concentrations of NPs or 5-aminolevulinic acid (5-ALA), the traditional photodynamic diagnosis/therapy agent, for 24 hrs. After thorough washing, the cells were exposed to NIF light as indicated. Cell viability was determined using WST-8 proliferation kit 24 hrs after illumination. In another experiments, crosslinked NPs or DOX loaded crosslinked NPs, free DOX, and DOX loaded crosslinked micelles (without porphyrins)[5] were used to treat the cancer cells for 24 hrs. After three times of wash, cells were illuminated with light for 1 minute. Cell viability was determined by WST-8 after 24 hrs of incubation. In another study, the growth inhibitory effect of NP-AAG to LNCAP, PC3 and RPWE1 cells in comparison with NP alone and free drug 17AAG. Cells were seeded at 5000 cells/SOW/well and treated with the indicated drugs for 24 hrs. The drugs were removed and replaced with fresh medium, and then the cells were exposed to NIR light for 2 min. Growth inhibition was measured using MTT assay after 72 hrs. Apoptosis was analyzed 24 hrs later using annexin V and PI staining. HIF1α, survivin, AKT, STAT3 and Src levels were analyzed 12 hrs later using western blot and the corresponding antibodies.

We firstly treated SKOV-3 cells with or without 2.2 μM of NPs for 24 hrs followed by 30 minute loading with 2',7'-Dichlorofluorescin diacetate (DCF) in 96 well plate to monitor the ROS production. Cells were washed three times with PBS and replaced with fresh medium. A portion of the well was illuminated with NIR light (e.g., at 0.07 W cm$^{-2}$ for 60 seconds) and cell imaging was acquired under a fluorescence microscope using Metamorph program. Next, to evaluate the loss of mitochondria membrane potential ($\Delta\Psi$m) after pre-treated SKOV-3 cells with NPs, we loaded cells with 40 nM of DiOC6(3) for 20 minutes and a portion of the well was illuminated with NIR light. Twenty-four hours later, cells were labeled with propridium iodide (dead cells) and Hoechst 33342 (nucleus), and imaging was acquired by fluoresce microscope. Last, to investigate the cellular responses to NPs and photo-therapy, we evaluated the caspase 3/7 activity, which served as marker for a part of apoptosis pathway activation. SKOV-3 cells were treated with or without 2.2 µM NPs for 24 hrs. After wash, cells were exposed without light or light for 0.5, 1 and 2 minutes. After 24 hrs of incubation, caspase3/7 activity was measured by adding another 50 µL of working solution for another 45 minutes. The plate was read by plate reader (SpectraMax M2, Molecular Devices, USA). Lastly, for morphology study, SKOV-3 cells were cultured on 8-well chamber slides and treated with or without NPs for 24 hrs. Two hours after treatment with light, the slide was stained with Hema3®.

Results

Figure 29:
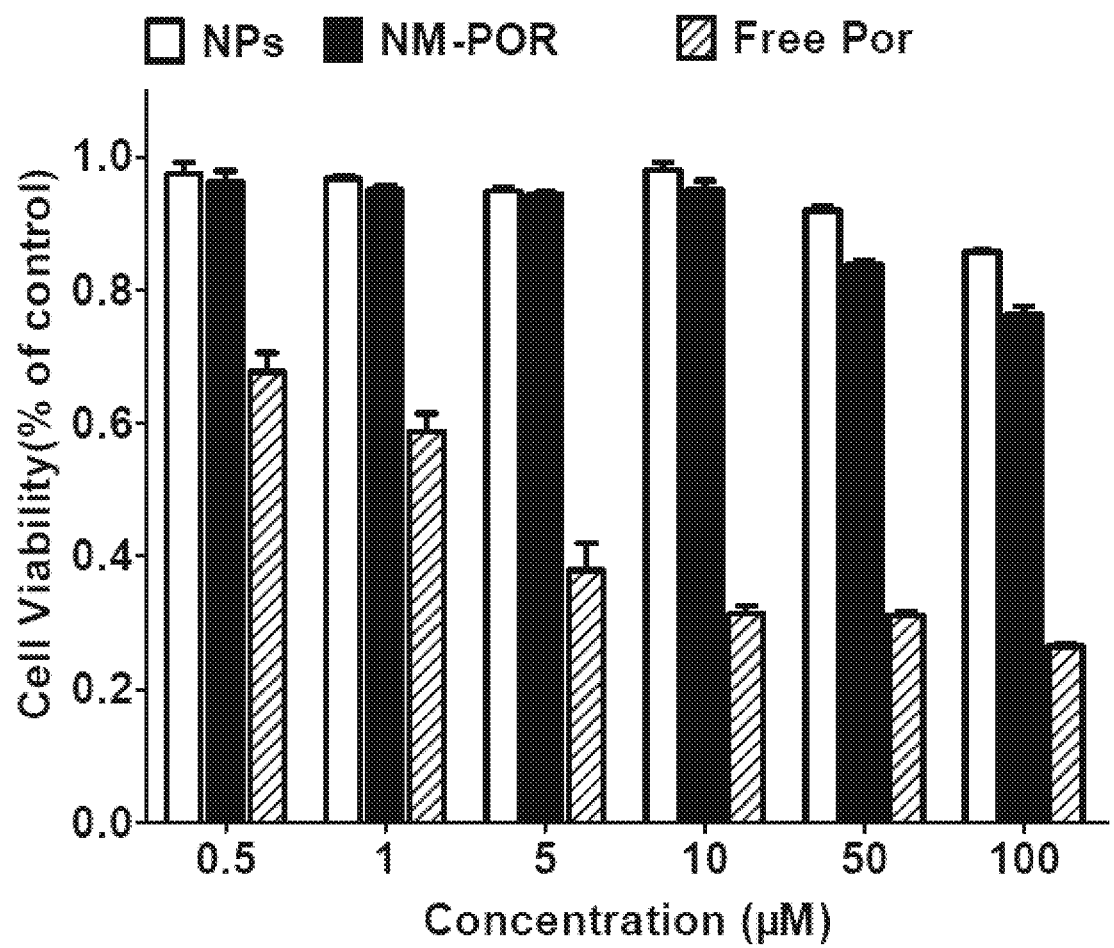
FIG. 29 shows the cytotoxicity in SKOV-3 ovarian cancer cells after 2 hrs exposure to NPs, Por loaded $PEG^{5k}$-$CA_8$ micelles (NM-POR) and free pyropheophorbide-a (Por) followed by an additional 22 hrs incubation under dark conditions.
Figure 30A:
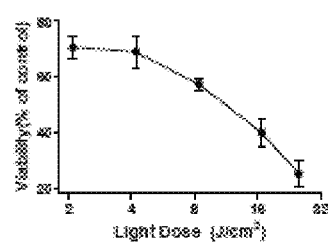
FIG. 30 shows: cytotoxicity in SKOV-3 ovarian cancer cells after FIG. 30A 2 hrs exposure to 4.4 μM NPs followed by illumination with various levels of NIR light, and FIG. 30B incubation with NPs or 5-ALA for 24 hrs followed by exposure to NIR light at 0.07 W cm$^{-2}$ for 60 seconds.
FIG. 30C shows ROS mediated cell death after NPs and light treatment of SKOV-3 ovarian cancer cells. Cells were treated with or without 2.2 μM NPs for 24 hrs and loaded with DCF for 30 min. After treatment with NIR light at 0.07 W cm$^{-2}$ for 60 seconds, images were acquired by fluorescence microscopy to detect ROS production.
FIG. 30D shows SKOV-3 ovarian cancer cells treated with 2.2 μM NPs for 24 hrs in a 96-well black-wall plate, stained with 40 nM of $DiOC_6(3)$ (Green, $\Delta\Psi m^{high}$) for 20 min at the end of incubation to evaluate mitochondria membrane potential ($\Delta\Psi m$), and followed by illumination of a portion of each well to elicit PDT effect. The illumination area was marked with "L." 24 hrs later, the cells were stained with propridium iodide (PI) for cell death.
FIG. 30E shows caspase3/7 activity in cells treated with different concentrations of NPs for 24 hrs followed by PDT. 24 hrs later, caspase3/7 activity was measured by SensoLyte® kit (Anaspec, Fremont, Calif.).
FIG. 30F shows cell morphology after PDT. SKOV-3 ovarian cancer cells were cultured on 8-well chamber slides and treated for 24 hrs with PBS, NPs alone and combination of NPs and light (at 0.07 W cm$^{-2}$ for 60 seconds). Cells were then fixed and stained with Hema3® after 2 hrs. Cells treated with NPs+light exhibited obvious nucleus swelling, cell rounding, membrane damage, and cytoplasm aggregation.
FIG. 30G shows the cytotoxicity effect of a combination of doxorubicin with NP-mediated photo-therapy. SKOV-3 ovarian cancer cells were treated with NPs alone, doxorubicin loaded nanoporphyrins (NP-DOX) or doxorubicin loaded standard micelles (NM-DOX) with various concentrations of DOX and/or NPs for 24 hrs. After washing, cells were exposed with light and cell viability was measured after 24 hrs. *p<0.05.
FIG. 30H shows the growth inhibitory effects of NP-AAG to PC3 prostate cancer cells in comparison with NP alone and free drug 17AAG. The NP concentration was kept the same for NP-AAG and NP groups. The drugs were removed and replaced with fresh medium, and then the cells were exposed to NIR light for 2 min. Growth inhibition was measured using MTT assay after 72 hrs. Left columns, no light; boxed right columns, with light. n=3.
FIG. 30I shows apoptosis analyzed 24 hrs later using annexin V and PI staining (n=3).
FIG. 30J shows the analysis of HIF1α, survivin, AKT, STAT3 nad Src levels 12 hrs later using Western blotting with the corresponding antibodies.
Figure 30B:
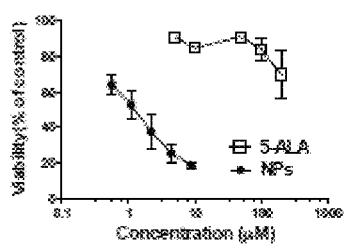
Figure 30C:
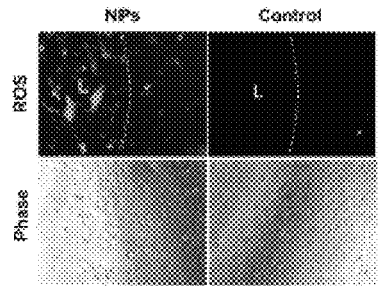
Figure 30D:
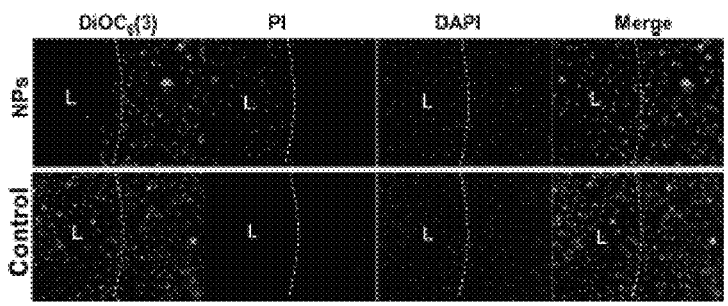
Figure 30E:
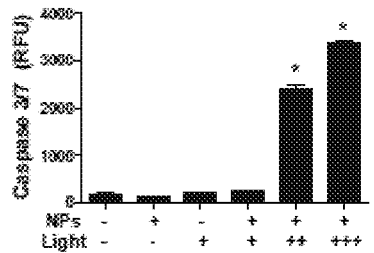
Figure 30F:
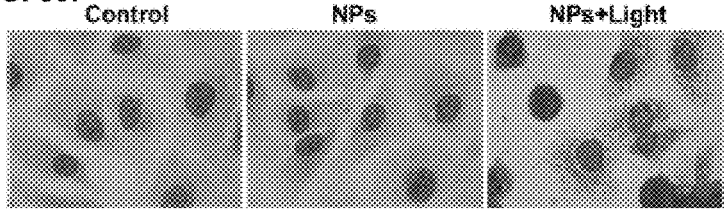
Figure 30G:
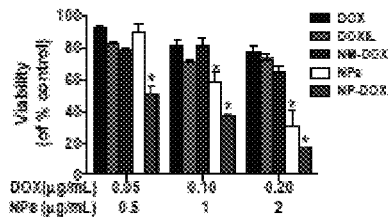
Figure 30H:
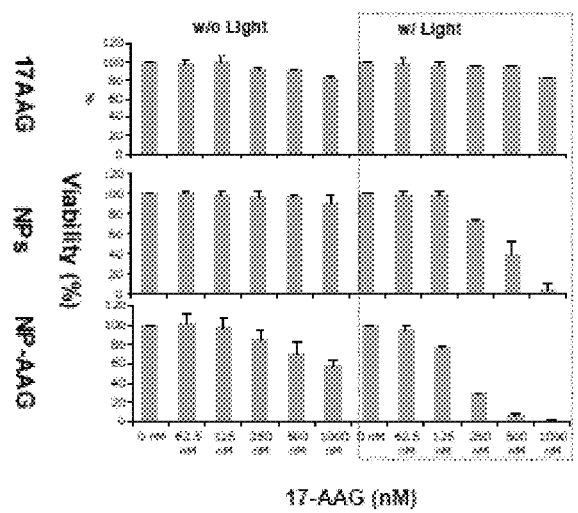
Figure 30I:
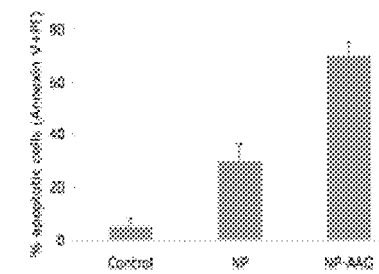
Figure 30J:
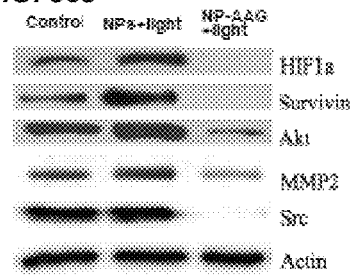
Figure 31:
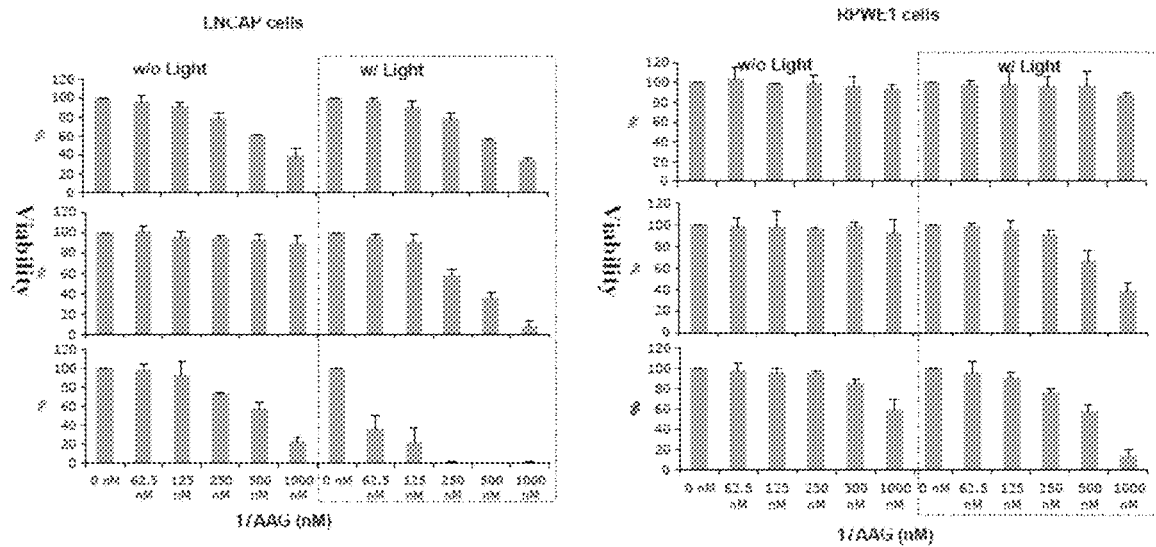
FIG. 31 shows the growth inhibitory effect of NP-AAG to LNCAP prostate cancer cells and RPWE1 normal prostate cells in comparison with NP alone and free drug 17AAG. The NP concentration was kept the same for NP-AAG and NP groups. The drugs were removed and replaced with fresh medium, and then the cells were exposed to NIR light for 2 min. Growth inhibition was measured using an MTT assay after 72 hrs. Left columns, no light; right boxed columns, with light. n=3.

We found the unique architecture-dependent ROS production of NPs (FIG. 12I) could be used to reduce the phototoxicity of photosensitizer itself. Without light irradiation, the intact NPs showed no observable cytotoxicity up to 1.0 mg/mL against SKOV-3 ovarian cancer cells while free Por showed significant cytoxicity in a dose-dependent manner (FIG. 29). The in vitro antitumor effect of NPs after light exposure was light-dose and NP-dose dependent (FIG. 30A, FIG. 30B) and was much more potent than 5-aminolevulinic acid (FIG. 30A-ALA, FDA approved agent for PDT) in cytotoxicity upon the same dose of illumination (FIG. 30B). The loss of cell viability was associated with intracellular ROS production (FIG. 30C), resulting in loss of mitochondrial membrane potential, cellular damage, and cell apoptosis evidenced by casepase3/7 activation (FIG. 30D-30F). Moreover, we found that NP-DOX mediated combination chemotherapy and photo-therapy was significantly more efficacious than NPs mediated photo-therapy alone, free DOX, or NM-DOX (DOX loaded standard micelles without porphyrin)[11] after the same light exposure (FIG. 30G). We further demonstrated NP-mediated photo-therapy could be synergistically combined with molecularly targeted drugs, such as Hsp90 inhibitor 17AAG. A strong synergistic effect was observed with 17AAG loaded NPs (NP-AAG) in both androgen independent PC3 prostate cancer cells (FIG. 30H, bottom) and androgen dependent LNCAP prostate cancer cells (FIG. 31, left, bottom). Immortalized normal prostate cells RWPE1 are relative resistant to this therapy (FIG. 31, right). NP-AAG has greater effect to induce apoptosis in PC3 cells as measured by Annexin V and PI staining (FIG. 30I). Interestingly, HIF1α, Akt, Survivin and MMP2 were increased by NPs on PDT, this induction as well as Src were depleted by NP-AAG (FIG. 30J), implying the mechanism of the strong synergistic effect of NP-AAG.

Figure 23:
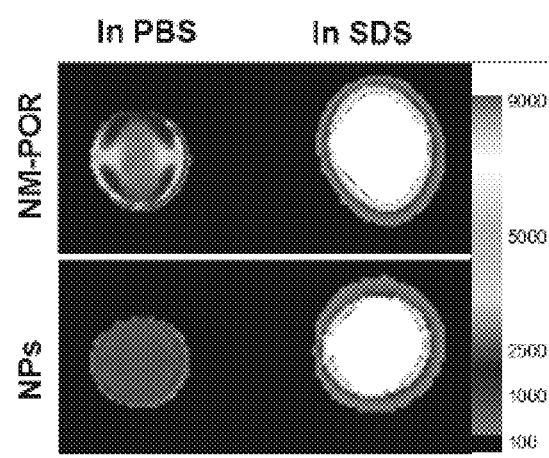
FIG. 23 shows near-infrared fluorescence imaging of free pyropheophorbide-a loaded standard $PEG^{5k}$-$CA_8$ micelle (NM-POR) 7 solution (10 μL) (upper panel) in the absence and in the presence of SDS with an excitation bandpass filter at 625/20 nm and an emission filter at 700/35 nm in comparison with that of nanoporphyrin solution (lower panel). The concentration of pyropheophorbide-a was kept at the 0.2 mg/mL for NM-POR, which was equal to the concentration of pyropheophorbide-a in 1.0 mg/mL of NPs. By calculating the ratio of the average fluorescence intensity in SDS to that in PBS, NPs were found to have 10 times more self-quenching than NM-POR with the same concentration of Por.
Figure 32A:
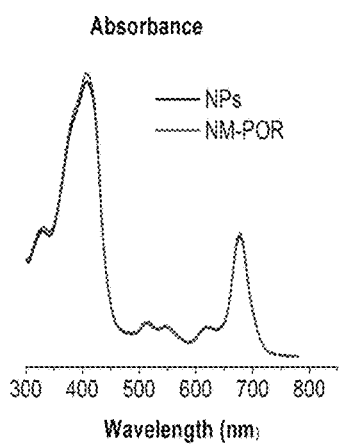
FIG. 32A shows the absorbance of crosslinked NPs and NM-POR (both contain 0.5 mg/mL of Por) in 10×DMSO.
Figure 32B:
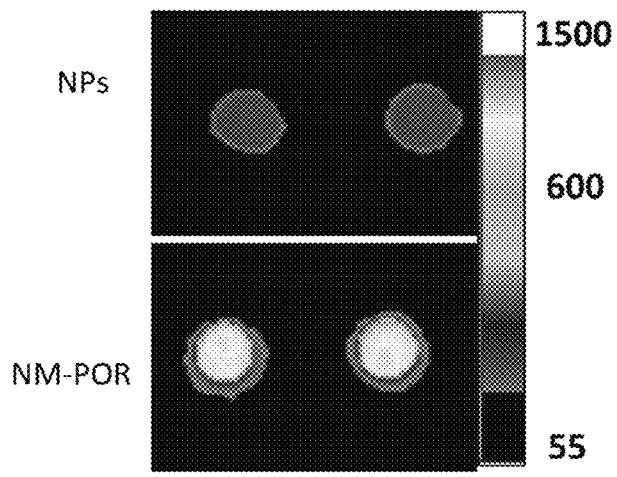
FIG. 32B shows the NIR fluorescence signal and FIG. 32C shows the quantitative fluorescence of blood drops drawn from nude mice bearing implanted tumor xenografts 5 min post-injection of crosslinked NPs and NM-POR (Por dose: 5 mg/kg). Images were analyzed as the average signal in the region of interest (ROI). ***p<0.001.
Figure 32C:
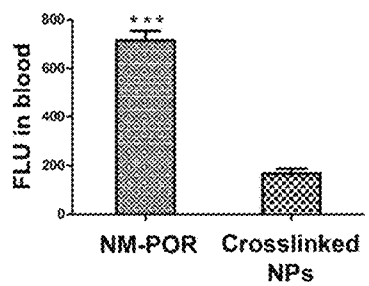
Figure 33:
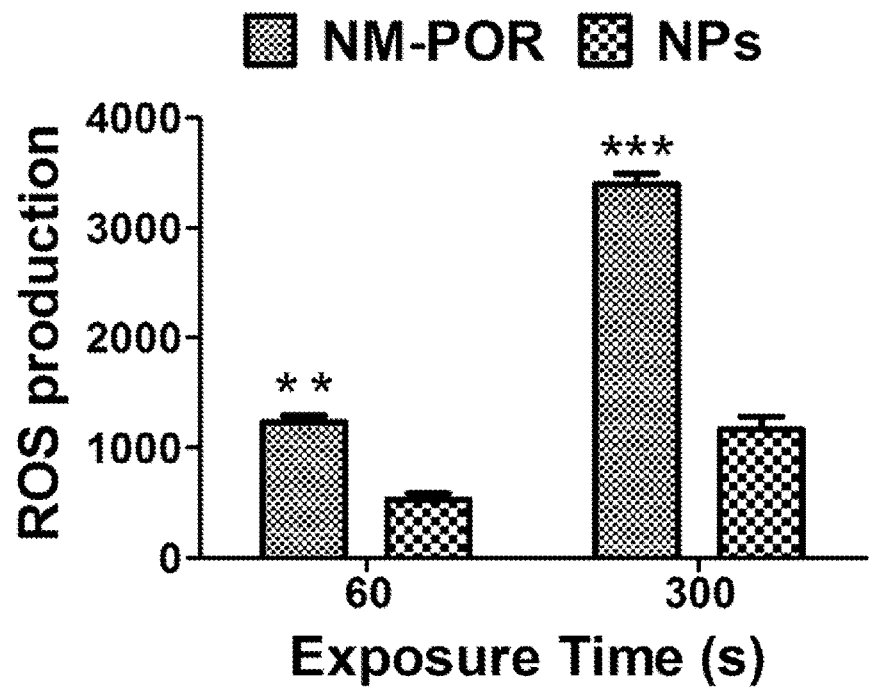
FIG. 33 shows ROS production of blood drops drawn from nude mice bearing implanted tumor xenografts 5 min post-injection of disulfide crosslinked NPs and NM-POR (Por dose: 5 mg/kg) after light exposure. Light dose: 0.1 W for 60 s and 300 s. Measured by using 2',7'-dichlorofluorescin diacetate (DCF) as a ROS indicator. p<0.002, *p<0.001.
Figure 34A:
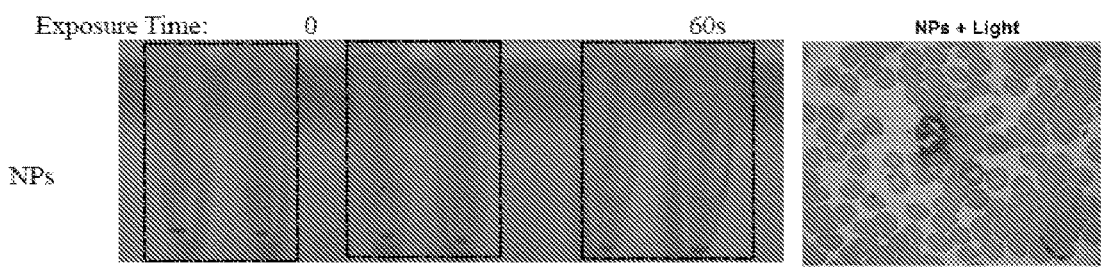
FIG. 34A-34D shows ex vivo hemolytic activity from nude mice bearing implanted tumor xenografts. 2 μL of blood collected from mice with crosslinked NP FIG. 34A-34B and NM-POR FIG. 34C-34D injection for 1 min was diluted into 100 μL of PBS followed by light exposure for 0, 60, and 300 seconds. (Por dose: 5 mg/kg) after light exposure. Light dose: 0.1 W cm$^{-2}$, 4 hours later, blood cells were spun down and hemolysis was observed in the samples from NM-POR treated mice FIG. 34A, FIG. 34C. Cytospin samples from 300 sec samples were further made for cell morphology evaluation FIG. 34B, FIG. 34D (Hema3® stain, 100× oil). In contrast to the normal blood cell morphology found in the crosslinked NP samples FIG. 34B, both RBCs and WBCs were massively destructed in the NM-POR samples FIG. 34D after light exposure, which was likely due to ROS related oxidative damage to the blood cells.
Figure 34B:
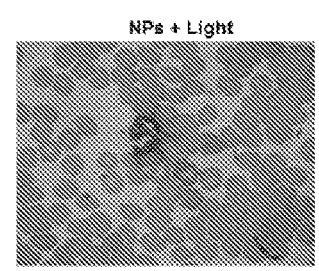
Figure 34C:
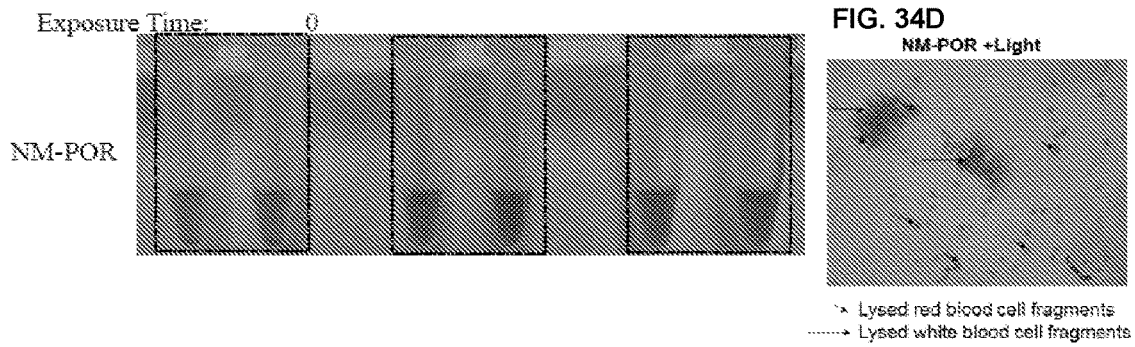
Figure 34D:
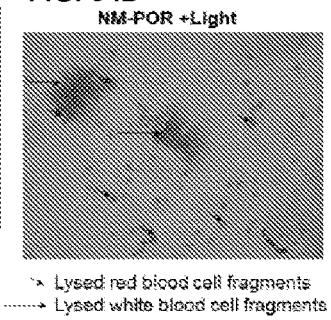
Figure 35:
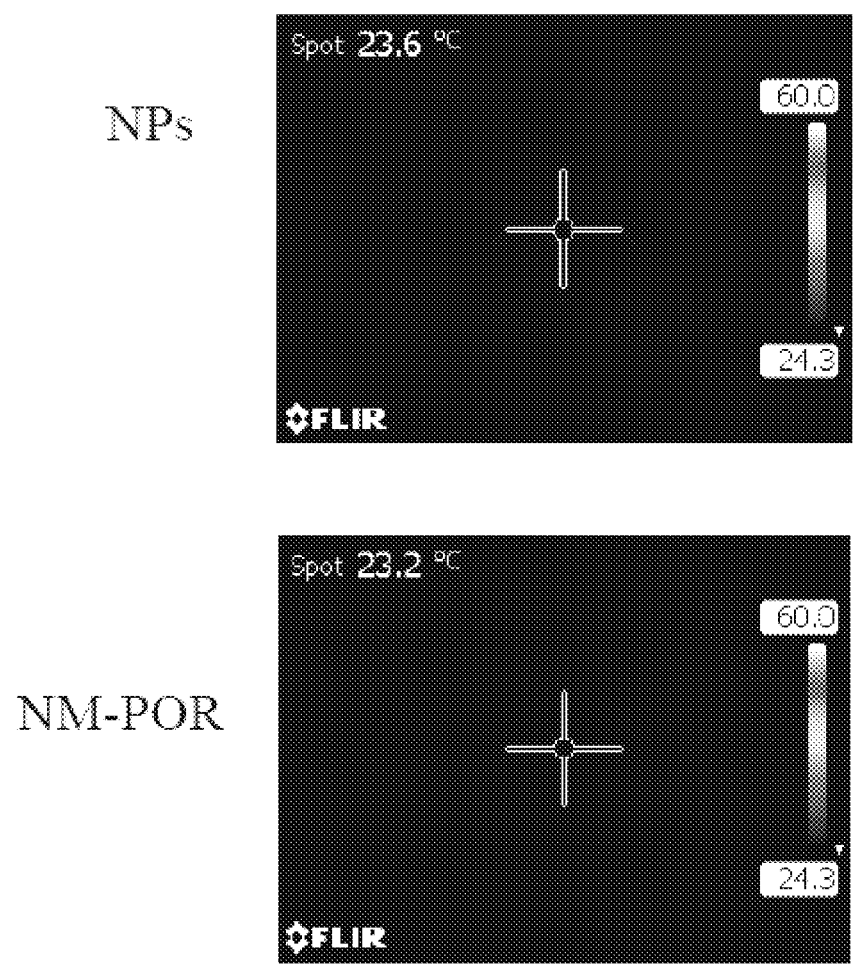
FIG. 35 shows the temperature of blood drops drawn from nude mice bearing implanted tumor xenografts 5 min post-injection of disulfide crosslinked NPs and NM-POR (Por dose: 5 mg/kg) after light exposure. Light dose: 0.1 W for 300 seconds. The temperature was monitored by a thermal camera.
Figure 36:
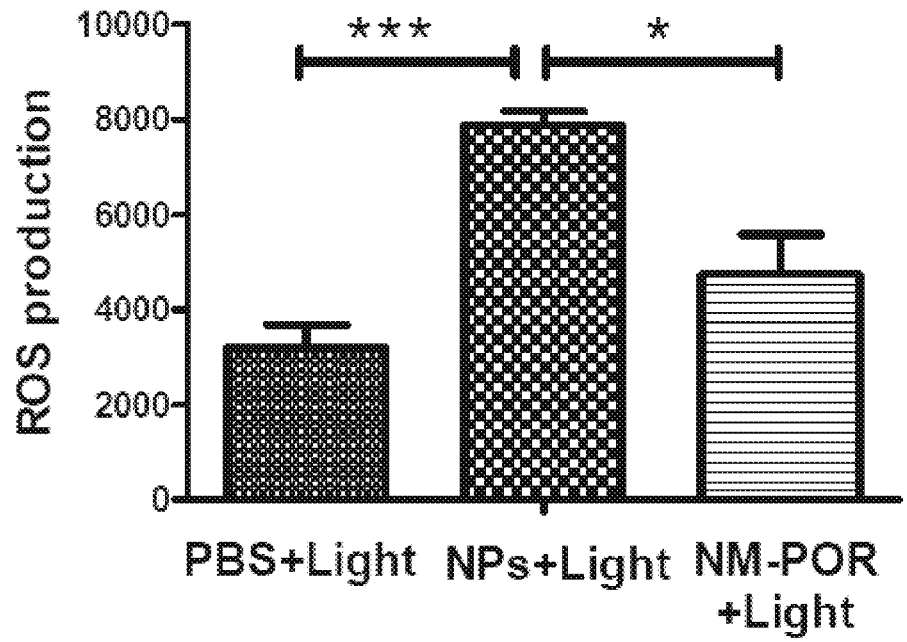
FIG. 36 shows ROS production at tumors of nude mice bearing implanted tumor xenografts 24 hrs post-injection of PBS and disulfide-crosslinked NPs or NM-POR (Por dose: 5 mg/kg) after light exposure (n=5). Light dose: 1.25 W/cm$^2$ for 120 seconds. Measured by using 2',7'-dichlorofluorescin diacetate (DCF) as a ROS indicator. *p<0.01, ***p<0.001.
Figure 37:
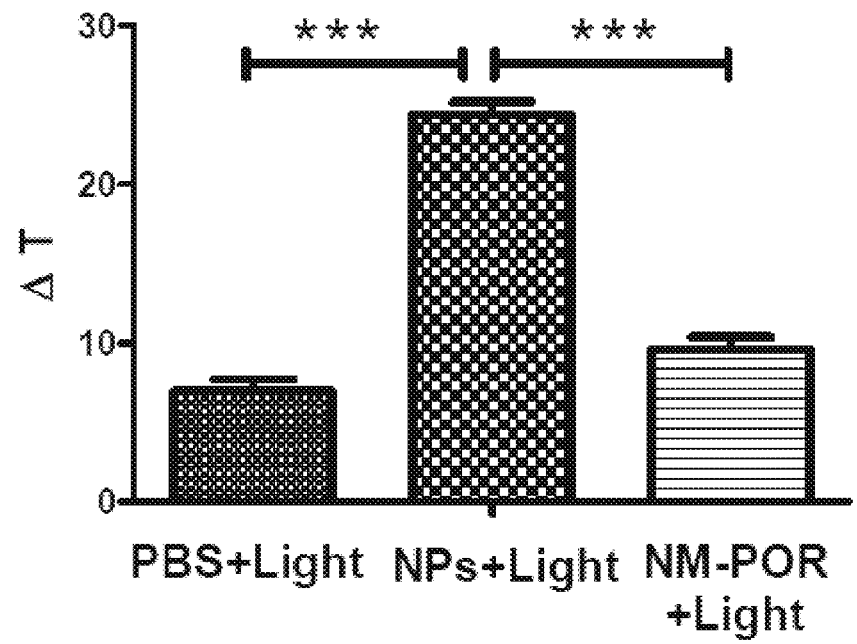
FIG. 37 shows the temperature changes (ΔT) at tumors of nude mice bearing implanted tumor xenografts 24 hrs post-injection of PBS, disulfide crosslinked NPs and NM-POR (Por dose: 5 mg/kg) after light exposure (n=5). Light dose: 1.25 W/cm$^2$ for 120 seconds. The temperature was monitored by a thermal camera. ***p<0.001.
Figure 38A:
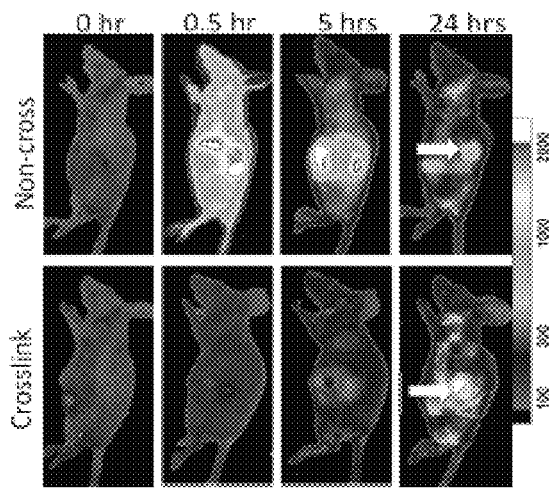
FIG. 38A shows representative in vivo NIRF imaging of SKOV-3 ovarian cancer xenograft following intravenous injection of non-crosslinked and disulfide-crosslinked NPs (NP dose: 25 mg/kg). The white arrow points to the tumor site.
Figure 38B:
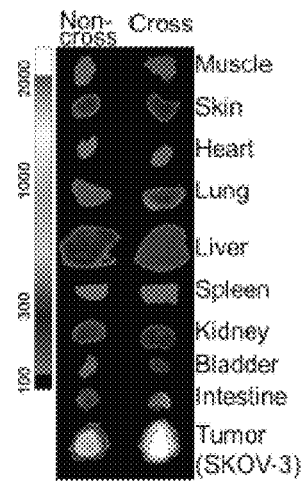
FIG. 38B shows representative ex vivo NIRF imaging of SKOV-3 ovarian cancer xenograft 24 hrs post-injection of non-crosslinked (left) and disulfide-crosslinked (right) NPs.
Figure 38C:
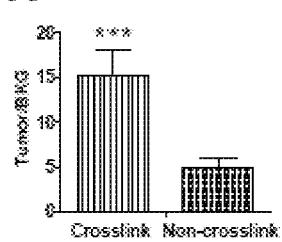
FIG. 38C shows quantitative NIRF fluorescence in tumor SKOV-3 at 24 hrs post-injection of non-crosslinked and disulfide-crosslinked NPs (n=4; NP dose: 25 mg/kg), wherein images were analyzed as the average signal in the region of interest (ROI) in tumor and normalized to muscle (***p<0.001).
Figure 38D:
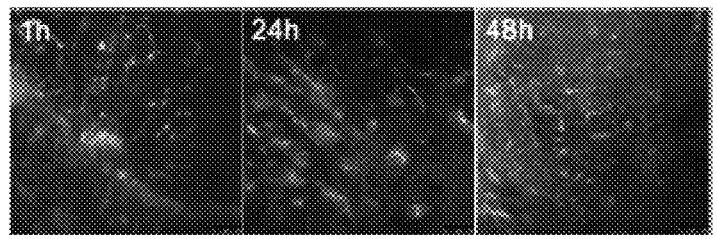
FIG. 38D shows projection images of the distribution of the disulfide-crosslinked NPs in SKOV-3 tumor at 1, 24, 48 hrs post injection observed by large-scale-imaging (LSI) laser scanning confocal microscope, with NPs imaged in red and dextran-FITC labelled tumor blood vessel imaged in green (bar=100 μm).

Here we demonstrated in vivo for the first time, to the best of our knowledge, that the "soft" organic NPs could be used as a smart nanotransducer that could stay inactive in blood circulation but be activated to release heat and ROS at tumor site for simultaneous PTT/PDT using a portable, single wavelength NIR laser. The fluorescence of crosslinked NPs stayed quenched in blood after intravenous injection into mice bearing implanted tumor xenograft (FIG. 32A-32C). Similarly, the ROS production of crosslinked NPs in blood was also minimal upon exposure with low dose of light (similar to the sun light at 690 nm received in daily life, 0.1 W/cm$^2$) (FIG. 33). No obvious hemolysis was observed for crosslinked NPs in blood after light exposure (FIG. 34A-34D). The heat generation of crosslinked NPs was also negligible after exposure to the same dose of light (FIG. 35). To the contrary, NM-POR, the Por encapsulated conventional PEG$^{5k}$-CA$_8$ micelles, presented 5 times higher fluorescence in blood of the mice than crosslinked NPs and produced significantly higher amount of ROS resulting in severe hemolysis (FIG. 32A-34D). This is likely due to the less quenching effect of Por molecules when physically encapsulated inside micelles (FIG. 23). The tumors were irradiated with therapeutic dose of light (1.25 W/cm$^2$ for 120 s) 24 hrs post-injection of PBS, crosslinked NPs and NM-POR. NPs were found to generate significantly higher amount of ROS and caused 2.5 times temperature change at tumor site compared with NM-POR (FIG. 36, FIG. 37). The simultaneous ROS and heat generation of NPs at tumor site could be attributed to the significant accumulation of NPs at tumor sites and partial dissociation at 24 hrs post-injection (FIG. 38D). Based on the results in FIG. 12I, FIG. 12J, the intact NPs are expected to be activated to generate heat while the dissociated NPs could be activated to produce ROS upon light irradiation. The above results suggested architecture dependent photonic properties of NPs could be utilized to minimize the unintended toxicity of photosensitizers in blood and deliver significantly higher amount of ROS and heat to tumor than comparable nanocarriers.

Example 6. Treatment of Human Ovarian Cancer and Bladder Cancer Cells

SKOV-3 human ovarian cancer cell lines and 5637 human bladder cancer cell lines were purchased from ATCC and maintained with the recommended medium. The dog bladder cancer cell line, K9TCC-Pu-In, was originally developed and directly provided by Dr. Deborah Knapp at Purdue University in July, 2009. These cell lines were tested and authenticated using the morphology, immunohistochemistry, gene expression and tumorigenicity assays in Dr. Knapp's lab in 2009. Because these cells were obtained directly from Dr. Knapp, who performed cell line characterizations, and passaged in the user's laboratory for less than 6 months after resuscitation, re-authorization was not required.

Cell Uptake of Nano-Porphyrins

The cancer cells were seeded in eight-well tissue culture chamber slides (BD Biosciences, Bedford, Mass., USA), followed by 24 h of incubation in cell culture medium containing 10% FBS. The medium was replaced, and nano-porphyrin micelles were added to each well. At pre-determined time points, the cells were washed three times with PBS, fixed with 4% paraformaldehyde and the cell nuclei were stained with DAPI. The slides were mounted with cover slips and observed by a DeltaVision imaging system (AppliedPrecision, CA) per manufacturer's protocol.

In another set of experiments, canine urothelial cells were cultured in the complete medium (10% FBS in RPMI1640 with antibiotics) for 3 days until 60% confluence. Human bladder cell line 5637 was pre-stained with DiO (400 nM) for 20 minutes and co-cultured in the same plate with urothelial cells overnight. 2.2 µM of PLZ4-NP was added and cell imaging was acquired by a DeltaVision imaging system.

Example 7. In Vitro Photodynamic Therapy (PDT)

K9TCC-Pu-In and 5637 bladder cancer cell lines and SKOV-3 ovarian cancer cell lines were used to evaluate the photosensitizing function of nano-porphyrins. We first treated the cancer cells with 2.2 µM nano-prophyrins for 2 hr. After thorough washing, the cells were exposed to red light (650 nm). Cell viability was determined using WST-8 proliferation kit (Caymen) 24 hr after illumination. 5-aminolevulinic acid (5-ALA), the traditional photodynamic diagnosis/therapy agent, was used as a control. In another experiments, DOX loaded nanoporphyrins were used to treat the cancer cells followed by light exposure. The cells were also treated with telodendrimers and empty crosslinked micelles with different dilutions and incubated for total 72 h in the absence of light exposure in order to evaluate the dark toxicity and telodendrimer related toxicity.

Animal and Tumor Xenograft Model

Female athymic nude mice (Nu/Nu strain), 6-8 weeks age, were purchased from Harlan (Livermore, Calif.). All animals were kept under pathogen-free conditions according to AAALAC guidelines and were allowed to acclimatize for at least 4 days prior to any experiments. All animal experiments were performed in compliance with institutional guidelines and according to protocol No. 07-13119 and No. 09-15584 approved by the Animal Use and Care Administrative Advisory Committee at the University of California, Davis. The subcutaneous xenograft model of ovarian cancer was established by injecting $7 \times 10^6$ SKOV-3 ovarian cells in a 100 µL of mixture of PBS and Matrigel (1:1 v/v) subcutaneously into the right flank of female nude mice.

Establishment of patient-derived xenografts: The animal protocol was approved by the UC Davis Institutional Animal Care and Use Committee (IACUC) before experiments were performed. To establish subcutaneous patient-derived xenografts (PDX), NOD SCID gamma (NSG; The Jackson Laboratory, West Sacramento, Calif.) 4-5 week-old mice were used. Fresh, unmanipulated clinical tumor fragments (3-5 mm$^3$) were loaded into a trochar with sterile forceps. The loaded trochar was then gently pushed into the flank skin and the trochar plunger was depressed to eject the tumor fragments. The trochar was gently removed and the injection area was sterilized.

To generate an orthotopic xenograft model in NSG mice, a passage #1 PDX specimen was harvested and cut into small pieces. After treated with 1 ml of Accutase (Innovative Cell Technology, San Diego, Calif.) for 30 minutes at 37° C., single cell suspensions were obtained after filtering through cell strainers (BD Falcon, Canaan, Conn.) to remove larger tissues. Cells in 5-10 µl PBS were then injected into mouse bladder walls while visually locating the bladder under general anesthesia. Mice were monitored every day after the surgery.

Example 8. Biodistribution of the Nano-Porphyrins

K9TCC-Pu-In and 5637 bladder cancer and SKOV-3 ovarian cancer xenograft mice models with subcutaneous tumor of an approximate 8-10 mm diameter were subjected to in vivo NIRF optical imaging. At different time points post injection of nano-porphorin micelles, mice were scanned using a Kodak multimodal imaging system IS2000MM with an excitation bandpass filter at 625 nm and an emission at 700 nm. The mice were anaesthetized by intraperitoneal injection of pentobarbital (60 mg/kg) before each imaging. After in vivo imaging, animals were euthanized by $CO_2$ overdose at 24, 48 and 72 h after injection. Tumors and major organs were excised and imaged with the Kodak imaging station.

NIRF imaging studies was performed in the orthotopic xenograft model in NSG mice. Briefly, female NSG mice bearing orthotopic human bladder cancers or normal NSG mice were intravesically injected with 30 µl of PLZ4-NP via urethra under general anesthesia. After 2 hr of incubation, the bladder was isolated for whole body in vivo imaging using Kodak imaging system.

Example 10. NPs Mediated Multimodal Imaging

Methods

Animal Models.

Female athymic nude mice (Nu/Nu strain), 6-8 weeks age, were purchased from Harlan (Livermore, Calif.). Those mice were known to spontanously developed mammary cancers at ages of 4-40 months. All animals were kept under pathogen-free conditions according to AAALAC guidelines and were allowed to acclimatize for at least 4 days prior to any experiments. All animal experiments were performed in compliance with institutional guidelines and according to protocol No. 07-13119 and No. 09-15584 approved by the Animal Use and Care Administrative Advisory Committee at the University of California, Davis. The subcutaneous xenograft model of ovarian cancer was established by injecting $2 \times 10^6$ SKOV-3 ovarian cells or A549 lung cancer cells in a 100 µL of mixture of PBS and Matrigel (1:1 v/v) subcutaneously into the right flank of female nude mice. Transgenic mice with mammary cancer (FVB/n Tg(MMTV-PyVmT)) were ordered from Jackson Laboratory.

NIRF Optical Imaging.

After transgenic mice (10-12 weeks) and nude mice developed established tumors (6-10 mm in diameter), they were subjected to in vivo NIRF optical imaging by injecting 100 µL of NPs via tail vein. At different time points post-injection of NPs, mice were scanned using a Kodak multimodal imaging system IS2000MM with an excitation bandpass filter at 625/20 nm and an emission at 700/35 nm under anaesthesia. After in vivo imaging, animals were euthanized. Tumors and major organs were excised and imaged with the Kodak imaging station. To monitor the kinetics of biodistribution at the tissue level, SKOV-3 tumor-bearing mice were given 100 µL of crosslinked NPs via tail vein and euthanized at 1, 24, or 48 hrs. Right before euthanasia, Dextran-FITC solution was injected intravenously to locate blood vessel. Tumors were harvested and fixed in the cold formalin on ice. A fresh cross-section was made for Large-Scale-Imaging (LSI) laser scanning confocal microscope imaging. Additionally, lungs with metastatic lesions were also collected from older transgenic mice (20-24 weeks) and fixed in cold formalin for one hour. The lung surface was imaged by LSI laser scanning confocal microscopy. After imaging, lungs were subjected to histopathological evaluation. In some cases, the blood of the mice were drawn and measured at predetermined time points.

MRI and PET Imaging.

The in vitro MRI signal enhancement of Gd-NPs in the absence and in the presence of SDS was obtained using a Bruker Biospec 7T MRI scanner using T1-weighted Fast Low Angle SHot (FLASH) sequence (echo time (TE)/repetition time (TR)=4/200 ms) using a 128×128 matrix size. Nude mice bearing SKOV-3 ovarian cancer xenograft, nude mice bearing A549 lung cancer xenografts and transgenic mice with mammary cancer (FVB/n Tg(MMTV-PyVmT) were imaged on a Bruker Biospec 7T MRI scanner. Spin echo images were acquired to determine solid tumor location and volume. To assess the kinetics of the Gd-NPs in the body and tumor as well as the nanoparticle-enhanced MRI signal intensity, a dynamic T1-weighted FLASH sequence was used to acquire images just before injection and at predetermined time points post-injection of Gd-NPs (Gd dose: Gd dose: 0.015-0.02 mmole/kg) (TE/TR=4/200 ms) using a 128×128 matrix size. MRI was also used to monitor the tumor growth in nude mice bearing SKOV-3 ovarian cancer xenografts before and after PTT/PDT using the same parameters. PET was performed on nude mice bearing SKOV-3 ovarian cancer xenografts post-injection of $^{64}$Cu-labeled NPs (150-200 μL, $^{64}$Cu dose: 0.6-0.8 mCi) on a small-animal microPET system (Siemens Inveon D-PET). PET-MRI was performed on a small-animal microPET system (Siemens Inveon D-PET) and a Bruker Biospec 7T MRI scanner. Nude mice bearing A549 lung cancer xenografts were placed on a movable bed that fits into both scanners in order to facilitate co-registration of the PET and MR images. After tail vein injection of $^{64}$Cu and Gd dual-labeled NPs (150-200 μL, $^{64}$Cu dose: 0.6-0.8 mCi, Gd dose: 0.015-0.02 mmole/kg), the mice were imaged under anesthesia (2% isoflurane in oxygen at 2 L/min) at 4 or 24 hrs post-injection. Amide software was used to co-register the PET and MR images.

Results

Figure 39:
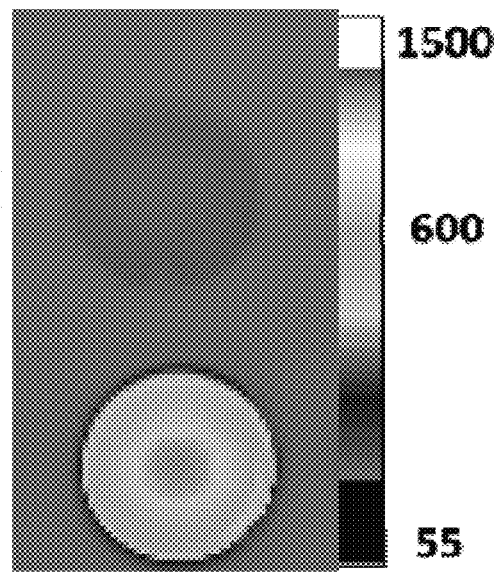
FIG. 39 shows a representative NIR fluorescence signal of blood drops drawn from xenograft tumor model 5 min post-injection of disulfide-crosslinked NPs (Por dose: 5 mg/kg) in the absence and in the presence of SDS and GSH (10 mM).

The particle size of NPs and disulfide crosslinked NPs is around 20-30 nm (FIG. 12C, FIG. 16B), which is an optimal range for tumor targeting and penetration[11,14,20] On the basis of their reversibly crosslinking nature and unique architecture-dependent fluorescence property, crosslinked NPs are particularly suitable to be used as activatable optical nanoprobes to increase the sensitivity of NIRFI for improved cancer detection through background suppression in blood, preferential accumulation and signal amplification at tumor site. The crosslinked NPs could stay silent (or in the OFF state) with minimum background fluorescence signals in blood circulation (FIG. 38A, lower panel). The quenching status of crosslinked NPs in blood was further demonstrated by the recovery of fluorescence via the addition of SDS and GSH (FIG. 39). As expected, the overall fluorescence signal in the whole body was drastically lower for crosslinked NPs than the non-crosslinked NPs after intravenous injection in SKOV-3 ovarian cancer mouse model (FIG. 38A). Upon accumulation at tumor site via size-mediated enhanced permeability and retention (EPR) effect, these crosslinked nanoprobes could be turned ON via the cleavage of disulfide bonds by endogenous reducing agent GSH at tumor site or in cancer cells, followed by micellar dissociation and amplification of fluorescence signal. Crosslinked NPs showed significantly higher tumor accumulation than non-crosslinked NPs at 24 hrs post-injection (FIG. 38A). Ex vivo imaging at 24 hrs post-injection showed both non-crosslinked and crosslinked NPs had superior fluorescence signal in tumors compared to normal organs (FIG. 38B). The average fluorescence of crosslinked NPs at tumor site was 15 times higher than that in muscle of the same group of mice and 3 times higher than that of non-crosslinked NPs at tumor site (FIG. 38C). The differential fluorescent signal between the crosslinked NPs and non-crosslinked NPs can be explained by the stability of the former construct in the circulation and therefore higher uptake into the tumor.

FIG. 38D shows projection images of the intra-tumoral distribution of the crosslinked NPs (red). The tumor blood vessels (BV) were labelled with Dextran-FITC (green). The overall NIRF signal from NPs was very low inside the tumor tissue at 1 hr post-injection (FIG. 38D, left). Significant NIRF signal was observed surrounding the blood vessels (green) at 24 hrs (FIG. 38D, middle), indicating the accumulation and partial dissociation of NPs into tumor tissue around BV. At 48 hrs, NPs signals diffusedly distributed throughout the entire tumor implying their excellent tissue penetration and dissociation ability (FIG. 38D, right). These results proved to be invaluable in guiding the design of the following photo-therapy studies in animal models.

Figure 38E:
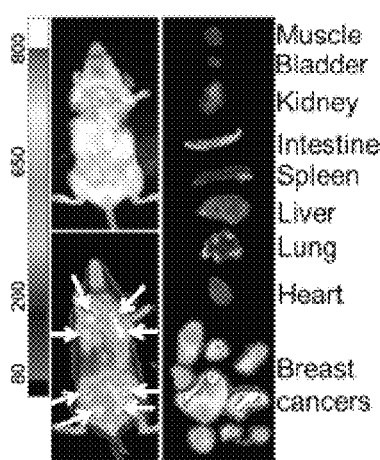
FIG. 38E shows representative in vivo and ex vivo NIRF light images of transgenic mice with mammary cancer (FVB/n Tg(MMTV-PyVmT) at 24 hrs post-injection of disulfide-crosslinked NPs (NP dose: 25 mg/kg)
Figure 38F:
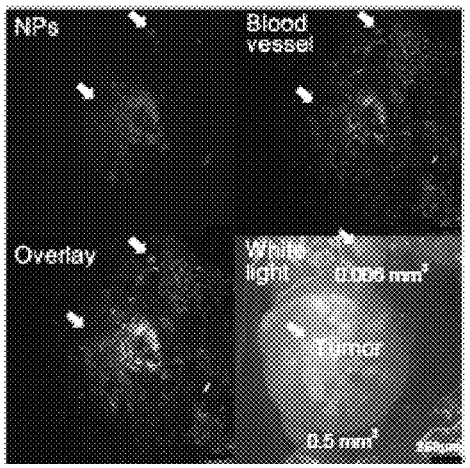
FIG. 38F shows the accumulation of NPs in lung metastasis of breast cancer in transgenic mice at 24 hrs post injection observed by LSI laser scanning confocal microscope.
Figure 40:
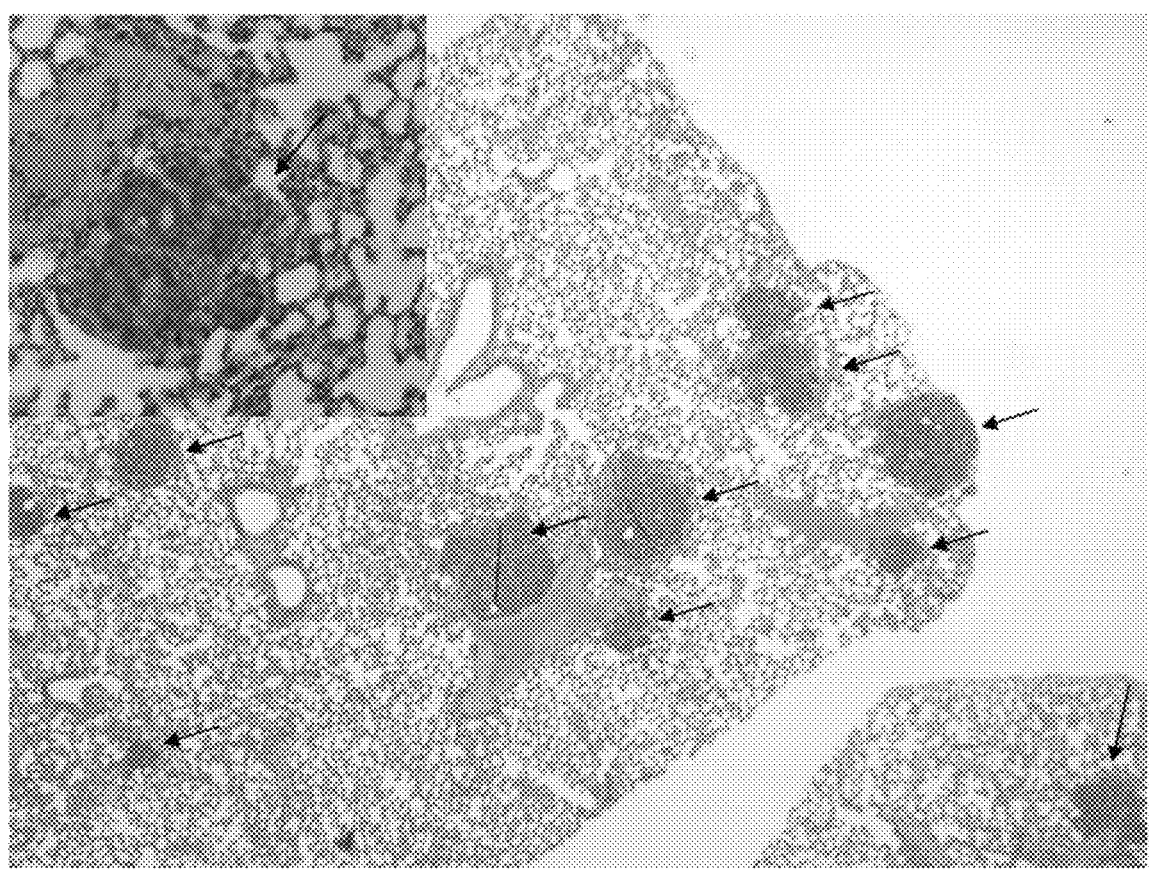
FIG. 40 shows histopathological imaging confirming the metastatic lesions (arrows) in lungs of breast cancers from the transgenic mice (FVB/n Tg(MMTV-PyVmT). (H&E stain, 4× and insertion 40×).

We then investigated the NIRFI capability of crosslinked NPs in transgenic mice (10-12 weeks) with naturally occurring breast cancers (FVB/n Tg(MMTV-PyVmT)) through intravenous injection. Since these transgenic mice spontaneously develop multiple breast cancers with different sizes, and both the tumor cells and the endothelial cells are derived from the same mouse, there is no concern of tumor vasculature artifact that may occur in syngeneic or xenogeneic tumor implant models. After 24 hrs, high fluorescence was observed in all the spontaneous breast cancers (FIG. 38E), as NPs accumulated in the tumors and inside the tumor cells, they dissociated and became unquenched. In FIG. 38E, the white arrows point to the tumor site. Tumor volume was calculated by $(L*W^2)/2$, where L is the longest, and W is the shortest tumor diameter (mm). Ex vivo imaging further confirmed the preferential uptake of the NPs in all the nine excised breast tumors compared to normal organs after 24 hrs. It should be mentioned that even small tumors (around 18 mm$^3$ in volume) at the mammary fat pad have very strong NIRF signal from NPs (FIG. 38E), indicating NPs could be potentially used for the detection of early stage breast cancers. We then investigated the distribution of NPs in older transgenic mice (20-24 weeks) using a Large-Scale-Imaging (LSI) laser scanning confocal microscope and successfully located the tiny focal accumulation of metastatic lesions (around 0.006 mm$^3$ and 0.5 mm$^3$ in volume) in the lung (FIG. 38F, FIG. 40). In FIG. 38F, the white arrow points to the metastatic site. Red: nanoporphyrins; Green: Dextran-FITC labelled tumor blood vessel (bar=250 μm). These results indicate NPs may offer a great opportunity to detect primary tumors as well as small metastatic lesions.

Figure 41A:
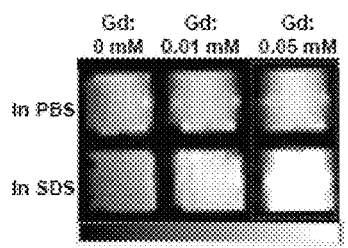
FIG. 41A shows in vitro MRI signal of Gd-NPs in the absence and in the presence of SDS obtained by T1-weighted MR imaging on a Bruker Biospec 7T MRI scanner using a FLASH sequence.
Figure 41B:
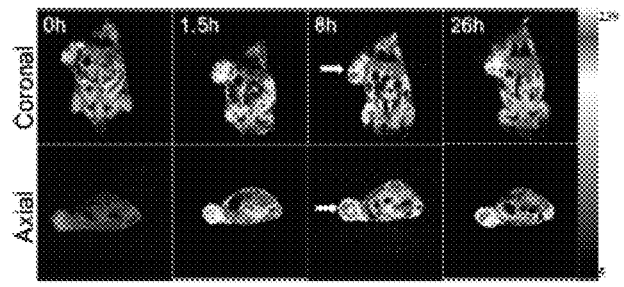
FIG. 41B shows representative coronal and axial MR images of transgenic mice with mammary cancer (FVB/n Tg(MMTV-PyVmT) using a FLASH sequence pre-injection and after injection of 0.15 mL Gd-NPs (Gd dose: 0.015 mmole/kg). The white arrow points to the tumor site.

The NPs have intrinsic ability to chelate Gd(III) (FIG. 12D, FIG. 12F) and possess architecture-dependent magnetic resonance property which allow them to be used as activatable contrast agents for sensitive and tumor-specific MRI. Similar to the fluorescence measurements in FIG. 12G, FIG. 12H, there is minimal MRI signal enhancement when the Gd-NPs retain their integrity in PBS (FIG. 41A). This is likely due to the stacking of Gd/Por at the interface between the hydrophobic core and hydrophilic corona (FIG. 12F), thus shielding Gd(III) from interacting with protons in water. Upon dissociation in SDS, the Gd ion chelated by the Por has access to shorten the spin-lattice relaxation time of nearby protons, resulting in an enhancement in MRI signal (FIG. 41A). This unique architectural feature of Gd-NPs offers opportunity for sensitive MRI detection of tumor as the background signal of the circulating NPs is low. We validated the application of Gd-NPs for MRI in transgenic mice with "spontaneous" mammary cancer. A set of representative slices at different time point post-injection is shown in FIG. 41B. We demonstrated that Gd-NPs could significantly enhance the contrast of tumor at 1.5 hrs post-injection with very low signal enhancement in the normal tissue. The tumor contrast was sustained for more than 26 hrs. Doses of Gd used in these studies were equivalent to ⅕th of the clinically recommended Gd dose for human[21]. These results confirm that the MRI signal enhancement in the whole body is low when the Gd-NPs are circulating in blood pool. After reaching the tumor site or tumor cells, the Gd-NPs dissociates and allows the interaction of Gd ions with surrounding protons, resulting in the significant MRI contrast only at tumor site (FIG. 12B).

Figure 41C:
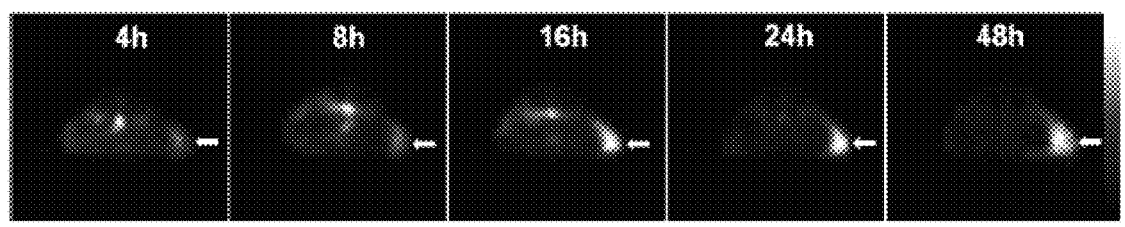
FIG. 41C shows a PET image of nude mice bearing SKOV-3 ovarian cancer xenografts at 4, 8, 16, 24, 48 hrs post-injection of $^{64}$Cu-labeled NPs (150-200 μL, $^{64}$Cu dose: 0.6-0.8 mCi), wherein the white arrow points to the tumor site.
Figure 42:
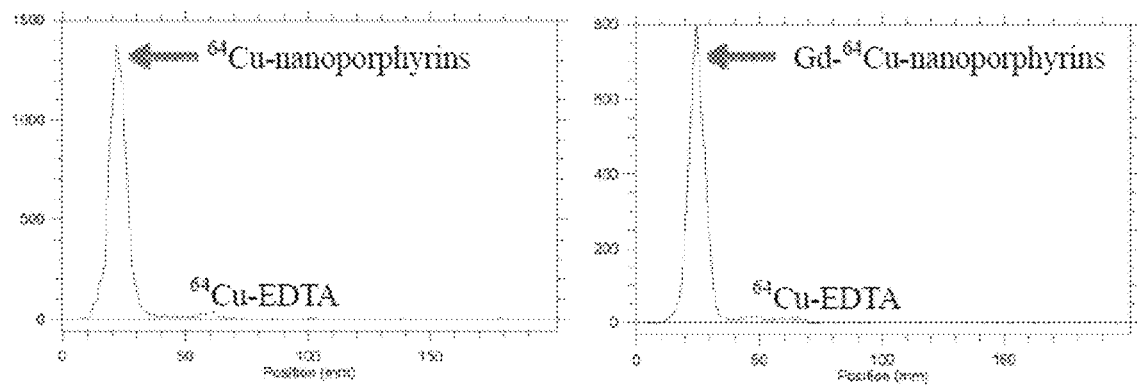
FIG. 42 shows instant thin-layer chromatography (ITLC) traces of $^{64}$Cu-nanoporphyrins (left panel) and Gd-$^{64}$Cu-nanoporphyrins (right panel) post-centrifuge filtration. The radiochemical yields (RYC) is above 96.5% while the radiochemical purity is above 97%. ITLC Method: Biodex strips developed in 90 mM EDTA/0.9% NaCl (aq), imaged on Bioscan plate reader.

Furthermore, NPs have intrinsic capacity to incorporate radiotracers for applications as PET nanoprobes. For instance, we have incorporated of a radiotracer ($^{64}$Cu(II)) into NPs for PET imaging through a simple, fast, one-pot, high yielding radiolabeling strategy (radiochemical yields (RYC)>96.5%) (FIG. 12D, FIG. 42). It is the intrinsic ability of NPs to directly chelate $^{64}$Cu(II) that allows not only their biodistribution but also pharmacokinetics to be noninvasively tracked in vivo by PET (FIG. 41C). PET imaging showed that $^{64}$Cu-nanoporphyrins started to accumulate at tumor sites from 4 hrs post-injection, reached maximum levels at 16 hrs. After 24 hrs, the radiolabel was found primarily at the implanted tumors, with very low background in rest of the body (FIG. 41C). Even though we have not performed here, chelation and cancer-specific delivery of $^{67}$Cu can potentially be used for systemic in situ radiotherapy.

Figure 41D:
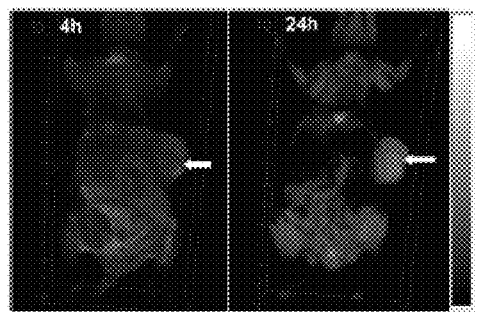
FIG. 41D shows 3D coronal MR images of nude mice bearing A549 lung cancer xenografts using a FLASH sequence at 4 or 24 hrs post-injection with 0.15 mL of $^{64}$Cu and Gd dual-labeled NPs (150-200 μL, $^{64}$Cu dose: 0.6-0.8 mCi, Gd dose: 0.015 mmole/kg), wherein the white arrow points to the tumor site.
Figure 41E:
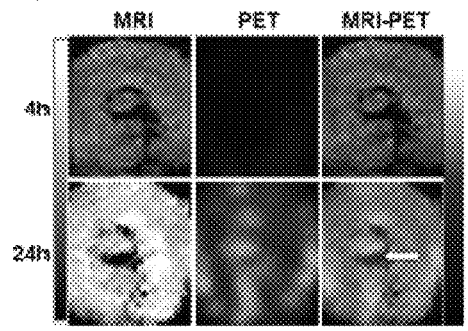
FIG. 41E shows PET-MR images of tumor slices of nude mice bearing A549 lung cancer xenograft at 4 or 24 hrs post injection of dual-labeled NPs, wherein the white arrow indicates the necrotic area in the center of the tumor.

The synergistic combination of PET and MRI is likely to become the next generation of dual-modality scanners to provide accurate diagnoses[22,23]. Consequently, there is a great need to develop dual-modality agents that can take advantage of the complementary strengths of PET (high sensitivity and quantifiability) and MR (high soft-tissue resolution) imaging[24-26]. As an exogenous-chelator-free nanoplatform that possesses intrinsic capacity to chelate Gd(III) and radiotracers simultaneously, NPs show significant promise for development as dual-modality nanoprobes for PET-MRI. We have shown both $^{64}$Cu(II) and Gd(III) could be efficiently incorporated into NPs (FIG. 12D, FIG. 42). Dual-labeled NPs could significantly enhance the MRI contrast and PET signal at the tumor site at 24 hrs post-injection (FIG. 41D, FIG. 41E). Interestingly, the heterogeneity of the tumor and the inhomogeneous distribution of NPs in the tumor were non-invasively revealed by PET-MRI (FIG. 41E).

Example 10. NPs Mediated Multimodal Therapy

Methods

In Vivo Therapeutic Studies.

Transgenic mice with mammary cancer (FVB/n Tg(MMTV-PyVmT) and nude mice bearing SKOV-3 ovarian cancer xenograft were used for the in vivo therapeutic studies. When tumor volumes reached 4-5 mm in transgenic mice, crosslinked NPs with and without 2.5 mg/kg DOX were injected via tail vein once per week for 3 doses. After 24 hrs, tumors were illuminated with a diode laser system (Applied Optronics, Newport, Conn.) at 690 nm under general anaesthesia. The light dose was 1.25 W cm$^{-2}$ for 2 minutes through an optical fiber producing a 0.8 cm$^2$ beam spot to cover the whole tumor. Tumor temperatures were recorded with an infrared camera (Flir). Intratumoral ROS production after irradiation was measured using 2',7'-dichlorofluorescin diacetate (DCF) mixed with 100 μL of tissue lysates derived from tumors treated with NPs and PBS. In some cases, the blood of the mice was drawn and the ROS and heat production in blood after irradiation were measured at predetermined time points. The hemolysis was also followed. Tumor volume was measured twice a week and mice were sacrificed once tumor size reached 1000 mm$^3$. Tumors were harvested for histopathological evaluation 24 hours post-irradiation. The SKOV-3 ovarian cancer xenograft model was established by injecting one million cells subcutaneously at lower flank area. After tumors reached 150-200 mm$^3$, mice received PBS, 2.5 mg/kg DOX, and crosslinked NPs with and without 2.5 mg/kg DOX every 3 days for 3 doses. 0.2 W cm$^{-2}$ of laser light was given for 2 min after dose 1 and 3. Tumor sizes and body weight were measured twice a week, while mice were monitored daily for potential signs of toxicity. Two days after the last dose, CBC and serum chemistry were performed. One mouse from each group was also sacrificed and major organs were harvested for histopathology evaluation.

Statistical analysis. Statistical analysis was performed by Student's t-test for two groups, and one-way ANOVA for multiple groups. All results were expressed as the mean±standard error (SEM) unless otherwise noted. A value of $P<0.05$ was considered statistically significant.

Results

Light-based techniques such as PDT and PTT may offer promising opportunities for cancer treatment[27-36]. The clinical use of photo-therapy has been hampered by 1) photosensitizers have poor selectivity between tumor and normal tissues, resulting in limited efficacy and photo-toxicity to normal tissue[37-41]; 2) photo-therapy mediated oxidative stress induces the expression of pro-survival and angiogenic signalling molecules such as survivin, Akt, hypoxia inducible factor 1α (HIF-1α), matrix metalloproteinase-2 (MMP-2) and vascular endothelial growth factor (VEGF) in tumor microenvironment which can negatively impact treatment effectiveness and lead to tumor reoccurrence[27,42,43]. Nanocarriers such as micelles and liposomes have been used for targeted delivery of photosensitizers to tumor for phototherapy[6,44]. However, in vivo results have shown that the tumor targeting specificity of these nanocarriers was not as good as expected probably due to the in vivo instability and non-specific targeting in normal tissue[44]. Most recently, a novel class of organic porphysome nanovesicles[6] has been reported as multifunctional biophotonic agents to efficiently transduce light to heat for PTT. Unfortunately, porphysomes tend to have high liver and spleen accumulation in part due to their relatively large size (~100 nm), resulting in non-specific clearance by the reticuloendothelial system (RES)[11,14,20]. In contrast, cross-linked NPs showed extremely low liver and spleen uptake and high tumor targeting specificity (FIG. 38B, FIG. 38C). It is expected that crosslinked NPs could be used to minimize the photo-toxicity of the photosensitizers and greatly enhance the efficacy of photo-therapy.

There have been studies showing that PTT has synergistic effect with PDT and could enhance the outcome of PDT and chemotherapy by increasing local permeability of the sensitizer and drugs[33,45,46]. Several inorganic nanoparticle complexes, such as photosensitizer conjugated gold nanorod[33], graphene oxide nanoparticles[45] and silica-coated palladium/silver nanoparticles[46], have been developed for PTT/PDT dual therapy. However, the synthesis of these complexes is complicated and the activation of these nanoparticles required two separate irradiations using multiple-wavelength lasers (e.g. 808 nm and 675 nm)[33,45,46]. There are also concerns regarding the long-term safety of these inorganic nanoparticles.

Figure 43A:
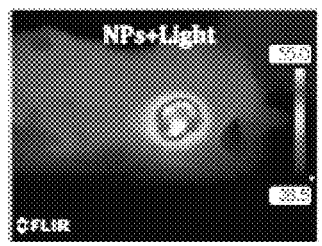
FIG. 43A shows representative thermal images of tumors in transgenic mice with mammary cancer (FVB/n Tg(MMTV-PyVmT) after light irradiation at 24 hrs post-injection of crosslinked NPs.
Figure 43B:
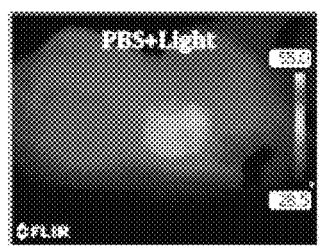
FIG. 43B shows images for mice injected with PBS.
Figure 43C:
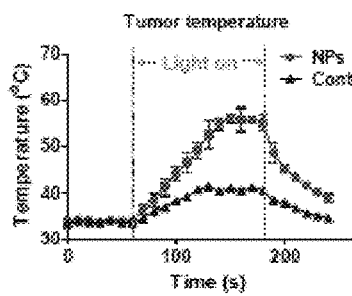
FIG. 43C shows the temperature change in tumors in transgenic mice injected with crosslinked NPs and PBS after irradiation.
Figure 43D:
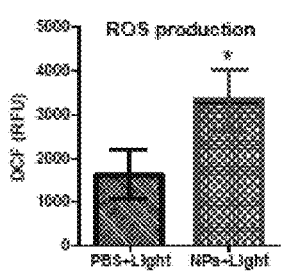
FIG. 43D shows ROS production at tumor sites in transgenic mice treated with crosslinked NPs and PBS (control) for 24 hrs followed by laser irradiation. $p<0.025$.
Figure 43E:
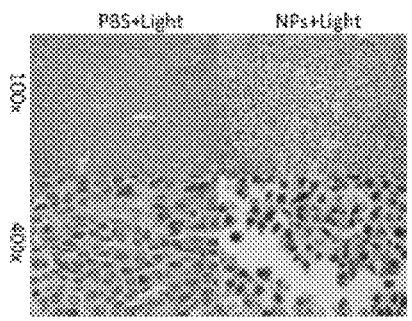
FIG. 43E shows the histopathology of tumors from mice injected with PBS or NPs 24 hrs after irradiation. The light dose was 1.25 W cm$^{-2}$ for 2 min while the NPs dose was 25 mg/kg (equivalent to 5 mg/kg of porphyrin) for FIG. 43a-e.
Figure 44:
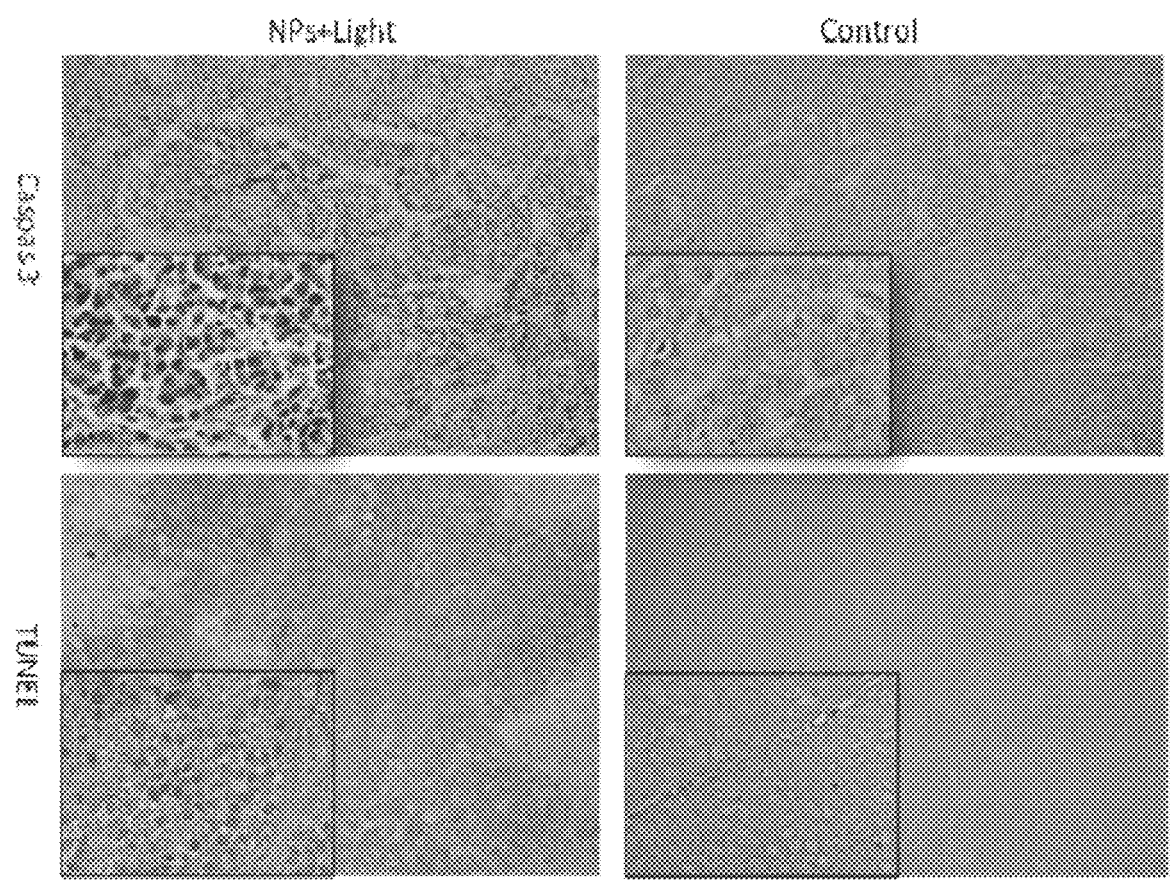
FIG. 44 shows caspase3 reactivity and DNA damage in mammary tumor tissue after NP-mediated PDT. Transgenic mice treated with PBS (control) or NPs followed by light treatment at 24 hours post-injection. DOX dose: 2.5 mg/kg, NP dose: 25 mg/kg (equivalent to 5 mg/kg of Por), light dose: 1.25 W cm$^{-2}$ for 2 min. Tumors were harvested another 24 hours later and fixed in formalin. Tissue slides (4 microns thick) were used to perform IHC for cleaved caspase3. DNA damage was detected using TUNEL (TdT-mediated dUTP Nick-end labeling) detection Kit (GenScript, Piscataway, N.J.) per the manufacturer's manual. Antibody reactivity of cleaved caspase3 (cell signaling) was detected by immunochemistry.

We have also demonstrated that the temperature at the tumor site of transgenic mice increased to 57° C. after light irradiation (1.25 W cm$^{-2}$ for 2 min) 24 hrs post-injection of NPs (FIG. 43A, FIG. 43C). This temperature is sufficient to cause irreversible damage to cancer cells[6]. In contrast, the temperature at the tumor site in the PBS control group only increased to 41° C. with identical light exposure (FIG. 43B, FIG. 43C). The ROS generated by NPs after irradiation was also significantly higher than the tissue background in the PBS control group (FIG. 43D). Histopathology revealed large areas of severe tissue damage, such as cellular destruction and apoptosis at 24 hrs after irradiation (FIG. 43E) evidenced by positive TUNEL results and cleaved caspase3 immuno-reactivity (FIG. 44). Those changes could be attributed to both effects from heat and ROS production (FIG. 43A, FIG. 43C, FIG. 43D).

Figure 43F:
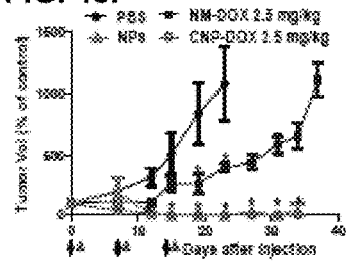
FIG. 43F shows tumor volume change of transgenic mice with mammary cancer (n=8) treated with crosslinked NPs, CNP-DOX and NM-DOX (standard micelles without porphyrin) on day 0, 7, and 14 (black arrow) followed by light exposure on the tumors in the mice in all groups at 24 hrs post-injection (red arrow). $p<0.01$. DOX dose: 2.5 mg/kg, NP dose: 25 mg/kg (equivalent to 5 mg/kg of porphyrin), light dose: 1.25 W cm$^{-2}$ for 2 min.
Figure 43G:
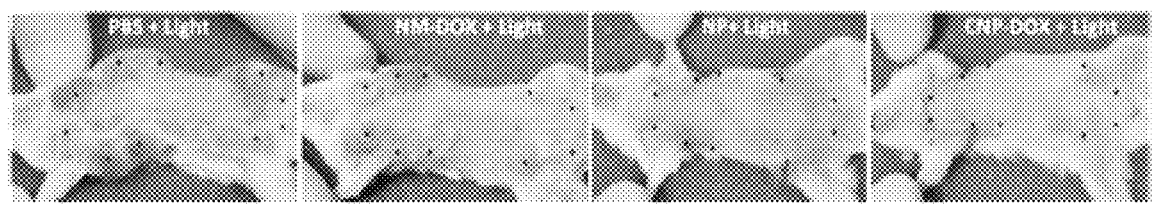
FIG. 43G shows pictures of transgenic mice at day 34 of the treatment. (*: mammary tumors)
Figure 43H:
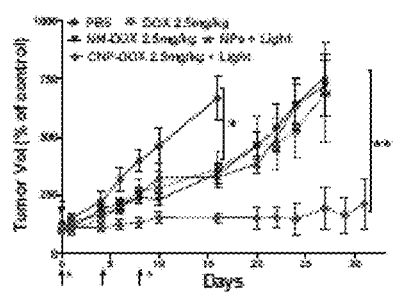
FIG. 43H shows the tumor volume change of mice (n=8) bearing SKOV-3 ovarian cancer xenograft treated with crosslinked NPs and CNP-DOX at day 0, 4 and 8 (black arrow) followed by irradiation on day 1, and 9 (red arrow). PBS and NM-DOX were injected for comparison. DOX dose: 2.5 mg/kg, NP dose: 25 mg/kg (equivalent to 5 mg/kg of porphyrin), light dose: 0.25 W cm$^{-2}$ for 2 min. $p<0.01$.
Figure 45:
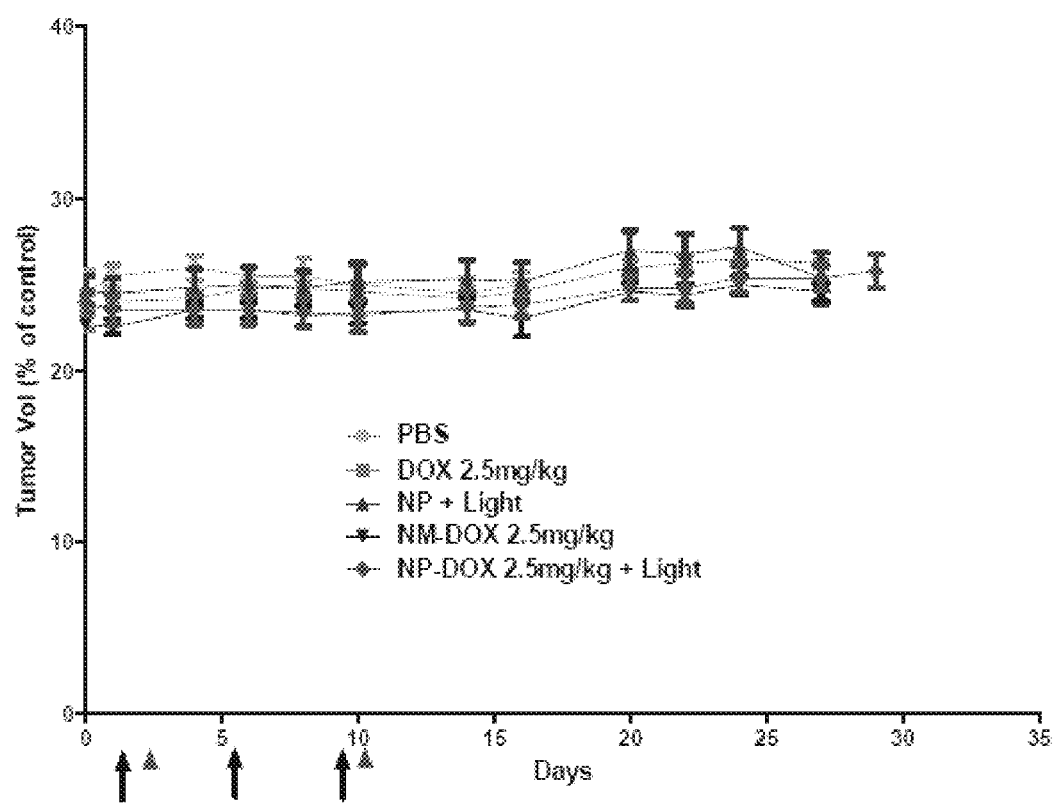
FIG. 45 shows body weight changes of mice bearing SKOV-3 ovarian cancer xenograft (n=8) treated with nanoporphyrins (NPs) and doxorubicin loaded nanoporphyrins (NP-DOX) at day 0, 4 and 8 (arrow axis markers) followed by exposure to laser light (690 nm) on day 1, and 9 (triangle axis markers). PBS and doxorubicin loaded standard micelles (NM-DOX) were injected for comparison. DOX dose: 2.5 mg/kg, NP dose: 25 mg/kg (equivalent to 5 mg/kg of Por), light dose: 0.25 W cm$^{-2}$ for 2 min.

We have shown in FIG. 16A-16H that crosslinked nanoporphyrins could be used as programmable releasing nanocarriers that minimized the drug release in human plasma but could be triggered to release the drug content by light exposure and intracellular reducing agents. Upon irradiation with near-infrared light, drug loaded and crosslinked NPs are expected be activated to release singlet oxygen, heat and drugs simultaneously at the tumor sites for simultaneous PTT/PDT and chemotherapy. We then performed in vivo therapeutic studies to evaluate the anticancer efficacy of crosslinked NPs in transgenic and xenograft mouse models. In the transgenic mouse study, NP-mediated PTT/PDT could significantly inhibit tumor growth with a light dose of 1.25 W cm$^{-2}$ for 2 min once per week when compared to the PBS control group and NM-DOX group. The treated tumors were completely eliminated on day 12 with ulceration (FIG. 43F). No palpable tumors were detected even at day 32 (FIG. 43G). CNP-DOX mediated combination therapy of PTT/PDT with DOX showed similar efficacy (FIG. 43F, FIG. 43G). In order to effectively compare the efficacy of NP mediated combination therapy, we will need to use lower dose of NPs and/or lower dose of light. This will be the subject of future work. Interestingly, in the SKOV-3 ovarian cancer xenograft model, the NP mediated photo-therapy, free DOX and NM-DOX mediated chemotherapy resulted in slower tumor growth in SKOV-3 than PBS control group (FIG. 43H). While administered at same dose of DOX, photosensitizer (porphyrins) and light (0.25 W cm$^{-2}$ for 2 min), CNP-DOX mediated combination therapy showed the best antitumor activity among the groups and totally inhibited tumor growth throughout the study. No significant changes were observed in body weight, complete blood count, and serum chemistry after 3 doses of treatment (FIG. 45 Table 1). Mice were handled without avoiding the ambient light in the laboratory, no skin photo-toxicity were shown.

Figure 43I:
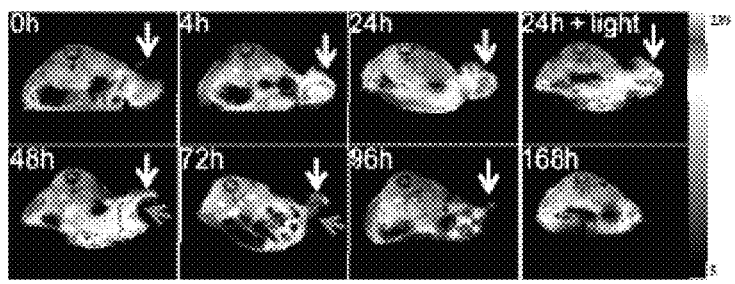
FIG. 43I shows MRI-guided PTT/PDT. Representative MR images of mice injected with Gd-NPs (Gd dose: 0.015 mmole/kg) before and after laser irradiation. White arrows indicate the tumor sites. Images were collected at 0 (pre-injection), 4, 24, 48, 72, 96 and 168 hrs post-injection. MR imaging showed large signal voids (blue arrows) at tumor sites 24 hrs after irradiation (48 hrs post-injection) at a dose of 1.25 W cm$^2$ for 3 min and the tumors were completely ablated at 168 hrs (7 days) post-injection.

Based on the unique imaging capabilities of NPs, non-invasive, real-time imaging strategies taking advantage of the deep tissue penetration of MRI could be utilized to conveniently monitor the simultaneous delivery and detection of NPs as well as their therapeutic efficacy after treatment, including the tumor size and necrosis inside the tumor after PTT/PDT. As a proof of concept, we thus used MRI to observe the tumor growth in SKOV-3 ovarian cancer mice models after administration of Gd-NPs with or without light irradiation (FIG. 43I). MR images showed that Gd-NPs had significant accumulation at tumor site beginning 4 hrs post-injection. For the treatment group, tumors were irradiated at 24 hrs post-injection. MR images at 48 hrs post-injection (24 hrs after irradiation) showed shrinkage of the tumor and increase in necrotic volume at tumor site. MRI showed complete tumor elimination at 7 days post-injection. In contrast, the tumor growth of control mice without irradiation was not affected as revealed by MR images (data not shown).

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A nanocarrier having an interior and an exterior, the nanocarrier comprising a plurality of first conjugates wherein each conjugate is a compound of formula (I):

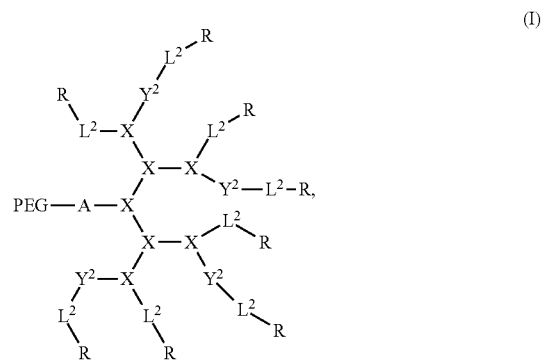

wherein:
    each PEG is a polyethyleneglycol (PEG) polymer having a molecular weight of 1-100 kDa;
    A comprises at least one branched monomer unit X and is linked to at least one PEG group;
    X is independently selected from the group consisting of 2,3-diamino propanoic acid, 2,4-diaminobutanoic acid, 2,5-diaminopentanoic acid (ornithine), 2,6-diaminohexanoic acid (lysine), (2-Aminoethyl)-cysteine, 3-amino-2-aminomethyl propanoic acid, 3-amino-2-aminomethyl-2-methyl propanoic acid, 4-amino-2-(2-aminoethyl) butyric acid and 5-amino-2-(3-aminopropyl) pentanoic acid;
    each Y$^2$ is absent or a crosslinking group independently selected from the group consisting of boronic acid, dihydroxybenzene and a thiol, wherein at least two crosslinking groups are present:
    each L$^2$ is independently a bond or a linker; and
    each R is independently selected from the group consisting of cholic acid, (3α, 5β, 7α, 12α)-7,12-dihydroxy-3-(2,3-dihydroxy-1-propoxy)-cholic acid (CA-4OH), (3α, 5β, 7α, 12α)-7-hydroxy-3,12-di(2, 3-dihydroxy-1-propoxy)-cholic acid (CA-5OH), (3α, 5β, 7α, 12α)-7,12-dihydroxy-3-(3-amino-2-hydroxy-1-propoxy)-cholic acid (CA-3OH—NH$_2$), cholesterol formate, doxorubicin, rhein, and porphyrin,
    wherein at least one R group is a porphyrin,
    wherein each conjugate self-assembles in an aqueous solvent to form the nanocarrier such that a hydrophobic pocket is formed in the interior of the nanocarrier by the orientation of the hydrophobic face of each amphiphilic compound towards each other, wherein the PEG of each conjugate self-assembles on the exterior of the nanocarrier.

2. The nanocarrier of claim 1, wherein the nanocarrier further comprises a hydrophobic drug or an imaging agent, such that the hydrophobic drug or imaging agent is sequestered in the hydrophobic pocket of the nanocarrier.

3. The nanocarrier of claim 2, wherein the hydrophobic drug is selected from the group consisting of bortezomib, paclitaxel, SN38, camptothecin, etoposide and doxorubicin, docetaxel, daunorubicin, VP16, prednisone, dexamethasone, vincristine, vinblastine, temsirolimus, carmusine, sorafinib, lapatinib, and bortezomiob.

4. The nanocarrier of claim 1, wherein the nanocarrier further comprises a metal cation chelated to the porphyrin.

5. The nanocarrier of claim 1, wherein the nanocarrier further comprises a radio-metal cation selected from the group consisting of $^{64}$Cu, $^{67}$Cu, $^{177}$Lu, $^{67}$Ga, $^{111}$In, and $^{90}$Yt, wherein the radio-metal is chelated to the porphyrin.

6. The nanocarrier of claim 1, wherein the conjugates are crosslinked via the crosslinking groups.

7. The nanocarrier of claim 1, wherein each conjugate comprises:
at least two cholic acids;
at least two pyropheophorbide-a groups; and
at least two crosslinking groups, wherein the conjugates of the nanocarrier are crosslinked via the crosslinking groups.

8. The nanocarrier of claim 7, further comprising a metal chelated to at least one of the pyropheophorbide-a groups.

9. A method of treating a disease via photodynamic or photothermal therapy, comprising administering to a subject in need thereof, a therapeutically effective amount of a nanocarrier of claim 4, and exposing the subject to radiation, thereby treating the disease via photodynamic or photothermal therapy.

10. A method of imaging, comprising administering to a subject to be imaged, an effective amount of a nanocarrier of claim 1, wherein the nanocarrier further comprises an imaging agent.

11. A method of treating a disease via sonodynamic therapy, comprising administering to a subject in need thereof, a therapeutically effective amount of a nanocarrier of claim 4, and exposing the subject to a sonic wave, thereby treating the disease via sonodynamic therapy.

12. A method of detecting a tumor in a subject, comprising administering to the subject, an effective amount of a nanocarrier of claim 1;
exposing the subject to radiation at a first wavelength, wherein the radiation excites porphyrins present on the nanocarrier such that the porphyrins emit radiation at a second wavelength; and
detecting the radiation emitted by the excited porphyrins, thereby detecting the tumor.

13. The nanocarrier of claim 1, wherein each branched monomer unit X is lysine.

14. The nanocarrier of claim 1, wherein linker $L^2$, when present, is independently selected from the group consisting of polyethylene glycol, polyserine, polyglycine, poly(serine-glycine), aliphatic amino acids, 6-amino hexanoic acid, 5-amino pentanoic acid, 4-amino butanoic acid and beta-alanine.

15. The nanocarrier of claim 1, wherein linker $L^2$, when present, has the formula:

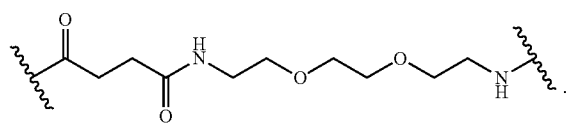 [SMILES: *NCCOCCOCCNC(=O)CCC(*)=O]

16. The nanocarrier of claim 1, wherein each remaining R is independently selected from the group consisting of cholic acid, (3α, 5β, 7α, 12α)-7,12-dihydroxy-3-(2,3-dihydroxy-1-propoxy)-cholic acid (CA-4OH), (3α, 5β, 7α, 12α)-7-hydroxy-3,12-di(2,3-dihydroxy-1-propoxy)-cholic acid (CA-5OH), (3α, 5β, 7α, 12α)-7,12-dihydroxy-3-(3-amino-2-hydroxy-1-propoxy)-cholic acid (CA-3OH—NH$_2$), cholesterol formate, doxorubicin, and rhein.

17. The nanocarrier of claim 1, wherein each remaining R is cholic acid.

18. The nanocarrier of claim 1, wherein the compound of formula I has the structure:

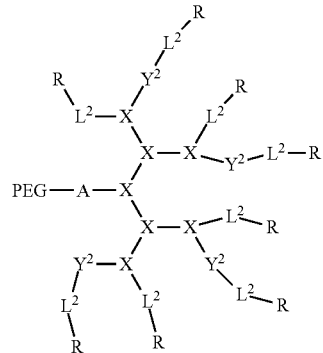

wherein
PEG is PEG5k;
each branched monomer unit X is lysine;
A is lysine;
each $L^2$ is a bond or linker Ebes;
each $Y^2$ is absent or is cysteine; and
each R is a cholic acid or a porphyrin, wherein at least one R group is a porphyrin.

19. The nanocarrier of claim 18, wherein the compound is selected from the group consisting of:

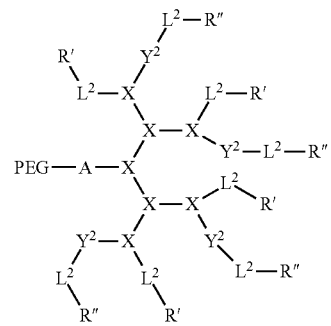

wherein
each R' is selected from the group consisting of cholic acid (CA), (3α, 5β, 7α, 12α)-7,12-dihydroxy-3-(2,3-dihydroxy-1-propoxy)-cholic acid (CA-4OH), (3α, 5β, 7α, 12α)-7-hydroxy-3,12-di(2,3-dihydroxy-1-propoxy)-cholic acid (CA-5OH) and (3α, 5β, 7α, 12α)-7,12-dihydroxy-3-(3-amino-2-hydroxy-1-propoxy)-cholic acid (CA-3OH—NH$_2$); and
each R" is a porphyrin selected from the group consisting of pyropheophorbide-a, pheophorbide, chlorin e6, purpurin and purpurinimide.

20. The nanocarrier of claim 19, wherein the porphyrin is pyropheophorbide-a.

21. The nanocarrier of claim 19, wherein the compound is selected from the group consisting of:
(1) each $L^2$ is a bond, each $Y^2$ is absent, each R' is cholic acid, each R" is pyropheophorbide-a, and subscript k is 0;

(2) each $L^2$ is the linker Ebes, each $Y^2$ is absent, each R' is cholic acid, each R" is pyropheophorbide-a, and subscript k is 0;
(3) each $L^2$ is a bond, each $Y^2$ is cysteine, each R' is cholic acid, each R" is pyropheophorbide-a, and subscript k is 0;
(4) each $L^2$ is the linker Ebes, each $Y^2$ is cysteine, each R' is cholic acid, each R" is pyropheophorbide-a, and subscript k is 0;
(5) each $L^2$ is a bond, each $Y^2$ is absent, each R' is cholic acid, each R" is pyropheophorbide-a, and subscript k is 1;
(6) each $L^2$ is the linker Ebes, each $Y^2$ is absent, each R' is cholic acid, each R" is pyropheophorbide-a, and subscript k is 1;
(7) each $L^2$ is a bond, each $Y^2$ is cysteine, each R' is cholic acid, each R" is pyropheophorbide-a, and subscript k is 1; and
(8) each $L^2$ is the linker Ebes, each $Y^2$ is cysteine, each R' is cholic acid, each R" is pyropheophorbide-a, and subscript k is 1.

\* \* \* \* \*